US007749759B2

(12) United States Patent
Fernandez-Salas et al.

(10) Patent No.: US 7,749,759 B2
(45) Date of Patent: ***Jul. 6, 2010

(54) CELL COMPOSITIONS USEFUL FOR CELL-BASED FRET ASSAYS FOR CLOSTRIDIAL TOXINS

(75) Inventors: Ester Fernandez-Salas, Fullerton, CA (US); Lance E. Steward, Irvine, CA (US); Kei Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/192,925

(22) Filed: Aug. 15, 2008

(65) Prior Publication Data

US 2009/0117572 A1 May 7, 2009

Related U.S. Application Data

(62) Division of application No. 11/621,212, filed on Jan. 9, 2007, now abandoned, and a division of application No. 10/261,161, filed on Sep. 27, 2002, now Pat. No. 7,183,066.

(51) Int. Cl.
*C12N 5/00* (2006.01)

(52) U.S. Cl. ...................... 435/325; 435/368; 435/369; 435/370; 435/372

(58) Field of Classification Search ....................... None
See application file for complete search history.

(56) References Cited

U.S. PATENT DOCUMENTS

| | | | | |
|---|---|---|---|---|
| 5,804,604 | A | 9/1998 | Frankel et al. | 530/324 |
| 5,962,637 | A | 10/1999 | Shone et al. | 530/329 |
| 5,965,699 | A | 10/1999 | Schmidt et al. | 530/326 |
| 5,981,200 | A | 11/1999 | Tsien et al. | 435/7.4 |
| 5,989,545 | A | 11/1999 | Foster et al. | 424/183.1 |
| 6,043,042 | A | 3/2000 | Shone et al. | 435/7.1 |
| 6,762,280 | B2 * | 7/2004 | Schmidt et al. | 530/300 |
| 7,374,896 | B2 | 8/2004 | Steward et al. | |
| 7,399,607 | B2 | 9/2004 | Williams et al. | |
| 7,183,066 | B2 | 2/2007 | Fernandez-Salas et al. | |
| 7,208,285 | B2 | 4/2007 | Steward et al. | |
| 7,332,567 | B2 | 2/2008 | Steward et al. | |
| 7,495,069 | B2 | 2/2009 | Steward et al. | |
| 2003/0003240 | A1 | 1/2003 | DeWent | |
| 2003/0149254 | A1* | 8/2003 | Anderson et al. | 536/23.1 |
| 2007/0122858 | A1 | 5/2007 | Fernandez-Salas et al. | |
| 2007/0275477 | A1 | 11/2007 | Gilmore et al. | |
| 2008/0003240 | A1 | 1/2008 | Fernandez-Salas et al. | |
| 2008/0064054 | A1 | 3/2008 | Fernandez-Salas et al. | |
| 2008/0160561 | A1 | 7/2008 | Fernandez-Salas et al. | |
| 2008/0166739 | A1 | 7/2008 | Steward et al. | |
| 2008/0171348 | A1 | 7/2008 | Steward et al. | |
| 2008/0176249 | A1 | 7/2008 | Steward et al. | |
| 2008/0182799 | A1 | 7/2008 | Fernandez-Salas et al. | |
| 2008/0213796 | A1 | 9/2008 | Steward et al. | |
| 2008/0220456 | A1 | 9/2008 | Williams et al. | |
| 2008/0293084 | A1 | 11/2008 | Williams et al. | |
| 2008/0293085 | A1 | 11/2008 | Williams et al. | |
| 2008/0305509 | A1 | 12/2008 | Williams et al. | |
| 2008/0305510 | A1 | 12/2008 | Williams et al. | |
| 2009/0042231 | A1 | 2/2009 | Steward et al. | |
| 2009/0053746 | A1 | 2/2009 | Steward et al. | |
| 2009/0117572 | A1 | 5/2009 | Fernandez-Salas et al. | |

FOREIGN PATENT DOCUMENTS

| | | |
|---|---|---|
| WO | WO 95/33850 | 12/1995 |
| WO | WO 99/29721 | 6/1999 |
| WO | WO 99/55899 | 11/1999 |
| WO | WO 00/34308 | 6/2000 |
| WO | WO 02/25284 | 3/2002 |
| WO | WO 03/020948 A2 | 3/2003 |

OTHER PUBLICATIONS

Mahajan et al (Chemistry and Biology; 6:401-409, May 21, 1999).*
ATCC Catalog of Cell Lines and Hybridomas, 8th edition, 1994, p. 565.*
Ray et al (Proc. Natl. Acad. Sci. USA, 90:3602-3606, 1993).*
U.S. Appl. No. 11/608,912, filed Dec. 11, 2006, Allergan, Inc.
U.S. Appl. No. 11/609,226, filed Dec. 11, 2006, Allergan, Inc.
U.S. Appl. No. 11/908,451, filed Sep. 12, 2007, Allergan, Inc.
U.S. Appl. No. 12/042,447, filed Mar. 5, 2008, Allergan, Inc.
Active Motif, LLC., "The vehicle of the future for protein transfection," Chariot Protein Transfection Product; http://www.activemotif.com/products/chariotl.html.
Anne et al., "High-Throughput Fluorogenic Assay for Determination of Botulinum Type B Neurotoxin Protease Activity," *Analytical Biochemistry* 291:253-261 (2001).
Calbiochem, "SNAPtide® Botulinum Toxin A Substrate, Fluorogenic," www.calbiochem.com, printed on Dec. 17, 2002.
Clegg, "Fluorescence Resonance Energy Transfer," *Current Opinion in Biotechnology* 6:103-110 (1995).
Cornille et al., "Solid-Phase Synthesis, Conformational Analysis and In Vitro Cleavage of Synthetic Human Synaptobrevin II 1-93 by Tetanus Toxin L Chain," *Eur. J. Biochem.* 222:173-181 (1994).

(Continued)

*Primary Examiner*—Patricia A Duffy
(74) *Attorney, Agent, or Firm*—Dean G. Stathakis; Joel B. German; Allergan, Inc.

(57) ABSTRACT

The present invention provides a method of determining clostridial toxin activity by (a) contacting with a sample a cell containing a clostridial toxin substrate that includes a donor fluorophore; an acceptor having an absorbance spectrum overlapping the emission spectrum of the donor fluorophore; and a clostridial toxin recognition sequence containing a cleavage site that intervenes between the donor fluorophore and the acceptor, where resonance energy transfer is exhibited between the donor fluorophore and the acceptor under the appropriate conditions; (b) exciting the donor fluorophore; and (c) determining resonance energy transfer of the contacted cell relative to a control cell, where a difference in resonance energy transfer of the contacted cell as compared to the control cell is indicative of clostridial toxin activity.

61 Claims, 8 Drawing Sheets

OTHER PUBLICATIONS

De Paiva et al., "Functional repair of motor endplates after botulinum neurotoxin type A poisoning: Biphasic switch of synaptic activity between nerve sprouts and their parent terminals," *Proc. Natl. Acad. Sci. USA* 96:3200-3205 (1999).

Dunican and Doherty, "Designing cell-permeant phosphopeptides to modulate intracellular signaling pathways," *Biopolymers (Peptide Sci.)* 60:45-60 (2001).

Ekong et al., "Recombinant SNAP-25 is an Effective Substrate for *Clostridium botulinum* Type A Toxin Endopeptidase Activity in vitro," *Microbiology* 143:337-3347 (1997).

Florentin et al., "A Highly Sensitive Fluorometric Assay for 'Enkephalinase,' a Neutral Metalloendopeptidase That Release Tyrosine-Glycine-Glycine from Enkephalins," *Analytical Biochemistry* 141:62-69 (1984).

Foran et al., "Differences in the Protease Activities of Tetanus and Botulinum B Toxins Revealed by the Cleavage of Vesicle-Associated Membrane Protein and Various Sized Fragments," *Biochemistry* 33:15365-15374 (1994).

Ford et al., "Protein transduction: An alternative to genetic intervention?" *Gene Therapy* 8:1-4 (2001).

Fujiwara et al., "Suppression of transmitter release by Tat HPC-1/syntaxin 1A fusion protein," *Biochim. Biophysica Acta.* 1539:225-232 (2001).

Geoghegan et al., "Fluorescence-based Continuous Assay for the Aspartyl Protease of Human Immunodeficiency Virus-1," *FEBS* 262:119-122 (1990).

Goudreau et al., "Dns-Gly-(p-NO$_2$) Phe-βAla, a Specific Fluorogenic Substrate for Neutral Endopeptidase 24.11," *Analytical Biochemistry* 219:87-95 (1994).

Graham et al., "A method to measure the interaction of Rac/Cdc42 with their binding partners using fluorescence resonance energy transfer between mutants of green fluorescent protein," *Analytical Biochem.* 296:208-217 (2001).

Hallis et al., "Development of Novel Assays for Botulinum Type A and B Neurotoxins Based on Their Endopeptidase Activities," *J. Clin. Microbiol.* 34:1934-1938 (1996).

Hanson and Stevens, "Cocrystal Structure of Synaptobrevin-II Bound to Botulinum Neurotoxin Type B at 2.0 Å Resolution," *Nature Structural Biology* 7:687-692 (2000).

Ho, et al., "Synthetic protein transduction domains: Enhanced transduction potential in Vitro and in Vivo," *Cancer Res.* 61:474-477 (2001).

Hodel, "Molecules in Focus: SNAP-25," *J. Biochem. & Cell Biol.* 30:1069-1073 (1998).

Holskin et al., "A Continuous Fluorescence-Based Assay of Human Cytomegalovirus Protease Using a Peptide Substrate," *Analytical Biochemistry* 226:148-155 (1995).

Huang et al., Ca$^{2+}$ influx and cAMP elevation overcame botulinum toxin A but not tetanus toxin inhibition of insulin exocytosis, *Am. J. Physiol. Cell Physiol.* 281:C740-C750 (2001).

Humeau et al., "How Botulinum and Tetanus Neurotoxins Block Neurotransmitter Release," *Biochimie* 82:427-446 (2000).

Kakiuchi et al., "A High Throughput Assay of the Hepatitis C Virus Nonstructural Protein 3 Serine Proteinase," *Journal of Virological Methods* 80:77-84 (1999).

Kam et al., "Probing molecular processes in live cells by quantitative multidimensional microscopy," *Trends in Cell Biology* 11:329-334 (2001).

Knapp et al., The Crystal Structure of Botulinum Toxin A zinc Protease Domain, 37$^{th}$ *Annual Meeting of the Interaqency Botulism Research Coordinating Committee* Asilomar, CA (2000).

Lacy et al., "Crystal Structure of Botulinum Neurotoxin type A and Implications for Toxicity," *Nature Structural Biology* 5:898-902 (1998).

Le Bonniec et al., "Characterization of the P$_2$' and P$_3$' Specificities of Thrombin Using Fluorescence-Quenched Substrates and Mapping of the Subsites by Mutagenesis," *Biochemistry* 35:7114-7122 (1996).

Lippincott-Schwartz et al., "Studying protein dynamics in living cells," *Nature* 2:444-456 (2001).

List Biological Laboratories, "SNAPtide For Flourometric Measurement of Botulinum Toxin Type A Activity," www.listlabs.com, printed on Dec. 23, 2002.

Matayoshi et al., "Novel Fluorogenic Substrates for Assaying Retroviral Proteases by Resonance Energy Transfer," *Science* 247:954-958 (1990).

Matsumoto et al., "A High-Throughput Screening Utilizing Intramolecular Fluorescence Resonance Energy Transfer for the Discovery of the Molecules that Bind HIV-1 TAR RNA Specifically," *Bioorganic & Medicinal Chemistry Letters* 10:1857-1861 (2000).

Mahajan et al., "Novel Mutant Green Fluorescent Protein Protease Substrates Reveal the Activation of Specific Caspases During Apoptosis," *Chemistry & Biology* 6:401-409 (1999).

McInnes and Dolly, "Ca$^{2+}$ -dependent noradrenaline release from permeabilised PC12 cells is blocked by botulinum neurotoxin A or its light chain," *FEBS Letters* 261:323-326 (1990).

Montecucco and Schiavo, "Structure and Function of Tetanus and Botulinum Neurotoxins," *Quarterly Reviews of Biophysics* 28:423-472 (1995).

Morris et al., "A new potent HIV-1 reverse transcriptase inhibitor," *J. Biol. Chem.* 274:24941-24946 (1999).

Morris et al., "A peptide carrier for the delivery of biologically active proteins into mammalian cells," *Nature Biotech.* 19:1173-1176 (2001).

Morris et al., "A novel potent strategy for gene delivery using single peptide vector as a carrier," *Nucl. Acids Res.* 27:3510-3517 (1999).

Nakatsuka et al., "D-aspartate is stored in secretory granules and released through a Ca$^{2+}$-dependent pathway in a subset of rat pheochromocytoma PC12 cells," *J. Biol. Chem.* 276:26589-26596 (2001).

Neale et al., "Botulinum neurotoxin A blocks synaptic vesicle exocytosis but not endocytosis at the nerve terminal," *J. Cell Biology* 147:1249-1260 (1999).

Niemann et al., "Clostridial Neurotoxins: New Tools for Dissecting Exocytosis," *Trends in Cell Biology* 4:179-185 (1994).

Olsen et al., "High-throughput Screening of Enzyme Libraries," *Curr. Opin. Biotechnol.* 11:331-337 (2000).

Pellizzari et al., "Tetanus and Botulinum Neurotoxins: Mechanism of Action and Therapeutic Uses," *Phil. Trans. R. Soc. Lond.* 354:259-268 (1999).

Perpetuo et al., "Development of an operational synaptobrevin-based fluorescent substrate for tetanus neurotoxin quantification," *Biotechnol. Appl. Biochem.* 36:155-161 (20002).

Prochiantz, "Messenger proteins: Homeoproteins, TAT and others," *Curr. Opin. Cell Biol.* 12:400-406 (2000).

Purkiss et al., "*Clostridium botulinum* neurotoxins act with a wide range of potencies on SH-SY5Y human neuroblastoma cells," *NeuroToxicology* 22:447-453 (2001).

Rossetto et al., "Tetanus and Botulinum Neurotoxins: Turning Bad Guys Into Good by Research," *Toxicon* 39:27-41 (2001).

Schmidt et al., "High-throughput assays for botulinum neurotoxin proteolytic activity: serotypes A, B, D, and F," *Analytical Biochem.* 296:130-137 (2001).

Schmidt et al., "Type A Botulinum Neurotoxin Proteolytic Activity: Development of Competitive Inhibitors and Implications for Substrate Specificity at the S$_1$' Binding Subsite," *FEBS Lett.* 435:61-64 (1998).

Schmidt and Bostian, "Proteolysis of Synthetic Peptides by Type A Botulinum Neurotoxin," *Journal of Protein Chemistry* 14:703-708 (1995).

Schmidt and Bostian, "Endoproteinase Activity of Type A Botulinum Neurotoxin: Substrate Requirements and Activation by Serum Albumin," *Journal of Protein Chemistry* 16:19-26 (1997).

Schwartz and Zhang, "Peptide-mediated cellular delivery," *Curr. Opin. Mol. Ther.* 2:162-167 (2000).

Schwarze and Dowdy, "In vivo protein transduction: Intracellular delivery of biologically active proteins, compounds and DNA," *Trends Pharmacol. Sci.* 21:45-48 (2000).

Schwarze et al., "In vivo protein transduction: Delivery of a biologically active protein into the mouse," *Science* 285:1569-1572 (1999).

Selvin, "The Renaissance of Fluorescence Resonance Energy Transfer," *Nature Structural Biology* 7:730-734 (2000).

Shine et al., "Sensitive method for detection of botulinum toxin type A," The 38th Interagency Botulism Research Coordinating Committee Meeting, Oct. 17-19 (2001).

Shone et al., "Proteolytic Cleavage of Synthetic Fragments of Vesicle-Associated Membrane Protein, Isoform-2 by Botulinum Type B Neurotoxin," *Eur. J. Biochem.* 217:965-971 (1993).

Sittampalam et al., "High-Throughput Screening: Advances in Assay Technologies," *Current Opinion in Chemical Biology* 1:384-391 (1997).

Swaminathan and Eswaramoorthy, "Structural Analysis of the Catalytic and Binding Sites of *Clostridium botulinum* Neurotoxin B," *Nature Structural Biology* 7:693-699 (2000).

Tawa et al., "Quantitative Analysis of Fluorescent Caspase Substrate Cleavage in Intact Cells and Identification of Novel Inhibitors of Apoptosis," *Cell Death and Differentiation* 8:30-37 (2001).

Vaidyanathan et al., "Proteolysis of SNAP-25 Isoforms by Botulinum Neurotoxin Types A, C and E: Domains and Amino Acid Residues Controlling the Formation of Enzyme-Substrate Complexes and Cleavage," *J. Neurochem.* 72:327-337 (1999).

Vitiello et al., "Intracellular Ribozyme-Catalyzed *Trans*-Cleavage of RNA Monitored by Fluorescence Resonance Energy Transfer," *RNA* 6:628-637 (2000).

Wang et al., "A Continuous Fluorescence Assay of Renin Activity," *Analytical Biochemistry* 210:351-359 (1993).

Wender et al., "The design, synthesis, and evaluation of molecules that enable or enhance cellular uptake: Peptoid molecular transporters," *Proc. Natl. Acad. Sci. USA* 97:13003-13008 (2000).

Welch et al., "Sensitivity of embryonic rat dorsal root ganglia neurons to *Clostridium botulinum* neurotoxins," *Toxicon* 38:245-258 (2000).

Wu and Brand, "Resonance Energy transfer: Methods and Applications," *Analytical Biochemistry* 218:1-13 (1994).

Xia et al., "Stable SNARE complex prior to evoked synaptic vesicle fusion revealed by fluorescence resonance energy transfer," *J. Biol. Chem.* 276:1766-1771 (2001).

Yamasaki et al., "Cleavage of Members of the Synaptobrevin/VAMP Family by Types D and F Botulinal Neurotoxins and Tetanus Toxin," *J. Biol. Chem.* 269:12764-12772 (1994).

Keller, James E. et al, FEBS Letters, vol. 456, 1999, pp. 137-142, Persistence of botulinum neurotoxin action in cultured spinal cord cells.

Vadakkanchery V. et al, "Proteolysis of SNAP-25 isoforms by botulinum neurotoxin types A, C, and E: Domains and amino acid residues controlling the formation of enzyme-substrate complexes and cleavage", J. Neurochem, vol. 72, 1999, pp. 327-337.

Siegel R. et al, "Measurement of molecular interactions in living cells by fluorescence resonance energy transfer between variants of green fluorescent protein", STKE, Jun. 27, 2000, pp. 1-6.

U.S. Appl. No. 11/621,212, filed Jan. 2007, Fernandez-Salas et al.

* cited by examiner

|     |      |                                                                              |
|-----|------|------------------------------------------------------------------------------|
|     | 1    | 75                                                                           |
| VAMP-1 HUMAN    | (1)  | MSAPAQPP─EGTEGTAPG─GGR─GPP─NM─SNRRLQQTQAQVEEVVDIIRVNVDKVLERDQKLSELDDRADALQ |
| VAMP-2 HUMAN    | (1)  | ──MSATAA─APPAA─PAGEGGPP─APPPNL─TSNRRLQQTQAQVDEVVDIMRVNVDKVLERDQKLSELDDRADALQ |
| VAMP-2 MOUSE    | (1)  | ──MSATAA─VPPAA─PAGEGGPP─APPPNL─TSNRRLQQTQAQVDEVVDIMRVNVDKVLERDQKLSELDDRADALQ |
| VAMP Bovine     | (1)  | ──MSATAA─APPAA─PAGEGGPP─APPPNL─TSNRRLQQTQAQVDEVVDIMRVNVDKVLERDQKLSELDDRADALQ |
| VAMP-2 Frog     | (1)  | ────MSAPA─AGPR─NAPG─QPP─APPPNL─ISNRRLQQTQAQVDEVVDIMRVNVDKVLERDTKLSELDDRADALQ |
| VAMP Sea Urchin | (1)  | ─────────MAAP─PPQPAPSNK─RLQQTQAQVDEVVDIMRVNVDKVLERDQALSVDDRADALQQ |

|     |      |                                                                              |
|-----|------|------------------------------------------------------------------------------|
|     | 76   | 123                                                                          |
| VAMP-1 HUMAN    | (75) | GASQFETSAAKLKRKYWWKNCKMMIMLGAICAIVVLVIF─────                                  |
| VAMP-2 HUMAN    | (73) | GASQFETSAAKLKRKYWWKNLKMMIILGVICAIILIIIIVYFST─                                 |
| VAMP-2 MOUSE    | (73) | GASQFETSAAKLKRKYWWKNLKMMIILGVICAIILIIIIVYFS─                                  |
| VAMP Bovine     | (73) | GASQFETSAAKLKRKYWWKNLKMMIILGVICAIILIIIIVYFS─                                  |
| VAMP-2 Frog     | (71) | GASQFETSAAKLKRKYWWKNLKMMIILGVICAIILIIIIVYFS─                                  |
| VAMP Sea Urchin | (57) | GASQFETINAGKLKRKYWWKNCKMMIMLATIIIVLIIIIAIVQSKK                                |

SEQUENCE LISTING

<160> NUMBER OF SEQ ID NOS: 109

<210> SEQ ID NO 1
<211> LENGTH: 16
<212> TYPE: PRT
<213> ORGANISM: Artificial Sequence
<220> FEATURE:
<223> OTHER INFORMATION: synthetic construct

<400> SEQUENCE: 1

Arg Gln Ile Lys Ile Trp Phe Gln Asn Arg Arg Met Lys Trp Lys Lys
 1               5                  10                  15

<210> SEQ ID NO 2
<211> LENGTH: 11
<212> TYPE: PRT
<213> ORGANISM: Artificial Sequence
<220> FEATURE:
<223> OTHER INFORMATION: synthetic construct

<400> SEQUENCE: 2

Tyr Gly Arg Lys Lys Arg Arg Gln Arg Arg Arg
 1               5                  10

<210> SEQ ID NO 3
<211> LENGTH: 301
<212> TYPE: PRT
<213> ORGANISM: human herpesvirus 1

<400> SEQUENCE: 3

Met Thr Ser Arg Arg Ser Val Lys Ser Gly Pro Arg Glu Val Pro Arg
 1               5                  10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
    50                  55                  60

Tyr Ala Leu Tyr Gly Gly Ser Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Ala Gly Ser Gly Gly Ala Gly Arg
            100                 105                 110

Arg Thr Pro Thr Thr Ala Pro Arg Ala Pro Arg Thr Gln Arg Val Ala
        115                 120                 125

Thr Lys Ala Pro Ala Ala Pro Ala Ala Glu Thr Thr Arg Gly Arg Lys
    130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
            180                 185                 190

Val Ala Gly Phe Asn Lys Arg Val Phe Cys Ala Ala Val Gly Arg Leu
        195                 200                 205

Ala Ala Met His Ala Arg Met Ala Ala Val Gln Leu Trp Asp Met Ser
    210                 215                 220

```
Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
            245                 250                 255

Glu Leu Val Asn Pro Asp Val Val Gln Asp Val Asp Ala Ala Thr Ala
        260                 265                 270

Thr Arg Gly Arg Ser Ala Ala Ser Arg Pro Thr Glu Arg Pro Arg Ala
    275                 280                 285

Pro Ala Arg Ser Ala Ser Arg Pro Arg Pro Val Glu
290                 295                 300

<210> SEQ ID NO 4
<211> LENGTH: 206
<212> TYPE: PRT
<213> ORGANISM: Homo sapiens

<400> SEQUENCE: 4

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205

<210> SEQ ID NO 5
<211> LENGTH: 206
<212> TYPE: PRT
<213> ORGANISM: Mus musculus

<400> SEQUENCE: 5

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45
```

```
Met Leu Asp Glu Gln Gly Glu Gln Leu Glu Arg Ile Glu Gly Met
 50                  55                  60

Asp Gln Ile Asn Lys Asp Met Lys Glu Ala Glu Lys Asn Leu Thr Asp
 65                  70                  75                  80

Leu Gly Lys Phe Cys Gly Leu Cys Val Cys Pro Cys Asn Lys Leu Lys
                 85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205

<210> SEQ ID NO 6
<211> LENGTH: 212
<212> TYPE: PRT
<213> ORGANISM: Drosophila melanogaster

<400> SEQUENCE: 6

Met Pro Ala Asp Pro Ser Glu Glu Val Ala Pro Gln Val Pro Lys Thr
 1               5                  10                  15

Glu Leu Glu Glu Leu Gln Ile Asn Ala Gln Gly Val Ala Asp Glu Ser
            20                  25                  30

Leu Glu Ser Thr Arg Arg Met Leu Ala Leu Cys Glu Glu Ser Lys Glu
        35                  40                  45

Ala Gly Ile Arg Thr Leu Val Ala Leu Asp Asp Gln Gly Glu Gln Leu
 50                  55                  60

Asp Arg Ile Glu Glu Gly Met Asp Gln Ile Asn Ala Asp Met Arg Glu
 65                  70                  75                  80

Ala Glu Lys Asn Leu Ser Gly Met Glu Lys Cys Cys Gly Ile Cys Val
                 85                  90                  95

Leu Pro Cys Asn Lys Ser Gln Ser Phe Lys Glu Asp Asp Gly Thr Trp
            100                 105                 110

Lys Gly Asn Asp Asp Gly Lys Val Val Asn Asn Gln Pro Gln Arg Val
        115                 120                 125

Met Asp Asp Arg Asn Gly Met Met Ala Gln Ala Gly Tyr Ile Gly Arg
130                 135                 140

Ile Thr Asn Asp Ala Arg Glu Asp Glu Met Glu Glu Asn Met Gly Gln
145                 150                 155                 160

Val Asn Thr Met Ile Gly Asn Leu Arg Asn Met Ala Leu Asp Met Gly
                165                 170                 175

Ser Glu Leu Glu Asn Gln Asn Arg Gln Ile Asp Arg Ile Asn Arg Lys
            180                 185                 190

Gly Glu Ser Asn Glu Ala Arg Ile Ala Val Ala Asn Gln Arg Ala His
        195                 200                 205

Gln Leu Leu Lys
```

<210> SEQ ID NO 7
<211> LENGTH: 203
<212> TYPE: PRT
<213> ORGANISM: Carassius auratus

<400> SEQUENCE: 7

```
Met Ala Asp Glu Ala Asp Met Arg Asn Glu Leu Thr Asp Met Gln Ala
  1               5                  10                  15
Arg Ala Asp Gln Leu Gly Asp Glu Ser Leu Glu Ser Thr Arg Arg Met
             20                  25                  30
Leu Gln Leu Val Glu Glu Ser Lys Asp Ala Gly Ile Arg Thr Leu Val
         35                  40                  45
Met Leu Asp Glu Gln Gly Glu Gln Leu Glu Arg Ile Glu Glu Gly Met
     50                  55                  60
Asp Gln Ile Asn Lys Asp Met Lys Glu Ala Glu Lys Asn Leu Thr Asp
 65                  70                  75                  80
Leu Gly Asn Leu Cys Gly Leu Cys Pro Cys Pro Cys Asn Lys Leu Lys
                 85                  90                  95
Gly Gly Gly Gln Ser Trp Gly Asn Asn Gln Asp Gly Val Val Ser Ser
            100                 105                 110
Gln Pro Ala Arg Val Val Asp Glu Arg Glu Gln Met Ala Ile Ser Gly
        115                 120                 125
Gly Phe Ile Arg Arg Val Thr Asn Asp Ala Arg Glu Asn Glu Met Asp
    130                 135                 140
Glu Asn Leu Glu Gln Val Gly Ser Ile Ile Gly Asn Leu Arg His Met
145                 150                 155                 160
Ala Leu Asp Met Gly Asn Glu Ile Asp Thr Gln Asn Arg Gln Ile Asp
                165                 170                 175
Arg Ile Met Asp Met Ala Asp Ser Asn Lys Thr Arg Ile Asp Glu Ala
            180                 185                 190
Asn Gln Arg Ala Thr Lys Met Leu Gly Ser Gly
        195                 200
```

<210> SEQ ID NO 8
<211> LENGTH: 212
<212> TYPE: PRT
<213> ORGANISM: Strongylocentrotus purpuratus

<400> SEQUENCE: 8

```
Met Glu Asp Gln Asn Asp Met Asn Met Arg Ser Glu Leu Glu Glu Ile
  1               5                  10                  15
Gln Met Gln Ser Asn Met Gln Thr Asp Glu Ser Leu Glu Ser Thr Arg
             20                  25                  30
Arg Met Leu Gln Met Ala Glu Glu Ser Gln Asp Met Gly Ile Lys Thr
         35                  40                  45
Leu Val Met Leu Asp Glu Gln Gly Glu Gln Leu Asp Arg Ile Glu Glu
     50                  55                  60
Gly Met Asp Gln Ile Asn Thr Asp Met Arg Glu Ala Glu Lys Asn Leu
 65                  70                  75                  80
Thr Gly Leu Glu Lys Cys Cys Gly Ile Cys Val Cys Pro Trp Lys Lys
                 85                  90                  95
Leu Gly Asn Phe Glu Lys Gly Asp Asp Tyr Lys Lys Thr Trp Lys Gly
            100                 105                 110
Asn Asp Asp Gly Lys Val Asn Ser His Gln Pro Met Arg Met Glu Asp
```

```
            115                 120                 125
Asp Arg Asp Gly Cys Gly Gly Asn Ala Ser Met Ile Thr Arg Ile Thr
    130                 135                 140

Asn Asp Ala Arg Glu Asp Glu Met Asp Glu Asn Leu Thr Gln Val Ser
145                 150                 155                 160

Ser Ile Val Gly Asn Leu Arg His Met Ala Ile Asp Met Gln Ser Glu
                165                 170                 175

Ile Gly Ala Gln Asn Ser Gln Val Gly Arg Ile Thr Ser Lys Ala Glu
            180                 185                 190

Ser Asn Glu Gly Arg Ile Asn Ser Ala Asp Lys Arg Ala Lys Asn Ile
        195                 200                 205

Leu Arg Asn Lys
    210

<210> SEQ ID NO 9
<211> LENGTH: 249
<212> TYPE: PRT
<213> ORGANISM: Gallus gallus

<400> SEQUENCE: 9

Met Ala Glu Asp Ala Asp Met Arg Asn Glu Leu Glu Met Gln Arg
 1               5                  10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Asp Arg Val Glu Glu Gly Met
        50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
                100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Leu Ile Pro Ile Lys Pro Gly Leu
            180                 185                 190

Met Lys Pro Thr Ser Val Gln Gln Arg Cys Ser Ala Val Val Lys Cys
        195                 200                 205

Ser Lys Val His Phe Leu Leu Met Leu Ser Gln Arg Ala Val Pro Ser
    210                 215                 220

Cys Phe Tyr His Gly Ile Tyr Leu Leu Gly Leu His Thr Cys Thr Tyr
225                 230                 235                 240

Gln Pro His Cys Lys Cys Cys Pro Val
                245

<210> SEQ ID NO 10
<211> LENGTH: 118
```

```
<212> TYPE: PRT
<213> ORGANISM: Homo sapiens

<400> SEQUENCE: 10

Met Ser Ala Pro Ala Gln Pro Pro Ala Glu Gly Thr Glu Gly Thr Ala
 1               5                  10                  15

Pro Gly Gly Gly Pro Pro Gly Pro Pro Asn Met Thr Ser Asn Arg
                20                  25                  30

Arg Leu Gln Gln Thr Gln Ala Gln Val Glu Glu Val Val Asp Ile Ile
                35                  40                  45

Arg Val Asn Val Asp Lys Val Leu Glu Arg Asp Gln Lys Leu Ser Glu
        50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
                100                 105                 110

Val Ile Tyr Phe Phe Thr
            115

<210> SEQ ID NO 11
<211> LENGTH: 116
<212> TYPE: PRT
<213> ORGANISM: Homo sapiens

<400> SEQUENCE: 11

Met Ser Ala Thr Ala Ala Thr Ala Pro Pro Ala Ala Pro Ala Gly Glu
 1               5                  10                  15

Gly Gly Pro Pro Ala Pro Pro Pro Asn Leu Thr Ser Asn Arg Arg Leu
                20                  25                  30

Gln Gln Thr Gln Ala Gln Val Asp Glu Val Val Asp Ile Met Arg Val
            35                  40                  45

Asn Val Asp Lys Val Leu Glu Arg Asp Gln Lys Leu Ser Glu Leu Asp
        50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
                100                 105                 110

Tyr Phe Ser Ser
            115

<210> SEQ ID NO 12
<211> LENGTH: 116
<212> TYPE: PRT
<213> ORGANISM: Mus musculus

<400> SEQUENCE: 12

Met Ser Ala Thr Ala Ala Thr Val Pro Pro Ala Ala Pro Ala Gly Glu
 1               5                  10                  15

Gly Gly Pro Pro Ala Pro Pro Pro Asn Leu Thr Ser Asn Arg Arg Leu
                20                  25                  30

Gln Gln Thr Gln Ala Gln Val Asp Glu Val Val Asp Ile Met Arg Val
            35                  40                  45

Asn Val Asp Lys Val Leu Glu Arg Asp Gln Lys Leu Ser Glu Leu Asp
```

```
            50                   55                   60
Asp Arg Ala Asp Ala Leu Gln Ala Gly Ala Ser Gln Phe Glu Thr Ser
 65                  70                  75                  80

Ala Ala Lys Leu Lys Arg Lys Tyr Trp Trp Lys Asn Leu Lys Met Met
                 85                  90                  95

Ile Ile Leu Gly Val Ile Cys Ala Ile Ile Leu Ile Ile Ile Ile Val
                100                 105                 110

Tyr Phe Ser Thr
            115

<210> SEQ ID NO 13
<211> LENGTH: 116
<212> TYPE: PRT
<213> ORGANISM: Bos taurus

<400> SEQUENCE: 13

Met Ser Ala Thr Ala Ala Thr Ala Pro Pro Ala Ala Pro Ala Gly Glu
  1               5                  10                  15

Gly Gly Pro Pro Ala Pro Pro Asn Leu Thr Ser Asn Arg Arg Leu
                 20                  25                  30

Gln Gln Thr Gln Ala Gln Val Asp Glu Val Val Asp Ile Met Arg Val
             35                  40                  45

Asn Val Asp Lys Val Leu Glu Arg Asp Gln Lys Leu Ser Glu Leu Asp
 50                  55                  60

Asp Arg Ala Asp Ala Leu Gln Ala Gly Ala Ser Gln Phe Glu Thr Ser
 65                  70                  75                  80

Ala Ala Lys Leu Lys Arg Lys Tyr Trp Trp Lys Asn Leu Lys Met Met
                 85                  90                  95

Ile Ile Leu Gly Val Ile Cys Ala Ile Ile Leu Ile Ile Ile Ile Val
                100                 105                 110

Tyr Phe Ser Ser
            115

<210> SEQ ID NO 14
<211> LENGTH: 114
<212> TYPE: PRT
<213> ORGANISM: Xenopus laevis

<400> SEQUENCE: 14

Met Ser Ala Pro Ala Ala Gly Pro Pro Ala Ala Pro Gly Asp Gly
  1               5                  10                  15

Ala Pro Gln Gly Pro Pro Asn Leu Thr Ser Asn Arg Arg Leu Gln Gln
                 20                  25                  30

Thr Gln Ala Gln Val Asp Glu Val Val Asp Ile Met Arg Val Asn Val
             35                  40                  45

Asp Lys Val Leu Glu Arg Asp Thr Lys Leu Ser Glu Leu Asp Asp Arg
 50                  55                  60

Ala Asp Ala Leu Gln Ala Gly Ala Ser Gln Phe Glu Thr Ser Ala Ala
 65                  70                  75                  80

Lys Leu Lys Arg Lys Tyr Trp Trp Lys Asn Met Lys Met Met Ile Ile
                 85                  90                  95

Met Gly Val Ile Cys Ala Ile Ile Leu Ile Ile Ile Ile Val Tyr Phe
                100                 105                 110

Ser Thr

<210> SEQ ID NO 15
```

<211> LENGTH: 104
<212> TYPE: PRT
<213> ORGANISM: Strongylocentrotus purpuratus

<400> SEQUENCE: 15

Met Ala Ala Pro Pro Pro Gln Pro Ala Pro Ser Asn Lys Arg Leu
1               5                   10                  15

Gln Gln Thr Gln Ala Gln Val Asp Glu Val Val Asp Ile Met Arg Val
            20                  25                  30

Asn Val Asp Lys Val Leu Glu Arg Asp Gln Ala Leu Ser Val Leu Asp
        35                  40                  45

Asp Arg Ala Asp Ala Leu Gln Gln Gly Ala Ser Gln Phe Glu Thr Asn
    50                  55                  60

Ala Gly Lys Leu Lys Arg Lys Tyr Trp Trp Lys Asn Cys Lys Met Met
65                  70                  75                  80

Ile Ile Leu Ala Ile Ile Ile Val Ile Leu Ile Ile Ile Val
                85                  90                  95

Ala Ile Val Gln Ser Gln Lys Lys
            100

<210> SEQ ID NO 16
<211> LENGTH: 288
<212> TYPE: PRT
<213> ORGANISM: Homo sapiens

<400> SEQUENCE: 16

Met Lys Asp Arg Thr Gln Glu Leu Arg Thr Ala Lys Asp Ser Asp Asp
1               5                   10                  15

Asp Asp Asp Val Ala Val Thr Val Asp Arg Asp Arg Phe Met Asp Glu
            20                  25                  30

Phe Phe Glu Gln Val Glu Glu Ile Arg Gly Phe Ile Asp Lys Ile Ala
        35                  40                  45

Glu Asn Val Glu Glu Val Lys Arg Lys His Ser Ala Ile Leu Ala Ser
    50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
    130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
        195                 200                 205

Ile Arg Glu Leu His Asp Met Phe Met Asp Met Ala Met Leu Val Glu
    210                 215                 220

Ser Gln Gly Glu Met Ile Asp Arg Ile Glu Tyr Asn Val Glu His Ala
225                 230                 235                 240

```
Val Asp Tyr Val Glu Arg Ala Val Ser Asp Thr Lys Lys Ala Val Lys
            245                 250                 255

Tyr Gln Ser Lys Ala Arg Arg Lys Lys Ile Met Ile Ile Ile Cys Cys
            260                 265                 270

Val Ile Leu Gly Ile Val Ile Ala Ser Thr Val Gly Ile Phe Ala
            275                 280                 285

<210> SEQ ID NO 17
<211> LENGTH: 288
<212> TYPE: PRT
<213> ORGANISM: Homo sapiens

<400> SEQUENCE: 17

Met Lys Asp Arg Thr Gln Glu Leu Arg Ser Ala Lys Asp Ser Asp Asp
  1               5                  10                  15

Glu Glu Glu Val Val His Val Asp Arg Asp His Phe Met Asp Glu Phe
                 20                  25                  30

Phe Glu Gln Val Glu Glu Ile Arg Gly Cys Ile Glu Lys Leu Ser Glu
             35                  40                  45

Asp Val Glu Gln Val Lys Lys Gln His Ser Ala Ile Leu Ala Ala Pro
         50                  55                  60

Asn Pro Asp Glu Lys Thr Lys Gln Glu Leu Glu Asp Leu Thr Ala Asp
 65                  70                  75                  80

Ile Lys Lys Thr Ala Asn Lys Val Arg Ser Lys Leu Lys Ala Ile Glu
                 85                  90                  95

Gln Ser Ile Glu Gln Glu Glu Gly Leu Asn Arg Ser Ser Ala Asp Leu
                100                 105                 110

Arg Ile Arg Lys Thr Gln His Ser Thr Leu Ser Arg Lys Phe Val Glu
            115                 120                 125

Val Met Thr Glu Tyr Asn Ala Thr Gln Ser Lys Tyr Arg Asp Arg Cys
        130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Ile Cys Cys Val
            260                 265                 270

Val Leu Gly Val Val Leu Ala Ser Ser Ile Gly Gly Thr Leu Gly Leu
        275                 280                 285

<210> SEQ ID NO 18
<211> LENGTH: 288
<212> TYPE: PRT
<213> ORGANISM: Mus musculus

<400> SEQUENCE: 18
```

```
Met Lys Asp Arg Thr Gln Glu Leu Arg Thr Ala Lys Asp Ser Asp Asp
 1               5                  10                 15

Asp Asp Asp Val Thr Val Thr Val Asp Arg Asp Arg Phe Met Asp Glu
             20                  25                  30

Phe Phe Glu Gln Val Glu Glu Ile Arg Gly Phe Ile Asp Lys Ile Ala
         35                  40                  45

Glu Asn Val Glu Val Lys Arg Lys His Ser Ala Ile Leu Ala Ser
     50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                 85                  90                  95

Glu Gln Ser Ile Glu Gln Glu Gly Leu Asn Arg Ser Ser Ala Asp
             100                 105                 110

Leu Arg Ile Arg Lys Thr Gln His Ser Thr Leu Ser Arg Lys Phe Val
         115                 120                 125

Glu Val Met Ser Glu Tyr Asn Ala Thr Gln Ser Asp Tyr Arg Glu Arg
130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                 165                 170                 175

Phe Ala Ser Gly Ile Ile Met Asp Ser Ser Ile Ser Lys Gln Ala Leu
             180                 185                 190

Ser Glu Ile Glu Thr Arg His Ser Glu Ile Ile Lys Leu Glu Thr Ser
         195                 200                 205

Ile Arg Glu Leu His Asp Met Phe Met Asp Met Ala Met Leu Val Glu
         210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                 245                 250                 255

Tyr Gln Ser Lys Ala Arg Arg Lys Lys Ile Met Ile Ile Cys Cys
         260                 265                 270

Val Ile Leu Gly Ile Ile Ala Ser Thr Ile Gly Gly Ile Phe Gly
         275                 280                 285

<210> SEQ ID NO 19
<211> LENGTH: 291
<212> TYPE: PRT
<213> ORGANISM: Drosophila melanogaster

<400> SEQUENCE: 19

Met Thr Lys Asp Arg Leu Ala Ala Leu His Ala Ala Gln Ser Asp Asp
 1               5                  10                 15

Glu Glu Glu Thr Glu Val Ala Val Asn Val Asp Gly His Asp Ser Tyr
             20                  25                  30

Met Asp Asp Phe Phe Ala Gln Val Glu Glu Ile Arg Gly Met Ile Asp
         35                  40                  45

Lys Val Gln Asp Asn Val Glu Glu Val Lys Lys His Ser Ala Ile
     50                  55                  60

Leu Ser Ala Pro Gln Thr Asp Glu Lys Thr Lys Gln Glu Leu Glu Asp
65                  70                  75                  80

Leu Met Ala Asp Ile Lys Lys Asn Ala Asn Arg Val Arg Gly Lys Leu
```

-continued

```
                    85                  90                  95
Lys Gly Ile Glu Gln Asn Ile Glu Gln Glu Gln Gln Asn Lys Ser
                100                 105                 110
Ser Ala Asp Leu Arg Ile Arg Lys Thr Gln His Ser Thr Leu Ser Arg
            115                 120                 125
Lys Phe Val Glu Val Met Thr Glu Tyr Asn Arg Thr Gln Thr Asp Tyr
        130                 135                 140
Arg Glu Arg Cys Lys Gly Arg Ile Gln Arg Gln Leu Glu Ile Thr Gly
145                 150                 155                 160
Arg Pro Thr Asn Asp Asp Glu Leu Glu Lys Met Leu Glu Glu Gly Asn
                165                 170                 175
Ser Ser Val Phe Thr Gln Gly Ile Ile Met Glu Thr Gln Gln Ala Lys
            180                 185                 190
Gln Thr Leu Ala Asp Ile Glu Ala Arg His Gln Asp Ile Met Lys Leu
        195                 200                 205
Glu Thr Ser Ile Lys Glu Leu His Asp Met Phe Met Asp Met Ala Met
    210                 215                 220
Leu Val Glu Ser Gln Gly Glu Met Ile Asp Arg Ile Glu Tyr His Val
225                 230                 235                 240
Glu His Ala Met Asp Tyr Val Gln Thr Ala Thr Gln Asp Thr Lys Lys
                245                 250                 255
Ala Leu Lys Tyr Gln Ser Lys Ala Arg Arg Lys Lys Ile Met Ile Leu
            260                 265                 270
Ile Cys Leu Thr Val Leu Gly Ile Leu Ala Ala Ser Tyr Val Ser Ser
        275                 280                 285
Tyr Phe Met
    290

<210> SEQ ID NO 20
<211> LENGTH: 291
<212> TYPE: PRT
<213> ORGANISM: Caenorhabditis  elegans

<400> SEQUENCE: 20

Met Thr Lys Asp Arg Leu Ser Ala Leu Lys Ala Ala Gln Ser Glu Asp
  1               5                  10                  15
Glu Gln Asp Asp Asp Met His Met Asp Thr Gly Asn Ala Gln Tyr Met
                 20                  25                  30
Glu Glu Phe Phe Glu Gln Val Glu Glu Ile Arg Gly Ser Val Asp Ile
             35                  40                  45
Ile Ala Asn Asn Val Glu Glu Val Lys Lys Lys His Ser Ala Ile Leu
         50                  55                  60
Ser Asn Pro Val Asn Asp Gln Lys Thr Lys Glu Glu Leu Asp Glu Leu
 65                  70                  75                  80
Met Ala Val Ile Lys Arg Ala Ala Asn Lys Val Arg Gly Lys Leu Lys
                 85                  90                  95
Leu Ile Glu Asn Ala Ile Asp His Asp Glu Gln Gly Ala Gly Asn Ala
                100                 105                 110
Asp Leu Arg Ile Arg Lys Thr Gln His Ser Thr Leu Ser Arg Arg Phe
            115                 120                 125
Val Glu Val Met Thr Asp Tyr Asn Lys Thr Gln Thr Asp Tyr Arg Glu
        130                 135                 140
Arg Cys Lys Gly Arg Ile Gln Arg Gln Leu Asp Ile Ala Gly Lys Gln
145                 150                 155                 160
```

```
Val Gly Asp Glu Asp Leu Glu Met Ile Glu Ser Gly Asn Pro Gly
            165                 170                 175

Val Phe Thr Gln Gly Ile Ile Thr Asp Thr Gln Gln Ala Lys Gln Thr
            180                 185                 190

Leu Ala Asp Ile Glu Ala Arg His Asn Asp Ile Met Lys Leu Glu Ser
            195                 200                 205

Ser Ile Arg Glu Leu His Asp Met Phe Met Asp Met Ala Met Leu Val
            210                 215                 220

Glu Ser Gln Gly Glu Met Val Asp Arg Ile Glu Tyr Asn Val Glu His
225                 230                 235                 240

Ala Lys Glu Phe Val Asp Arg Ala Val Ala Asp Thr Lys Lys Ala Val
                245                 250                 255

Gln Tyr Gln Ser Lys Ala Arg Lys Lys Ile Cys Ile Leu Val Thr
            260                 265                 270

Gly Val Ile Leu Ile Thr Gly Leu Ile Ile Phe Ile Leu Phe Tyr Ala
            275                 280                 285

Lys Val Leu
    290

<210> SEQ ID NO 21
<211> LENGTH: 288
<212> TYPE: PRT
<213> ORGANISM: Strongylocentrotus purpuratus

<400> SEQUENCE: 21

Met Arg Asp Arg Leu Gly Ser Leu Lys Arg Asn Glu Glu Asp Asp Val
1               5                   10                  15

Gly Pro Glu Val Ala Val Asn Val Ser Glu Lys Phe Met Glu Glu
            20                  25                  30

Phe Phe Glu Gln Val Glu Glu Val Arg Asn Asn Ile Asp Lys Ile Ser
        35                  40                  45

Lys Asn Val Asp Glu Val Lys Lys His Ser Asp Ile Leu Ser Ala
    50                  55                  60

Pro Gln Ala Asp Glu Lys Val Lys Asp Glu Leu Glu Glu Leu Met Ser
65                  70                  75                  80

Asp Ile Lys Lys Thr Ala Asn Lys Val Arg Ala Lys Leu Lys Met Met
                85                  90                  95

Glu Gln Ser Ile Glu Gln Glu Ser Ala Lys Met Asn Ser Ala Asp
            100                 105                 110

Val Arg Ile Arg Lys Thr Gln His Ser Thr Leu Ser Arg Lys Phe Val
        115                 120                 125

Glu Val Met Thr Asp Tyr Asn Ser Thr Gln Thr Asp Tyr Arg Glu Arg
    130                 135                 140

Cys Lys Gly Arg Ile Gln Arg Gln Leu Glu Ile Thr Gly Lys Ser Thr
145                 150                 155                 160

Thr Asp Ala Glu Leu Glu Asp Met Leu Glu Ser Gly Asn Pro Ala Ile
                165                 170                 175

Phe Thr Ser Gly Ile Ile Met Asp Thr Gln Ala Lys Gln Thr Leu
            180                 185                 190

Arg Asp Ile Glu Ala Arg His Asn Asp Ile Ile Lys Leu Glu Ser Ser
        195                 200                 205

Ile Arg Glu Leu His Asp Met Phe Met Asp Met Ala Met Leu Val Glu
    210                 215                 220

Ser Gln Gly Glu Met Ile Asp Arg Ile Glu Tyr Asn Val Glu Gln Ser
225                 230                 235                 240
```

```
Val Asp Tyr Val Glu Thr Ala Lys Met Asp Thr Lys Lys Ala Val Lys
                245                 250                 255

Tyr Gln Ser Lys Ala Arg Arg Lys Lys Phe Tyr Ile Ala Ile Cys Cys
            260                 265                 270

Gly Val Ala Leu Gly Ile Leu Val Leu Ile Ile Val Leu Ala
        275                 280                 285

<210> SEQ ID NO 22
<211> LENGTH: 16
<212> TYPE: PRT
<213> ORGANISM: Artificial Sequence
<220> FEATURE:
<223> OTHER INFORMATION: synthetic construct

<400> SEQUENCE: 22

Ala Ala Val Ala Leu Leu Pro Ala Val Leu Leu Ala Leu Leu Ala Pro
1               5                   10                  15

<210> SEQ ID NO 23
<211> LENGTH: 12
<212> TYPE: PRT
<213> ORGANISM: Artificial Sequence
<220> FEATURE:
<223> OTHER INFORMATION: synthetic construct

<400> SEQUENCE: 23

Thr Pro Pro Lys Lys Lys Arg Lys Val Glu Asp Pro
1               5                   10

<210> SEQ ID NO 24
<211> LENGTH: 27
<212> TYPE: PRT
<213> ORGANISM: Artificial Sequence
<220> FEATURE:
<223> OTHER INFORMATION: synthetic construct

<400> SEQUENCE: 24

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 25
<211> LENGTH: 16
<212> TYPE: PRT
<213> ORGANISM: Artificial Sequence
<220> FEATURE:
<223> OTHER INFORMATION: synthetic construct

<400> SEQUENCE: 25

Lys Lys Trp Lys Met Arg Arg Asn Gln Phe Trp Ile Lys Ile Gln Arg
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: synthetic construct

<400> SEQUENCE: 26

Arg Gln Ile Lys Ile Trp Phe Gln Asn Arg Arg Met Lys Trp Lys Lys
1               5                   10                  15
```

```
<210> SEQ ID NO 27
<211> LENGTH: 16
<212> TYPE: PRT
<213> ORGANISM: Artificial Sequence
<220> FEATURE:
<223> OTHER INFORMATION: synthetic construct

<400> SEQUENCE: 27

Arg Gln Ile Lys Ile Trp Phe Pro Asn Arg Arg Met Lys Trp Lys Lys
 1               5                  10                  15

<210> SEQ ID NO 28
<211> LENGTH: 16
<212> TYPE: PRT
<213> ORGANISM: Artificial Sequence
<220> FEATURE:
<223> OTHER INFORMATION: synthetic construct

<400> SEQUENCE: 28

Arg Gln Pro Lys Ile Trp Phe Pro Asn Arg Arg Met Pro Trp Lys Lys
 1               5                  10                  15

<210> SEQ ID NO 29
<211> LENGTH: 16
<212> TYPE: PRT
<213> ORGANISM: Artificial Sequence
<220> FEATURE:
<223> OTHER INFORMATION: synthetic construct

<400> SEQUENCE: 29

Arg Gln Ile Lys Ile Trp Phe Gln Asn Met Arg Arg Lys Trp Lys Lys
 1               5                  10                  15

<210> SEQ ID NO 30
<211> LENGTH: 16
<212> TYPE: PRT
<213> ORGANISM: Artificial Sequence
<220> FEATURE:
<223> OTHER INFORMATION: synthetic construct

<400> SEQUENCE: 30

Arg Gln Ile Arg Ile Trp Phe Gln Asn Arg Arg Met Arg Trp Arg Arg
 1               5                  10                  15

<210> SEQ ID NO 31
<211> LENGTH: 16
<212> TYPE: PRT
<213> ORGANISM: Artificial Sequence
<220> FEATURE:
<223> OTHER INFORMATION: synthetic construct

<400> SEQUENCE: 31

Arg Arg Trp Arg Arg Trp Trp Arg Arg Trp Trp Arg Arg Trp Arg Arg
 1               5                  10                  15

<210> SEQ ID NO 32
<211> LENGTH: 4
<212> TYPE: PRT
<213> ORGANISM: Artificial Sequence
<220> FEATURE:
<223> OTHER INFORMATION: synthetic construct
<221> NAME/KEY: REPEAT
<222> LOCATION: 4
<223> OTHER INFORMATION: Extent of lysine repetition unknown.

<400> SEQUENCE: 32

Ser Cys Trp Lys
 1
```

```
<210> SEQ ID NO 33
<211> LENGTH: 4
<212> TYPE: PRT
<213> ORGANISM: Artificial Sequence
<220> FEATURE:
<223> OTHER INFORMATION: synthetic construct
<221> NAME/KEY: REPEAT
<222> LOCATION: (1)...(4)
<223> OTHER INFORMATION: extent of repetition unknown.

<400> SEQUENCE: 33

Leu Ala Arg Leu
 1

<210> SEQ ID NO 34
<211> LENGTH: 46
<212> TYPE: PRT
<213> ORGANISM: Artificial Sequence
<220> FEATURE:
<223> OTHER INFORMATION: synthetic construct

<400> SEQUENCE: 34

Lys Lys Lys Lys Lys Lys Lys Lys Lys Lys Lys Lys Lys Lys Lys Lys
 1               5                  10                  15

Gly Gly Cys Arg Gly Asp Met Phe Gly Cys Ala Lys Lys Lys Lys Lys
            20                  25                  30

Lys Lys Lys Lys Lys Lys Lys Lys Lys Lys Arg Gly Asp
        35                  40                  45

<210> SEQ ID NO 35
<211> LENGTH: 20
<212> TYPE: PRT
<213> ORGANISM: Artificial Sequence
<220> FEATURE:
<223> OTHER INFORMATION: synthetic construct

<400> SEQUENCE: 35

Cys Trp Lys Lys Lys Lys Lys Lys Lys Lys Lys Lys Lys Lys Lys Lys
 1               5                  10                  15

Lys Lys Lys Lys
            20

<210> SEQ ID NO 36
<211> LENGTH: 40
<212> TYPE: PRT
<213> ORGANISM: Artificial Sequence
<220> FEATURE:
<223> OTHER INFORMATION: synthetic construct

<400> SEQUENCE: 36

Lys Lys Lys Lys Lys Lys Lys Lys Lys Lys Lys Lys Lys Lys Lys Lys
 1               5                  10                  15

Lys Lys Trp Cys Cys Trp Lys Lys Lys Lys Lys Lys Lys Lys Lys Lys
            20                  25                  30

Lys Lys Lys Lys Lys Lys Lys Lys
        35                  40

<210> SEQ ID NO 37
<211> LENGTH: 12
<212> TYPE: PRT
<213> ORGANISM: Artificial Sequence
<220> FEATURE:
<223> OTHER INFORMATION: synthetic construct
```

```
<400> SEQUENCE: 37

Pro Leu Ala Glu Ile Asp Gly Ile Glu Leu Thr Tyr
1               5                   10

<210> SEQ ID NO 38
<211> LENGTH: 32
<212> TYPE: PRT
<213> ORGANISM: Artificial Sequence
<220> FEATURE:
<223> OTHER INFORMATION: synthetic construct

<400> SEQUENCE: 38

Lys Lys Lys Lys Lys Lys Lys Lys Lys Lys Lys Lys Lys Lys Lys
1               5                   10                  15

Lys Lys Gly Gly Pro Leu Ala Glu Ile Asp Gly Ile Glu Leu Gly Ala
            20                  25                  30

<210> SEQ ID NO 39
<211> LENGTH: 27
<212> TYPE: PRT
<213> ORGANISM: Artificial Sequence
<220> FEATURE:
<223> OTHER INFORMATION: synthetic construct

<400> SEQUENCE: 39

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 40
<211> LENGTH: 5
<212> TYPE: PRT
<213> ORGANISM: Artificial Sequence
<220> FEATURE:
<223> OTHER INFORMATION: synthetic construct

<400> SEQUENCE: 40

Gly Gly Gly Gly Ser
1               5

<210> SEQ ID NO 41
<211> LENGTH: 8
<212> TYPE: PRT
<213> ORGANISM: Artificial Sequence
<220> FEATURE:
<223> OTHER INFORMATION: synthetic construct

<400> SEQUENCE: 41

Glu Ala Asn Gln Arg Ala Thr Lys
1               5

<210> SEQ ID NO 42
<211> LENGTH: 8
<212> TYPE: PRT
<213> ORGANISM: Artificial Sequence
<220> FEATURE:
<223> OTHER INFORMATION: synthetic construct

<400> SEQUENCE: 42

Gly Ala Ser Gln Phe Glu Thr Ser
1               5

<210> SEQ ID NO 43
<211> LENGTH: 8
```

```
<212> TYPE: PRT
<213> ORGANISM: Artificial Sequence
<220> FEATURE:
<223> OTHER INFORMATION: synthetic construct

<400> SEQUENCE: 43

Asp Thr Lys Lys Ala Val Lys Trp
 1               5

<210> SEQ ID NO 44
<211> LENGTH: 8
<212> TYPE: PRT
<213> ORGANISM: Artificial Sequence
<220> FEATURE:
<223> OTHER INFORMATION: synthetic construct

<400> SEQUENCE: 44

Arg Asp Gln Lys Leu Ser Glu Leu
 1               5

<210> SEQ ID NO 45
<211> LENGTH: 8
<212> TYPE: PRT
<213> ORGANISM: Artificial Sequence
<220> FEATURE:
<223> OTHER INFORMATION: synthetic construct

<400> SEQUENCE: 45

Gln Ile Asp Arg Ile Met Glu Lys
 1               5

<210> SEQ ID NO 46
<211> LENGTH: 8
<212> TYPE: PRT
<213> ORGANISM: Artificial Sequence
<220> FEATURE:
<223> OTHER INFORMATION: synthetic construct

<400> SEQUENCE: 46

Glu Arg Asp Gln Lys Leu Ser Glu
 1               5

<210> SEQ ID NO 47
<211> LENGTH: 8
<212> TYPE: PRT
<213> ORGANISM: Artificial Sequence
<220> FEATURE:
<223> OTHER INFORMATION: synthetic construct

<400> SEQUENCE: 47

Glu Thr Ser Ala Ala Lys Leu Lys
 1               5

<210> SEQ ID NO 48
<211> LENGTH: 8
<212> TYPE: PRT
<213> ORGANISM: Artificial Sequence
<220> FEATURE:
<223> OTHER INFORMATION: synthetic construct

<400> SEQUENCE: 48

Gly Ala Ser Gln Phe Glu Thr Ser
 1               5

<210> SEQ ID NO 49
<211> LENGTH: 13
<212> TYPE: PRT
```

<213> ORGANISM: Homo sapiens

<400> SEQUENCE: 49

Thr Arg Ile Asp Glu Ala Asn Gln Arg Ala Thr Lys Met
1               5                   10

<210> SEQ ID NO 50
<211> LENGTH: 15
<212> TYPE: PRT
<213> ORGANISM: Homo sapiens

<400> SEQUENCE: 50

Ser Asn Lys Thr Arg Ile Asp Glu Ala Asn Gln Arg Ala Thr Lys
1               5                   10                  15

<210> SEQ ID NO 51
<211> LENGTH: 16
<212> TYPE: PRT
<213> ORGANISM: Homo sapiens

<400> SEQUENCE: 51

Ser Asn Lys Thr Arg Ile Asp Glu Ala Asn Gln Arg Ala Thr Lys Met
1               5                   10                  15

<210> SEQ ID NO 52
<211> LENGTH: 17
<212> TYPE: PRT
<213> ORGANISM: Homo sapiens

<400> SEQUENCE: 52

Ser Asn Lys Thr Arg Ile Asp Glu Ala Asn Gln Arg Ala Thr Lys Met
1               5                   10                  15
Leu

<210> SEQ ID NO 53
<211> LENGTH: 17
<212> TYPE: PRT
<213> ORGANISM: Homo sapiens

<400> SEQUENCE: 53

Asp Ser Asn Lys Thr Arg Ile Asp Glu Ala Asn Gln Arg Ala Thr Lys
1               5                   10                  15
Met

<210> SEQ ID NO 54
<211> LENGTH: 18
<212> TYPE: PRT
<213> ORGANISM: Homo sapiens

<400> SEQUENCE: 54

Asp Ser Asn Lys Thr Arg Ile Asp Glu Ala Asn Gln Arg Ala Thr Lys
1               5                   10                  15
Met Leu

<210> SEQ ID NO 55
<211> LENGTH: 33
<212> TYPE: PRT
<213> ORGANISM: Mus musculus

<400> SEQUENCE: 55

Gln Asn Arg Gln Ile Asp Arg Ile Met Glu Lys Ala Asp Ser Asn Lys
1               5                   10                  15

```
Thr Arg Ile Asp Glu Ala Asn Gln Arg Ala Thr Lys Met Leu Gly Ser
            20                  25                  30

Gly

<210> SEQ ID NO 56
<211> LENGTH: 32
<212> TYPE: PRT
<213> ORGANISM: Homo sapiens

<400> SEQUENCE: 56

Gln Asn Pro Gln Ile Lys Arg Ile Thr Asp Lys Ala Asp Thr Asn Arg
1               5                   10                  15

Asp Arg Ile Asp Ile Ala Asn Ala Arg Ala Lys Lys Leu Ile Asp Ser
            20                  25                  30

<210> SEQ ID NO 57
<211> LENGTH: 32
<212> TYPE: PRT
<213> ORGANISM: Mus musculus

<400> SEQUENCE: 57

Gln Asn Gln Gln Ile Gln Lys Ile Thr Glu Lys Ala Asp Thr Asn Lys
1               5                   10                  15

Asn Arg Ile Asp Ile Ala Asn Thr Arg Ala Lys Lys Leu Ile Asp Ser
            20                  25                  30

<210> SEQ ID NO 58
<211> LENGTH: 34
<212> TYPE: PRT
<213> ORGANISM: Gallus gallus

<400> SEQUENCE: 58

Gln Asn Arg Gln Ile Asp Arg Ile Met Glu Lys Leu Ile Pro Ile Lys
1               5                   10                  15

Pro Gly Leu Met Lys Pro Thr Ser Val Gln Gln Arg Cys Ser Ala Val
            20                  25                  30

Val Lys

<210> SEQ ID NO 59
<211> LENGTH: 33
<212> TYPE: PRT
<213> ORGANISM: Carassius auratus

<400> SEQUENCE: 59

Gln Asn Arg Gln Ile Asp Arg Ile Met Asp Met Ala Asp Ser Asn Lys
1               5                   10                  15

Thr Arg Ile Asp Glu Ala Asn Gln Arg Ala Thr Lys Met Leu Gly Ser
            20                  25                  30

Gly

<210> SEQ ID NO 60
<211> LENGTH: 33
<212> TYPE: PRT
<213> ORGANISM: Carassius auratus

<400> SEQUENCE: 60

Gln Asn Arg Gln Ile Asp Arg Ile Met Glu Lys Ala Asp Ser Asn Lys
1               5                   10                  15

Thr Arg Ile Asp Glu Ala Asn Gln Arg Ala Thr Lys Met Leu Gly Ser
            20                  25                  30
```

Gly

<210> SEQ ID NO 61
<211> LENGTH: 30
<212> TYPE: PRT
<213> ORGANISM: Torpedo sp.

<400> SEQUENCE: 61

Gln Asn Ala Gln Val Asp Arg Ile Val Val Lys Gly Asp Met Asn Lys
1               5                   10                  15

Ala Arg Ile Asp Glu Ala Asn Lys His Ala Thr Lys Met Leu
            20                  25                  30

<210> SEQ ID NO 62
<211> LENGTH: 33
<212> TYPE: PRT
<213> ORGANISM: Strongylocentrotus purpuratus

<400> SEQUENCE: 62

Gln Asn Ser Gln Val Gly Arg Ile Thr Ser Lys Ala Glu Ser Asn Glu
1               5                   10                  15

Gly Arg Ile Asn Ser Ala Asp Lys Arg Ala Lys Asn Ile Leu Arg Asn
            20                  25                  30

Lys

<210> SEQ ID NO 63
<211> LENGTH: 31
<212> TYPE: PRT
<213> ORGANISM: Caenorhabditis elegans

<400> SEQUENCE: 63

Gln Asn Arg Gln Leu Asp Arg Ile His Asp Lys Gln Ser Asn Glu Val
1               5                   10                  15

Arg Val Glu Ser Ala Asn Lys Arg Ala Lys Asn Leu Ile Thr Lys
            20                  25                  30

<210> SEQ ID NO 64
<211> LENGTH: 31
<212> TYPE: PRT
<213> ORGANISM: Drosophila melanogaster

<400> SEQUENCE: 64

Gln Asn Arg Gln Ile Asp Arg Ile Asn Arg Lys Gly Glu Ser Asn Glu
1               5                   10                  15

Ala Arg Ile Ala Val Ala Asn Gln Arg Ala His Gln Leu Leu Lys
            20                  25                  30

<210> SEQ ID NO 65
<211> LENGTH: 32
<212> TYPE: PRT
<213> ORGANISM: Hirudinida sp.

<400> SEQUENCE: 65

Gln Asn Arg Gln Val Asp Arg Ile Asn Asn Lys Met Thr Ser Asn Gln
1               5                   10                  15

Leu Arg Ile Ser Asp Ala Asn Lys Arg Ala Ser Lys Leu Leu Lys Glu
            20                  25                  30

<210> SEQ ID NO 66
<211> LENGTH: 15
<212> TYPE: PRT
<213> ORGANISM: Artificial Sequence

```
<220> FEATURE:
<223> OTHER INFORMATION: synthetic construct

<400> SEQUENCE: 66

Ser Asn Lys Thr Arg Ile Asp Glu Ala Asn Gln Arg Ala Thr Lys
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: synthetic construct

<400> SEQUENCE: 67

Ser Asn Lys Thr Arg Ile Asp Glu Ala Asn Gln Arg Ala Thr Lys Met
1               5                   10                  15

<210> SEQ ID NO 68
<211> LENGTH: 17
<212> TYPE: PRT
<213> ORGANISM: Artificial Sequence
<220> FEATURE:
<223> OTHER INFORMATION: synthetic construct

<400> SEQUENCE: 68

Ser Asn Lys Thr Arg Ile Asp Glu Ala Asn Gln Arg Ala Thr Lys Met
1               5                   10                  15

Leu

<210> SEQ ID NO 69
<211> LENGTH: 17
<212> TYPE: PRT
<213> ORGANISM: Artificial Sequence
<220> FEATURE:
<223> OTHER INFORMATION: synthetic construct

<400> SEQUENCE: 69

Ser Asn Lys Thr Arg Ile Asp Glu Ala Asn Gln Arg Ala Thr Lys Ala
1               5                   10                  15

Leu

<210> SEQ ID NO 70
<211> LENGTH: 17
<212> TYPE: PRT
<213> ORGANISM: Artificial Sequence
<220> FEATURE:
<223> OTHER INFORMATION: synthetic construct
<221> NAME/KEY: MOD_RES
<222> LOCATION: 16
<223> OTHER INFORMATION: Xaa = Nle

<400> SEQUENCE: 70

Ser Asn Lys Thr Arg Ile Asp Glu Ala Asn Gln Arg Ala Thr Lys Xaa
1               5                   10                  15

Leu

<210> SEQ ID NO 71
<211> LENGTH: 17
<212> TYPE: PRT
<213> ORGANISM: Artificial Sequence
<220> FEATURE:
<223> OTHER INFORMATION: synthetic construct

<400> SEQUENCE: 71
```

Ser Asn Lys Thr Arg Ile Asp Glu Ala Asn Gln Arg Ala Thr Ala Met
1               5                   10                  15

Leu

<210> SEQ ID NO 72
<211> LENGTH: 17
<212> TYPE: PRT
<213> ORGANISM: Artificial Sequence
<220> FEATURE:
<223> OTHER INFORMATION: synthetic construct

<400> SEQUENCE: 72

Ser Asn Lys Thr Arg Ile Asp Glu Ala Asn Gln Arg Ala Ser Lys Met
1               5                   10                  15

Leu

<210> SEQ ID NO 73
<211> LENGTH: 17
<212> TYPE: PRT
<213> ORGANISM: Artificial Sequence
<220> FEATURE:
<223> OTHER INFORMATION: synthetic construct
<221> NAME/KEY: MOD_RES
<222> LOCATION: 14
<223> OTHER INFORMATION: Xaa = Abu

<400> SEQUENCE: 73

Ser Asn Lys Thr Arg Ile Asp Glu Ala Asn Gln Arg Ala Xaa Lys Met
1               5                   10                  15

Leu

<210> SEQ ID NO 74
<211> LENGTH: 17
<212> TYPE: PRT
<213> ORGANISM: Artificial Sequence
<220> FEATURE:
<223> OTHER INFORMATION: synthetic construct
<221> NAME/KEY: MOD_RES
<222> LOCATION: 13
<223> OTHER INFORMATION: Xaa = Abu

<400> SEQUENCE: 74

Ser Asn Lys Thr Arg Ile Asp Glu Ala Asn Gln Arg Xaa Thr Lys Met
1               5                   10                  15

Leu

<210> SEQ ID NO 75
<211> LENGTH: 17
<212> TYPE: PRT
<213> ORGANISM: Artificial Sequence
<220> FEATURE:
<223> OTHER INFORMATION: synthetic construct

<400> SEQUENCE: 75

Ser Asn Lys Thr Arg Ile Asp Glu Ala Asn Ala Arg Ala Thr Lys Met
1               5                   10                  15

Leu

<210> SEQ ID NO 76
<211> LENGTH: 17
<212> TYPE: PRT
<213> ORGANISM: Artificial Sequence
<220> FEATURE:
<223> OTHER INFORMATION: synthetic construct
<221> NAME/KEY: MOD_RES
<222> LOCATION: 11
<223> OTHER INFORMATION: Xaa = Abu

<400> SEQUENCE: 76

Ser Asn Lys Thr Arg Ile Asp Glu Ala Asn Xaa Arg Ala Thr Lys Met
1               5                   10                  15

Leu

<210> SEQ ID NO 77
<211> LENGTH: 17
<212> TYPE: PRT
<213> ORGANISM: Artificial Sequence
<220> FEATURE:
<223> OTHER INFORMATION: synthetic construct

<400> SEQUENCE: 77

Ser Asn Lys Thr Arg Ile Asp Glu Ala Asn Asn Arg Ala Thr Lys Met
1               5                   10                  15

Leu

<210> SEQ ID NO 78
<211> LENGTH: 17
<212> TYPE: PRT
<213> ORGANISM: Artificial Sequence
<220> FEATURE:
<223> OTHER INFORMATION: synthetic construct

<400> SEQUENCE: 78

Ser Asn Lys Thr Arg Ile Asp Glu Ala Ala Gln Arg Ala Thr Lys Met
1               5                   10                  15

Leu

<210> SEQ ID NO 79
<211> LENGTH: 17
<212> TYPE: PRT
<213> ORGANISM: Artificial Sequence
<220> FEATURE:
<223> OTHER INFORMATION: synthetic construct
<221> NAME/KEY: MOD_RES
<222> LOCATION: 9
<223> OTHER INFORMATION: Xaa = Abu

<400> SEQUENCE: 79

Ser Asn Lys Thr Arg Ile Asp Glu Xaa Asn Gln Arg Ala Thr Lys Met
1               5                   10                  15

Leu

<210> SEQ ID NO 80
<211> LENGTH: 17
<212> TYPE: PRT
<213> ORGANISM: Artificial Sequence
<220> FEATURE:
<223> OTHER INFORMATION: synthetic construct

<400> SEQUENCE: 80

Ser Asn Lys Thr Arg Ile Asp Gln Ala Asn Gln Arg Ala Thr Lys Met
1               5                   10                  15

Leu

<210> SEQ ID NO 81
<211> LENGTH: 17
<212> TYPE: PRT
<213> ORGANISM: Artificial Sequence
<220> FEATURE:

-continued

<223> OTHER INFORMATION: synthetic construct

<400> SEQUENCE: 81

Ser Asn Lys Thr Arg Ile Asn Glu Ala Asn Gln Arg Ala Thr Lys Met
1               5                   10                  15

Leu

<210> SEQ ID NO 82
<211> LENGTH: 40
<212> TYPE: PRT
<213> ORGANISM: Homo sapiens

<400> SEQUENCE: 82

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Ser Ser Ala Ala
            20                  25                  30

Lys Leu Lys Arg Lys Tyr Trp Trp
        35                  40

<210> SEQ ID NO 83
<211> LENGTH: 40
<212> TYPE: PRT
<213> ORGANISM: Bos taurus

<400> SEQUENCE: 83

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Thr Ser Ala Ala
            20                  25                  30

Lys Leu Lys Arg Lys Tyr Trp Trp
        35                  40

<210> SEQ ID NO 84
<211> LENGTH: 40
<212> TYPE: PRT
<213> ORGANISM: Rattus sp.

<400> SEQUENCE: 84

Asp Lys Val Leu Glu Arg Asp Gln Lys Leu Ser Glu Leu Asp Asp Arg
1               5                   10                  15

Ala Asp Ala Leu Gln Ala Gly Ala Ser Val Phe Glu Ser Ser Ala Ala
            20                  25                  30

Lys Leu Lys Arg Lys Tyr Trp Trp
        35                  40

<210> SEQ ID NO 85
<211> LENGTH: 40
<212> TYPE: PRT
<213> ORGANISM: Rattus sp.

<400> SEQUENCE: 85

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Thr Ser Ala Ala
            20                  25                  30

Lys Leu Lys Arg Lys Tyr Trp Trp
        35                  40

<210> SEQ ID NO 86

<211> LENGTH: 40
<212> TYPE: PRT
<213> ORGANISM: Rattus sp.

<400> SEQUENCE: 86

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Thr Ser Ala Ala
            20                  25                  30

Lys Leu Lys Arg Lys Tyr Trp Trp
        35                  40

<210> SEQ ID NO 87
<211> LENGTH: 40
<212> TYPE: PRT
<213> ORGANISM: Rattus sp.

<400> SEQUENCE: 87

Asp Leu Val Ala Gln Arg Gly Glu Arg Leu Glu Leu Leu Ile Asp Lys
1               5                   10                  15

Thr Glu Asn Leu Val Asp Ser Ser Val Thr Phe Lys Thr Thr Ser Arg
            20                  25                  30

Asn Leu Ala Arg Ala Met Cys Met
        35                  40

<210> SEQ ID NO 88
<211> LENGTH: 32
<212> TYPE: PRT
<213> ORGANISM: Gallus gallus

<400> SEQUENCE: 88

Glu Arg Asp Gln Lys Leu Ser Glu Leu Asp Asp Arg Ala Asp Ala Leu
1               5                   10                  15

Gln Ala Gly Ala Ser Val Phe Glu Ser Ser Ala Ala Lys Leu Lys Arg
            20                  25                  30

<210> SEQ ID NO 89
<211> LENGTH: 32
<212> TYPE: PRT
<213> ORGANISM: Gallus gallus

<400> SEQUENCE: 89

Glu Arg Asp Gln Lys Leu Ser Glu Leu Asp Asp Arg Ala Asp Ala Leu
1               5                   10                  15

Gln Ala Gly Ala Ser Gln Phe Glu Thr Ser Ala Ala Lys Leu Lys Arg
            20                  25                  30

<210> SEQ ID NO 90
<211> LENGTH: 40
<212> TYPE: PRT
<213> ORGANISM: Torpedo sp.

<400> SEQUENCE: 90

Asp Lys Val Leu Glu Arg Asp Gln Lys Leu Ser Glu Leu Asp Asp Arg
1               5                   10                  15

Ala Asp Ala Leu Gln Ala Gly Ala Ser Gln Phe Glu Ser Ser Ala Ala
            20                  25                  30

Lys Leu Lys Arg Lys Tyr Trp Trp
        35                  40

<210> SEQ ID NO 91

<211> LENGTH: 40
<212> TYPE: PRT
<213> ORGANISM: Strongylocentrotus purpuratus

<400> SEQUENCE: 91

Asp Lys Val Leu Asp Arg Asp Gln Ala Leu Ser Val Leu Asp Arg
1               5                   10                  15

Ala Asp Ala Leu Gln Gln Gly Ala Ser Gln Phe Glu Thr Asn Ala Gly
            20                  25                  30

Lys Leu Lys Arg Lys Tyr Trp Trp
        35                  40

<210> SEQ ID NO 92
<211> LENGTH: 40
<212> TYPE: PRT
<213> ORGANISM: Aplysia sp.

<400> SEQUENCE: 92

Glu Lys Val Leu Asp Arg Asp Gln Lys Ile Ser Gln Leu Asp Arg
1               5                   10                  15

Ala Glu Ala Leu Gln Ala Gly Ala Ser Gln Phe Glu Ala Ser Ala Gly
            20                  25                  30

Lys Leu Lys Arg Lys Tyr Trp Trp
        35                  40

<210> SEQ ID NO 93
<211> LENGTH: 40
<212> TYPE: PRT
<213> ORGANISM: Teuthoida

<400> SEQUENCE: 93

Asp Lys Val Leu Glu Arg Asp Ser Lys Ile Ser Glu Leu Asp Arg
1               5                   10                  15

Ala Asp Ala Leu Gln Ala Gly Ala Ser Gln Phe Glu Ala Ser Ala Gly
            20                  25                  30

Lys Leu Lys Arg Lys Phe Trp Trp
        35                  40

<210> SEQ ID NO 94
<211> LENGTH: 40
<212> TYPE: PRT
<213> ORGANISM: Caenorhabditis elegans

<400> SEQUENCE: 94

Asn Lys Val Met Glu Arg Asp Val Gln Leu Asn Ser Leu Asp His Arg
1               5                   10                  15

Ala Glu Val Leu Gln Asn Gly Ala Ser Gln Phe Gln Asn Ser Ser Arg
            20                  25                  30

Glu Leu Lys Arg Gln Tyr Trp Trp
        35                  40

<210> SEQ ID NO 95
<211> LENGTH: 40
<212> TYPE: PRT
<213> ORGANISM: Drosophila melanogaster

<400> SEQUENCE: 95

Glu Lys Val Leu Glu Arg Asp Gln Lys Leu Ser Glu Leu Gly Glu Arg
1               5                   10                  15

Ala Asp Gln Leu Glu Gln Gly Ala Ser Gln Ser Glu Gln Gln Ala Gly
            20                  25                  30

```
Lys Leu Lys Arg Lys Gln Trp Trp
        35                  40

<210> SEQ ID NO 96
<211> LENGTH: 40
<212> TYPE: PRT
<213> ORGANISM: Drosophila melanogaster

<400> SEQUENCE: 96

Glu Lys Val Leu Glu Arg Asp Ser Lys Leu Ser Glu Leu Asp Asp Arg
1               5                   10                  15

Ala Asp Ala Leu Gln Gln Gly Ala Ser Gln Phe Glu Gln Gln Ala Gly
            20                  25                  30

Lys Leu Lys Arg Lys Phe Trp Leu
        35                  40

<210> SEQ ID NO 97
<211> LENGTH: 40
<212> TYPE: PRT
<213> ORGANISM: Hirudinida

<400> SEQUENCE: 97

Asp Lys Val Leu Glu Lys Asp Gln Lys Leu Ala Glu Leu Asp Gly Arg
1               5                   10                  15

Ala Asp Ala Leu Gln Ala Gly Ala Ser Gln Phe Glu Ala Ser Ala Gly
            20                  25                  30

Lys Leu Lys Arg Lys Phe Trp Trp
        35                  40

<210> SEQ ID NO 98
<211> LENGTH: 18
<212> TYPE: PRT
<213> ORGANISM: Homo sapiens

<400> SEQUENCE: 98

Glu Arg Ala Val Ser Asp Thr Lys Lys Ala Val Lys Tyr Gln Ser Lys
1               5                   10                  15

Ala Arg

<210> SEQ ID NO 99
<211> LENGTH: 18
<212> TYPE: PRT
<213> ORGANISM: Bos taurus

<400> SEQUENCE: 99

Glu Arg Ala Val Ser Asp Thr Lys Lys Ala Val Lys Tyr Gln Ser Lys
1               5                   10                  15

Ala Arg

<210> SEQ ID NO 100
<211> LENGTH: 18
<212> TYPE: PRT
<213> ORGANISM: Rattus sp.

<400> SEQUENCE: 100

Glu His Ala Lys Glu Glu Thr Lys Lys Ala Ile Lys Tyr Gln Ser Lys
1               5                   10                  15

Ala Arg

<210> SEQ ID NO 101
```

```
<211> LENGTH: 18
<212> TYPE: PRT
<213> ORGANISM: Rattus sp.

<400> SEQUENCE: 101

Glu Lys Ala Arg Asp Glu Thr Arg Lys Ala Met Lys Tyr Gln Gly Gln
 1               5                  10                  15

Ala Arg

<210> SEQ ID NO 102
<211> LENGTH: 18
<212> TYPE: PRT
<213> ORGANISM: Rattus sp.

<400> SEQUENCE: 102

Glu Arg Gly Gln Glu His Val Lys Ile Ala Leu Glu Asn Gln Lys Lys
 1               5                  10                  15

Ala Arg

<210> SEQ ID NO 103
<211> LENGTH: 18
<212> TYPE: PRT
<213> ORGANISM: Gallus gallus

<400> SEQUENCE: 103

Val Pro Glu Val Phe Val Thr Lys Ser Ala Val Met Tyr Gln Cys Lys
 1               5                  10                  15

Ser Arg

<210> SEQ ID NO 104
<211> LENGTH: 18
<212> TYPE: PRT
<213> ORGANISM: Strongylocentrotus purpuratus

<400> SEQUENCE: 104

Val Arg Arg Gln Asn Asp Thr Lys Lys Ala Val Lys Tyr Gln Ser Lys
 1               5                  10                  15

Ala Arg

<210> SEQ ID NO 105
<211> LENGTH: 18
<212> TYPE: PRT
<213> ORGANISM: Aplysia sp.

<400> SEQUENCE: 105

Glu Thr Ala Lys Met Asp Thr Lys Lys Ala Val Lys Tyr Gln Ser Lys
 1               5                  10                  15

Ala Arg

<210> SEQ ID NO 106
<211> LENGTH: 18
<212> TYPE: PRT
<213> ORGANISM: Teuthoida sp.

<400> SEQUENCE: 106

Glu Thr Ala Lys Val Asp Thr Lys Lys Ala Val Lys Tyr Gln Ser Lys
 1               5                  10                  15

Ala Arg

<210> SEQ ID NO 107
<211> LENGTH: 18
```

```
<212> TYPE: PRT
<213> ORGANISM: Drosophila melanogaster

<400> SEQUENCE: 107

Gln Thr Ala Thr Gln Asp Thr Lys Lys Ala Leu Lys Tyr Gln Ser Lys
1               5                   10                  15

Ala Arg

<210> SEQ ID NO 108
<211> LENGTH: 18
<212> TYPE: PRT
<213> ORGANISM: Hirudinida

<400> SEQUENCE: 108

Glu Thr Ala Ala Ala Asp Thr Lys Lys Ala Met Lys Tyr Gln Ser Ala
1               5                   10                  15

Ala Arg

<210> SEQ ID NO 109
<211> LENGTH: 206
<212> TYPE: PRT
<213> ORGANISM: Rattus sp.

<400> SEQUENCE: 109

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Glu Arg Ile Glu Glu Gly Met
        50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
                100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205
```

CELL COMPOSITIONS USEFUL FOR CELL-BASED FRET ASSAYS FOR CLOSTRIDIAL TOXINS

This application is a divisional of 11/621,212 Jan. 9, 2007 ABN which is a divisional of 10/261,161 Sep. 27, 2002 now U.S. Pat. No. 7,183,066.

BACKGROUND OF THE INVENTION

1. Field of the Invention

The present invention relates generally to fluorescence resonance energy transfer and protease assays and, more specifically, to cell-based methods for assaying for clostridial toxin activity.

2. Background Information

The neuroparalytic syndrome of tetanus and the rare but potentially fatal disease, botulism, are caused by neurotoxins produced by bacteria of the genus *Clostridium*. These clostridial neurotoxins are highly potent and specific poisons of neural cells, with the human lethal dose of the botulinum toxins on the order of nanograms. Thus, the presence of even minute levels of botulinum toxins in foodstuffs represents a public health hazard that must be avoided through rigorous testing.

However, in spite of their potentially deleterious effects, low controlled doses of botulinum neurotoxins have been successfully used as therapeutics and for some cosmetic applications. In particular, botulinum toxins have been used in the therapeutic management of a variety of focal and segmental dystonias, strabismus, and other conditions in which a reversible depression of a cholinergic nerve terminal activity is desired. Established therapeutic uses of botulinum neurotoxins in humans include, without limitation, blepharospasm, hemifacial spasm, laringeal dysphonia, focal hyperhidrosis, hypersalivation, oromandibular dystonia, cervical dystonia, torticollis, strabismus, limbs dystonia, occupational cramps and myokymia (Rossetto et al., *Toxicon* 39:27-41 (2001)). As an example, intramuscular injection of spastic tissue with small quantities of botulinum neurotoxin A has been used effectively to treat spasticity due to brain injury, spinal cord injury, stroke, multiple sclerosis and cerebral palsy. Additional possible clinical uses of clostridial neurotoxins currently are being investigated.

Given the potential danger associated with small quantities of botulinum toxins in foodstuffs and the need to prepare accurate pharmaceutical formulations, assays for botulinum neurotoxins presently are employed in the food and pharmaceutical industries. The food industry requires assays for the botulinum neurotoxins to validate new food packaging methods and to ensure food safety. The growing clinical use of the botulinum toxins necessitates accurate assays for botulinum neurotoxin activity for product formulation as well as quality control. In both industries, a mouse lethality test currently is the only acceptable assay for botulinum neurotoxin activity.

Unfortunately, the mouse lethality assay suffers from several drawbacks: cost due to the large numbers of laboratory animals required; lack of specificity; the potential for inaccuracy unless large animal groups are used; and the necessary sacrifice of animal life. Thus, there is a need for a new method that can complement and reduce the need for the mouse lethality assay. In addition to measuring toxin proteolytic activity, such a surrogate method also should require cellular uptake of the toxin and delivery of the toxin light chain into the cell cytosol. The present invention satisfies this need by providing novel cell-based assays for clostridial toxin activity and also provides related advantages.

SUMMARY OF THE INVENTION

The present invention provides a substrate composition that includes a delivery agent and a clostridial toxin substrate containing a donor fluorophore; an acceptor having an absorbance spectrum overlapping the emission spectrum of the donor fluorophore; and a clostridial toxin recognition sequence containing a cleavage site that intervenes between the donor fluorophore and the acceptor, where resonance energy transfer is exhibited between the donor fluorophore and the acceptor under the appropriate conditions. In a substrate composition of the invention, the delivery agent can be, for example, covalently linked to the clostridial toxin substrate and further can be, for example, a protein, peptide or peptidomimetic. In one embodiment, the substrate composition is a chimeric protein, peptide or peptidomimetic in which the delivery agent is operatively fused to the clostridial toxin substrate. Such a chimeric substrate composition can be, for example, a peptide or peptidomimetic having a length of at most 50 or 100 residues.

A variety of delivery agents can be covalently linked to a clostridial toxin substrate in a substrate composition of the invention including, without limitation, an antennapedia protein or active fragment thereof, such as an active fragment having the amino acid sequence RQIKIWFQNRRMKWKK (SEQ ID NO: 1); an HIV TAT protein or active fragment thereof, such as an active fragment having the amino acid sequence YGRKKRRQRRR (SEQ ID NO: 2); and a herpes simplex virus VP22 protein or active fragment thereof, such as a herpes simplex virus VP22 protein having the amino acid sequence SEQ ID NO: 3, or active fragment thereof.

The invention also provides a substrate composition in which the delivery agent is non-covalently associated with the clostridial toxin substrate. Exemplary delivery agents that can be non-covalently associated with a clostridial toxin substrate include, without limitation, Chariot™ and MPG peptides.

A variety of clostridial toxin substrates are useful in the substrate compositions of the invention. Such a clostridial toxin substrate can be, for example, a botulinum toxin substrate containing a botulinum toxin recognition sequence or a tetanus toxin substrate containing a tetanus toxin recognition sequence. In one embodiment, the invention provides a substrate composition containing, in part, a BoNT/A substrate that includes a BoNT/A recognition sequence. Such a BoNT/A substrate can include, for example, at least six consecutive residues of SNAP-25, the six consecutive residues containing Gln-Arg, or a peptidomimetic thereof. In another embodiment, the invention provides a substrate composition that includes a BoNT/B substrate containing a BoNT/B recognition sequence. BoNT/B substrates useful in the substrate compositions of the invention include, without limitation, those having at least six consecutive residues of VAMP, the six consecutive residues containing Gln-Phe, or a peptidomimetic thereof. In a further embodiment, the invention provides a BoNT/C1 substrate containing a BoNT/C1 recognition sequence; BoNT/C1 substrates useful in the invention encompass those having at least six consecutive residues of syntaxin, the six consecutive residues containing Lys-Ala, or a peptidomimetic thereof, and those including at least six consecutive residues of SNAP-25, the six consecutive residues containing Arg-Ala, or a peptidomimetic thereof. In another embodiment, the invention provides a BoNT/D substrate containing a BoNT/D recognition sequence. A variety of BoNT/D substrates are useful in the substrate compositions of the invention including, yet not limited to, BoNT/D substrates containing at least six consecutive residues of VAMP, the six consecutive residues containing Lys-Leu, or a peptidomimetic thereof.

In a further embodiment, the invention provides a substrate composition that includes, in part, a BoNT/E substrate containing a BoNT/E recognition sequence. Such a BoNT/E substrate can have, for example, at least six consecutive residues of SNAP-25, the six consecutive residues containing Arg-Ile, or a peptidomimetic thereof. In an additional embodiment, there is provided herein a substrate composition which includes a BoNT/F substrate containing a BoNT/F recognition sequence. BoNT/F substrates useful in the compositions of the invention can have, for example, at least six consecutive residues of VAMP, the six consecutive residues containing Gln-Lys, or a peptidomimetic thereof. In still a further embodiment, the invention provides a substrate composition that contains, in part, a BoNT/G substrate having a BoNT/G recognition sequence. Useful BoNT/G substrates include, yet are not limited to, those having at least six consecutive residues of VAMP, the six consecutive residues containing Ala-Ala, or a peptidomimetic thereof. In a further embodiment, the present invention provides a substrate composition that includes, in part, a TeNT substrate containing a TeNT recognition sequence. A variety of TeNT substrates are useful in the invention including those having at least six consecutive residues of VAMP, the six consecutive residues containing Gln-Phe, or a peptidomimetic thereof.

A variety of donor fluorophores and acceptors are useful in the substrate compositions of the invention. As non-limiting examples, donor fluorophores useful in the invention include Alexa Fluor®-488, DABCYL and BODIPY®. Acceptors useful in the invention include non-fluorescent acceptors as well as acceptor fluorophores; in one embodiment, the acceptor is an acceptor fluorophore having a fluorescence lifetime of at least 1 microsecond. In other embodiments, the invention provides a substrate composition in which the acceptor is EDANS, QSY 7®, or tetramethylrhodamine.

Further provided herein is a cell containing a clostridial toxin substrate that includes a donor fluorophore; an acceptor having an absorbance spectrum overlapping the emission spectrum of the donor fluorophore; and a clostridial toxin recognition sequence containing a cleavage site that intervenes between the donor fluorophore and the acceptor, where resonance energy transfer is exhibited between the donor fluorophore and the acceptor under the appropriate conditions. In one embodiment, the cell is a transfected cell. In another embodiment, the cell is a stably transfected cell. A variety of cells are useful in the invention including, without limitation, primary cells; established cells; human cells; neuronal cells such as primary neurons, established neurons and human neurons; and non-neuronal cells such as pancreatic acinar cells. Neurons useful in the invention include central nervous system (CNS) neurons and peripheral neurons; as non-limiting examples, a neuron useful in the invention can be a neuroblastoma, spinal cord neuron, dorsal root ganglion neuron, cerebral cortex neuron, cerebellar neuron, hippocampal neuron or motor neuron.

Further provided herein is a cell which includes a nucleic acid molecule encoding a clostridial toxin substrate that includes a donor fluorophore; an acceptor having an absorbance spectrum overlapping the emission spectrum of the donor fluorophore; and a clostridial toxin recognition sequence containing a cleavage site that intervenes between the donor fluorophore and the acceptor, where resonance energy transfer is exhibited between the donor fluorophore and the acceptor under the appropriate conditions.

Any of a variety of cells can be useful, including, but not limited to, human cells, neuronal cells and non-neuronal cells. Such a cell can be prepared, for example, by stable transfection of a nucleic acid molecule encoding a clostridial toxin substrate. The nucleic acid molecule encoding a clostridial toxin substrate can be linked, for example, to a regulatory element such as a constitutive regulatory element or inducible regulatory element. A variety of inducible regulatory elements are useful in the invention, including, without limitation, tetracycline regulated regulatory elements and ecdysone inducible regulatory elements. Genetically encoded donor fluorophores and acceptors useful in the invention include green fluorescence protein (GFP) and others disclosed herein below and known in the art.

The present invention also provides a method of determining clostridial toxin activity by (a) contacting with a sample a cell containing a clostridial toxin substrate that includes a donor fluorophore; an acceptor having an absorbance spectrum overlapping the emission spectrum of the donor fluorophore; and a clostridial toxin recognition sequence containing a cleavage site that intervenes between the donor fluorophore and the acceptor, where resonance energy transfer is exhibited between the donor fluorophore and the acceptor under the appropriate conditions; (b) exciting the donor fluorophore; and (c) determining resonance energy transfer of the contacted cell relative to a control cell, where a difference in resonance energy transfer of the contacted cell as compared to the control cell is indicative of clostridial toxin activity.

A clostridial toxin substrate useful in a method of the invention can be a botulinum toxin substrate of any serotype or a tetanus toxin substrate.

Thus, a method of the invention can be practiced, for example, with a BoNT/A substrate containing a BoNT/A recognition sequence; a BoNT/B substrate containing a BoNT/B recognition sequence; a BoNT/C1 substrate containing a BoNT/C1 recognition sequence; a BoNT/D substrate containing a BoNT/D recognition sequence; a BoNT/E substrate containing a BoNT/E recognition sequence; a BoNT/F substrate containing a BoNT/F recognition sequence; a BoNT/G substrate containing a BoNT/G recognition sequence; or a TeNT toxin substrate containing a TeNT recognition sequence.

A variety of samples can be assayed for clostridial toxin activity according to a method of the invention. Such samples include, without limitation, crude cell lysates; isolated clostridial toxins; formulated clostridial toxin products such as BOTOX-; and foodstuffs.

A variety of means can be used to determine resonance energy transfer in a method of the invention. In one embodiment, a method of the invention includes the step of detecting donor fluorescence intensity of the contacted cell, where increased donor fluorescence intensity of the contacted cell as compared to the control cell is indicative of clostridial toxin activity. In another embodiment, a method of the invention includes the step of detecting acceptor fluorescence intensity of the contacted cell, where decreased acceptor fluorescence intensity of the contacted cell as compared to the control cell is indicative of clostridial toxin activity. In a further embodiment, a method of the invention includes the step of detecting an acceptor emission maximum and a donor fluorophore emission maximum of the contacted cell, where a shift in emission maxima from near the acceptor emission maximum to near the donor fluorophore emission maximum is indicative of clostridial toxin activity. In yet a further embodiment, a method of the invention includes the step of detecting the ratio of fluorescence amplitudes near an acceptor emission maximum to the fluorescence amplitudes near a donor fluorophore emission maximum of the contacted cell, where a decreased ratio in the contacted cell as compared to the control cell is indicative of clostridial toxin activity. In still another embodiment, a method of the invention includes the step of detecting the excited state lifetime of the donor fluorophore in the contacted cell, where an increased donor fluorophore excited state lifetime in the contacted cell as compared to the control cell is indicative of clostridial toxin activity. If desired, the step of determining resonance energy transfer can be repeated at one or more later time intervals. In addition, the conditions suitable for clostridial toxin activity can be selected, if desired, such that the assay is linear.

BRIEF DESCRIPTION OF THE DRAWINGS

Figure 3:
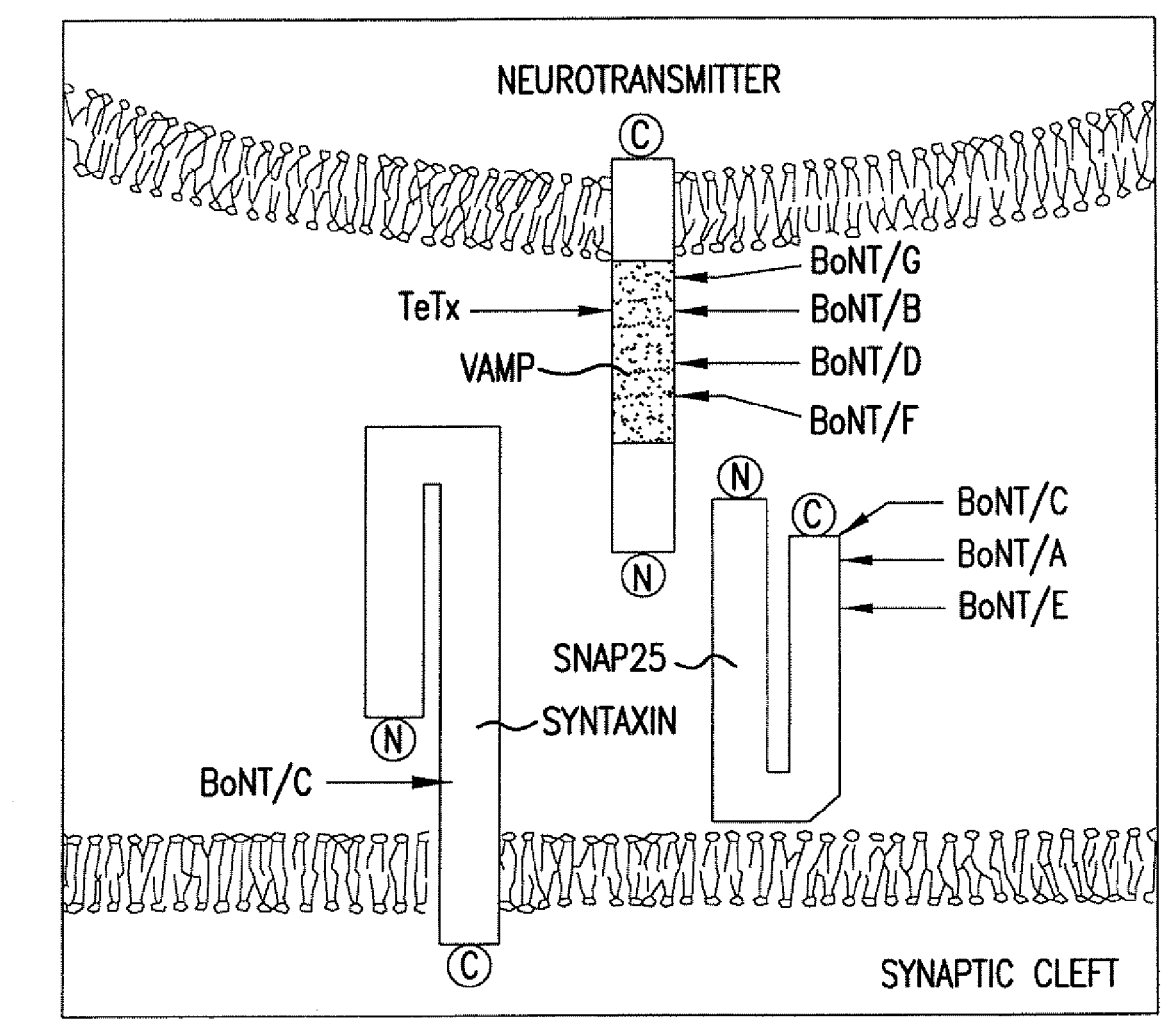

FIG. 3 shows the subcellular localization at the plasma membrane and sites of cleavage of SNAP-25, VAMP and syntaxin. VAMP is bound to synaptic vesicle membrane, whereas SNAP-25 and syntaxin are bound to the target plasma membrane. BoNT/A and /E cleave SNAP-25 close to the carboxy-terminus, releasing nine or 26 residues, respectively. BoNT/B, /D, /F, /G and TeNT act on the conserved central portion of VAMP (dotted) and release the amino-terminal portion of VAMP into the cytosol. BoNT/C1 cleaves SNAP-25 close to the carboxy-terminus as well as cleaving syntaxin at a single site near the cytosolic membrane surface. The action of BoNT/B, /C1, /D, /F, /G and TeNT results in release of a large portion of the cytosolic domain of VAMP or syntaxin, while only a small portion of SNAP-25 is released by selective proteolysis by BoNT/A, /C1 or /E.

FIG. 5 shows an alignment of various SNAP-25 proteins and their BoNT/E, BoNT/A and BoNT/C1 cleavage sites. Human SNAP-25 (SEQ ID NO: 4; GenBank accession g4507099; see, also, related human SNAP-25 sequence g2135800); mouse SNAP-25 (SEQ ID NO: 5; GenBank accession G6755588); Drosophila SNAP-25 (SEQ ID NO: 6; GenBank accession g548941); goldfish SNAP-25 (SEQ ID NO: 7; GenBank accession g2133923); sea urchin SNAP-25 (SEQ ID NO: 8; GenBank accession g2707818) and chicken SNAP-25 (SEQ ID NO: 9; GenBank accession g481202) are depicted.

FIG. 6 shows an alignment of various VAMP proteins and their BoNT/F, BoNT/D, BoNT/B, TeNT and BoNT/G cleavage sites. Human VAMP-1 (SEQ ID NO: 10; GenBank accession g135093); human VAMP-2 (SEQ ID NO: 11; GenBank accession g135094); mouse VAMP-2 (SEQ ID NO: 12; GenBank accession g2501081); bovine VAMP (SEQ ID NO: 13; GenBank accession g89782); frog VAMP (SEQ ID NO: 14; GenBank accession g6094391); and sea urchin VAMP (SEQ ID NO: 15; GenBank accession g5031415) are depicted.

FIG. 7 shows an alignment of various syntaxin proteins and their BoNT/C1 cleavage sites. Human syntaxin 1A (SEQ ID NO: 16; GenBank accession g 15079184), human syntaxin 1B2 (SEQ ID NO: 17; GenBank accession g15072437), mouse syntaxin 1A (SEQ ID NO: 18; GenBank accession g15011853), Drosophila syntaxin 1A (SEQ ID NO: 19; GenBank accession g2501095); C. elegans syntaxin A (SEQ ID NO: 20; GenBank accession g7511662) and sea urchin syntaxin (SEQ ID NO: 21; GenBank accession g13310402) are depicted.

DETAILED DESCRIPTION OF THE INVENTION

Figure 1:
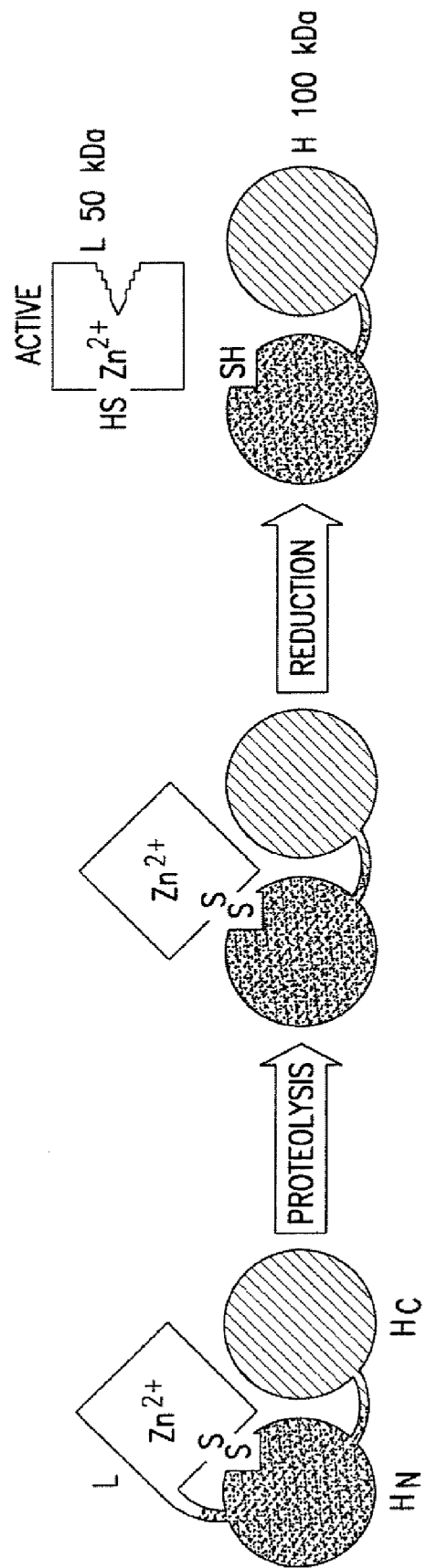
FIG. 1 shows a schematic of the deduced structure and postulated mechanism of activation of clostridial neurotoxins. Toxins can be produced as an inactive single polypeptide chain of 150 kDa, composed of three 50 kDa domains connected by loops. Selective proteolytic cleavage activates the toxins by generating two disulfide-linked chains: the L chain of 50 kDa and the H chain of 100 kDa, which is made up of two domains denoted $H_N$ and $H_C$. The three domains play distinct roles: the C-terminal domain of the heavy chain ($H_C$) functions in cell binding while the N-terminal domain of the heavy chain ($H_N$) permits translocation from endosome to cell cytoplasm. Following reduction of the disulfide linkage inside the cell, the zinc-endopeptidase activity of the L chain is liberated.

The invention provides in vivo and in vitro cell-based assays for determining the presence or absence of an active clostridial toxin in a sample or for determining the activity of any clostridial toxin, including botulinum toxins of all serotypes and tetanus toxins. The novel substrate compositions, cells and assays of the invention reduce the need for animal toxicity studies, yet serve to analyze multiple toxin functions, namely, binding and cellular uptake of the toxin, translocation into the cell cytosol, and protease activity. These novel compositions and methods can be used to analyze crude and bulk samples as well as highly purified dichain toxins or formulated toxin products and, furthermore, are amenable to automated high-throughput assay formats.

As discussed below, fluorescence resonance energy transfer (FRET) is a distance-dependent interaction between the electronic excited states of two molecules in which excitation is transferred from a donor fluorophore to an acceptor without emission of a photon. The process of energy transfer results in a reduction (quenching) of fluorescence intensity and excited state lifetime of the donor fluorophore and, where the acceptor is a fluorophore, can produce an increase in the emission intensity of the acceptor. Upon cleavage of the clostridial toxin substrate within a cell of the invention after being contacted with a sample containing active toxin, resonance energy transfer is reduced and can be detected, for example, by increased donor fluorescence emission, decreased acceptor fluorescence emission, or by a shift in the emission maxima from near the acceptor emission maxima to near the donor emission maxima. If desired, the amount of active clostridial toxin in a sample can be calculated as a function of the difference in the degree of FRET using the appropriate standards.

The tetanus and botulinum neurotoxins to which the invention relates are produced by Clostridia. These toxins cause the neuroparalytic syndromes of tetanus and botulism, with tetanus toxin acting mainly within the central nervous system and botulinum toxin acting on the peripheral nervous system. Clostridial neurotoxins share a similar mechanism of cell intoxication in which the release of neurotransmitters is blocked. In these toxins, which are composed of two disulfide-linked polypeptide chains, the larger subunit is responsible for neurospecific binding and translocation of the smaller subunit into the cytoplasm. Upon translocation and reduction in neurons, the smaller chain displays peptidase activity specific for protein components involved in neuroexocytosis. The "SNARE" protein targets of clostridial toxins are common to exocytosis in a variety of non-neuronal types; in these cells, as in neurons, light chain peptidase activity inhibits exocytosis.

Tetanus neurotoxin and botulinum neurotoxins B, D, F, and G specifically recognize VAMP (also known as synaptobrevin), an integral protein of the synaptic vesicle membrane. VAMP is cleaved at distinct bonds depending on the neurotoxin. Botulinum A and E neurotoxins recognize and cleave specifically SNAP-25, a protein of the presynaptic membrane, at two different sites in the carboxy-terminal portion of the protein. Botulinum neurotoxin C cleaves syntaxin, a protein of the nerve plasmalemma, in addition to SNAP-25. The three protein targets of the Clostridial neurotoxins are conserved from yeast to humans although cleavage sites and toxin susceptibility are not necessarily conserved (see below; see, also, Humeau et al., *Biochimie* 82:427-446 (2000); Niemann et al., *Trends in Cell Biol.* 4:179-185 (1994); and Pellizzari et al., *Phil. Trans. R. Soc. London* 354:259-268 (1999)).

Naturally occurring tetanus and botulinum neurotoxins are produced as inactive polypeptide chains of 150 kDa without a leader sequence. These toxins may be cleaved by bacterial or tissue proteinases at an exposed protease-sensitive loop, generating active dichain toxin. Naturally occurring clostridial toxins contain a single interchain disulfide bond bridging the heavy chain (H, 100 kDa) and light chain (L, 50 kDa); such a bridge is important for neurotoxicity of toxin added extracellularly (Montecucco and Schiavo, *Quarterly Rev. Biophysics* 28:423-472 (1995)).

Figure 2:
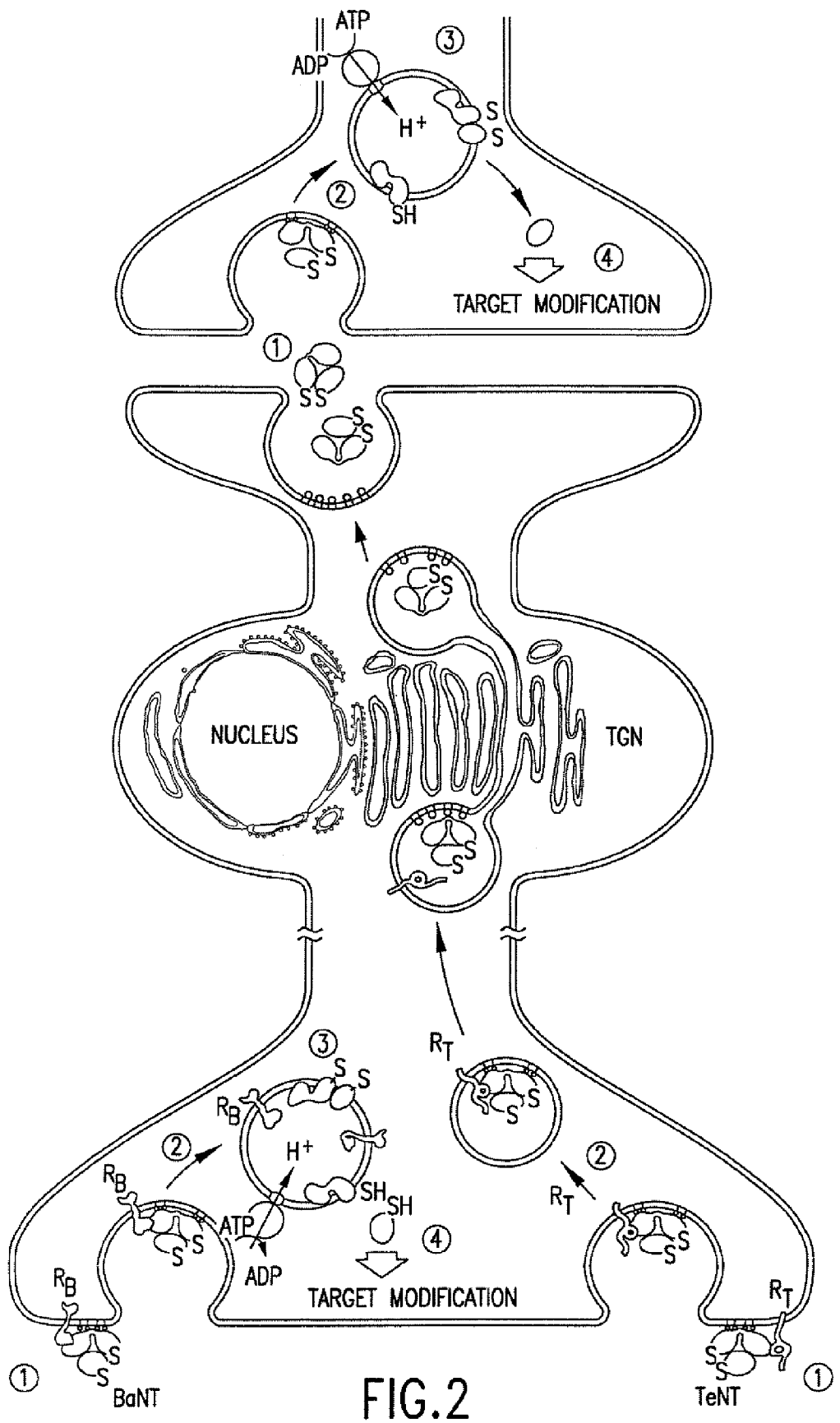
FIG. 2 shows a schematic of the four steps required for tetanus and botulinum toxin activity in central and peripheral neurons.

The clostridial toxins appear to be folded into three distinct 50 kDa domains, as shown in FIG. 1, with each domain having a distinct functional role. As illustrated in FIG. 2, the cell intoxication mechanism of the clostridial toxins consists of four distinct steps: (1) binding; (2) internalization; (3) membrane translocation; and (4) enzymatic target modification. The carboxy-terminal part of the heavy chain ($H_C$) functions in neurospecific binding, while the amino-terminal portion of the H chain ($H_N$) functions in membrane translocation. The L chain is responsible for the intracellular catalytic activity (Montecucco and Schiavo, supra, 1995).

The amino acid sequence of eight human clostridial neurotoxins has been derived from the corresponding gene (Neimann, "Molecular Biology of Clostridial Neurotoxins" in *Sourcebook of Bacterial Protein Toxins* Alouf and Freer (Eds.) pp. 303-348 London: Academic Press 1991). The L chains and H chains are composed of roughly 439 and 843 residues, respectively. Homologous segments are separated by regions of little or no similarity. The most well conserved regions of the L chains are the amino-terminal portion (100 residues) and central region (corresponding to residues 216 to 244 of TeNT), as well as the two cysteines forming the interchain disulfide bond. The 216 to 244 region contains a His-Glu-X-X-His binding motif characteristic of zinc-endopeptidases.

The clostridial toxin heavy chains are less well conserved than the light chains, and the carboxy-terminal portion of $H_C$ (corresponding to residues 1140 to 1315 of TeNT) is the most variable. This is consistent with the involvement of the $H_C$ domain in binding to nerve terminals and the fact that different neurotoxins appear to bind different receptors.

Comparison of the nucleotide and amino acid sequences of clostridial toxins indicates that they derive from a common ancestral gene. Spreading of these genes may have been facilitated by the fact that the clostridial neurotoxin genes are located on mobile genetic elements. As discussed further below, sequence variants of the seven botulinum toxins are known in the art. See, for example, FIGS. 5 to 7 and Humeau et al., supra, 2000.

As discussed above, natural targets of the clostridial neurotoxins include VAMP, SNAP-25, and syntaxin. VAMP is bound to the synaptic vesicle membrane, whereas SNAP-25 and syntaxin are bound to the target membrane (see FIG. 3). BoNT/A and BoNT/E cleave SNAP-25 in the carboxy-terminal region, releasing nine or twenty-six amino acid residues, respectively, and BoNT/C1 also cleaves SNAP-25 near the carboxy-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface. Thus, BoNT/B, BoNT/C1, BoNT/D, BoNT/F, BoNT/G or TeNT proteolysis results in release of a large portion of the cytosolic domain of VAMP or syntaxin, while only a small portion of SNAP-25 is released by BoNT/A, BoNT/C1 or BoNT/E cleavage (Montecucco and Schiavo, supra, 1995).

Naturally occurring SNAP-25, a protein of about 206 residues lacking a transmembrane segment, is associated with the cytosolic surface of the nerve plasmalemma (FIG. 3; see, also, Hodel et al., *Int. J. Biochemistry and Cell Biology* 30:1069-1073 (1998)). In addition to homologs highly conserved from *Drosophila* to mammals, SNAP-25-related proteins also have been cloned from yeast. SNAP-25 is required for axonal growth during development and may be required for nerve terminal plasticity in the mature nervous system. In humans, two isoforms are differentially expressed during development; isoform a is constitutively expressed during fetal development, while isoform b appears at birth and predominates in adult life. SNAP-25 analogues such as SNAP-23 also are expressed outside the nervous system, for example, in pancreatic cells.

Naturally occurring VAMP is a protein of about 120 residues, with the exact length depending on the species and isotype. As shown in FIG. 3, VAMP contains a short carboxy-terminal segment inside the vesicle lumen while most of the molecule is exposed to the cytosol. The proline-rich amino-terminal thirty residues are divergent among species and isoforms while the central portion of VAMP (residues 30 to 96), which is rich in charged and hydrophilic residues and includes known cleavage sites, is highly conserved. VAMP colocalizes with synaptophysin on the synaptic vesicle membrane.

A variety of species homologs of VAMP are known in the art including human, rat, bovine, Torpedo, *Drosophila*, yeast, squid and Aplysia homologs. In addition, multiple isoforms of VAMP have been identified including VAMP-1, VAMP-2 and cellubrevin, and insensitive forms have been identified in non-neuronal cells. VAMP appears to be present in all vertebrate tissues although the distribution of VAMP-1 and VAMP-2 varies in different cell types. Chicken and rat VAMP-1 are not cleaved by TeNT or BoNT/B. These VAMP-1 homologs have a valine in place of the glutamine present in human and mouse VAMP-1 at the TeNT or BoNT/B cleavage site. The substitution does not effect BoNT/D, /F or /G, which cleave both VAMP-1 and VAMP-2 with similar rates.

Syntaxin is located on the cytosolic surface of the nerve plasmalemma and is membrane-anchored via a carboxy-terminal segment, with most of the protein exposed to the cytosol. Syntaxin colocalizes with calcium channels at the active zones of the presynaptic membrane, where neurotransmitter release takes place. In addition, syntaxin interacts with synaptotagmin, a protein of the SSV membrane, that forms a functional bridge between the plasmalemma and the vesicles. A variety of syntaxin isoforms have been identified. Two isoforms of slightly different length (285 and 288 residues) have been identified in nerve cells (isoforms 1A and 1B), with isoforms 2, 3, 4 and 5 expressed in other tissues. The different isoforms have varying sensitivities to BoNT/C1, with the 1A, 1B, 2 and 3 syntaxin isoforms cleaved by this toxin.

The present invention provides a substrate composition that includes a delivery agent and a clostridial toxin substrate containing a donor fluorophore; an acceptor having an absorbance spectrum overlapping the emission spectrum of the donor fluorophore; and a clostridial toxin recognition sequence containing a cleavage site that intervenes between the donor fluorophore and the acceptor, where resonance energy transfer is exhibited between the donor fluorophore and the acceptor under the appropriate conditions. In a substrate composition of the invention, the delivery agent can be, for example, covalently linked to the clostridial toxin substrate and further can be, for example, a protein, peptide or peptidomimetic. In one embodiment, the substrate composition is a chimeric protein, peptide or peptidomimetic in which the delivery agent is operatively fused to the clostridial toxin substrate. Such a chimeric substrate composition can be, for example, a peptide or peptidomimetic having a length of at most 50 or 100 residues.

A variety of delivery agents can be covalently linked to a clostridial toxin substrate in a substrate composition of the invention including, without limitation, an antennapedia protein or active fragment thereof, such as an active fragment having the amino acid sequence RQIKIWFQNRRMKWKK (SEQ ID NO: 1); an HIV TAT protein or active fragment thereof, such as an active fragment having the amino acid sequence YGRKKRRQRRR (SEQ ID NO: 2); or a herpes simplex virus VP22 protein or active fragment thereof, such as a herpes simplex virus VP22 protein having the amino acid sequence SEQ ID NO: 3, or active fragment thereof.

The invention also provides substrate compositions in which the delivery agent is non-covalently associated with the clostridial toxin substrate. Exemplary delivery agents that can be non-covalently associated with a clostridial toxin substrate include, without limitation, Chariot™ and MPG peptides.

A variety of donor fluorophores and acceptors are useful in the substrate compositions of the invention. As non-limiting examples, donor fluorophores useful in the invention include Alexa Fluor®-488, DABCYL and BODIPY®. Acceptors useful in the invention include non-fluorescent acceptors as well as acceptor fluorophores; in one embodiment, the acceptor is an acceptor fluorophore having a fluorescence lifetime of at least 1 microsecond. In other embodiments, the invention provides a substrate composition in which the acceptor is tetramethylrhodamine, EDANS or QSY-7®. Exemplary donor fluorophore-acceptor pairs useful in a substrate composition of the invention include, without limitation, fluorescein-tetramethylrhodamine, Alexa Fluor®-488-tetramethylrhodamine, DABCYL-EDANS, fluorescein-QSY® 7, and Alexa Fluor® 488-QSY® 7.

A variety of clostridial toxin substrates are useful in the substrate compositions of the invention. Such clostridial toxin substrates include botulinum toxin substrates containing a botulinum toxin recognition sequence and tetanus toxin substrates containing a tetanus toxin recognition sequence. Thus, in one embodiment, the invention provides a BoNT/A substrate composition containing a delivery agent and a BoNT/A substrate, where the substrate includes a donor fluorophore; an acceptor having an absorbance spectrum overlapping the emission spectrum of the donor fluorophore; and a BoNT/A recognition sequence that contains a cleavage site that intervenes between the donor fluorophore and the acceptor and where, under the appropriate conditions, resonance energy transfer is exhibited between the donor fluorophore and the acceptor. The BoNT/A substrate can include, for example, at least six consecutive residues of SNAP-25, the six consecutive residues containing Gln-Arg, or a peptidomimetic thereof. A BoNT/A substrate composition of the invention can be, for example, a peptide or peptidomimetic having at most twenty, thirty, forty, fifty or 100 residues and can include any of a variety of donor fluorophore-acceptor combination such as, without limitation, fluorescein-tetramethylrhodamine, DABCYL-EDANS, and Alexa Fluor®-488-QSY-7®.

The present invention also provides a BoNT/B substrate composition containing a delivery agent and a BoNT/B substrate, where the substrate includes a donor fluorophore; an acceptor having an absorbance spectrum overlapping the emission spectrum of the donor fluorophore; and a BoNT/B recognition sequence that contains a cleavage site that intervenes between the donor fluorophore and the acceptor and where, under the appropriate conditions, resonance energy transfer is exhibited between the donor fluorophore and the acceptor. A BoNT/B substrate useful in the invention can include, for example, at least six consecutive residues of VAMP, the six consecutive residues containing Gln-Phe, or a peptidomimetic thereof. A BoNT/B substrate composition of the invention can be, for example, a peptide or peptidomimetic having at most twenty, thirty, forty, fifty or 100 residues. It is understood that a variety of donor fluorophore-acceptor combinations are useful in a BoNT/B substrate composition of the invention; such donor fluorophore-acceptor pairs include, but are not limited to, fluorescein-tetramethylrhodamine, DABCYL-EDANS, and Alexa Fluor®-488-QSY-7®.

Further provided herein is a BoNT/C1 substrate composition containing a delivery agent and a BoNT/C1 substrate, where the substrate includes a donor fluorophore; an acceptor having an absorbance spectrum overlapping the emission spectrum of the donor fluorophore; and a BoNT/C1 recognition sequence that contains a cleavage site that intervenes between the donor fluorophore and the acceptor and where, under the appropriate conditions, resonance energy transfer is exhibited between the donor fluorophore and the acceptor. BoNT/C1 substrates useful in the substrate compositions of the invention encompass those having at least six consecutive residues of syntaxin, the six consecutive residues containing Lys-Ala, or a peptidomimetic thereof, and those including at least six consecutive residues of SNAP-25, the six consecutive residues containing Arg-Ala, or a peptidomimetic thereof. A BoNT/C1 substrate composition of the invention can be, for example, a peptide or peptidomimetic having a variety of lengths, for example, at most twenty, thirty, forty, fifty or 100 residues A variety of donor fluorophore-acceptor combinations are useful in a BoNT/C1 substrate composition of the invention including, without limitation, fluorescein-tetramethylrhodamine, DABCYL-EDANS, and Alexa Fluor®-488-QSY-7®.

The invention also provides a BoNT/D substrate composition containing a delivery agent and a BoNT/D substrate, where the substrate includes a donor fluorophore; an acceptor having an absorbance spectrum overlapping the emission spectrum of the donor fluorophore; and a BoNT/D recognition sequence containing a cleavage site that intervenes between the donor fluorophore and the acceptor and where, under the appropriate conditions, resonance energy transfer is exhibited between the donor fluorophore and the acceptor. A variety of BoNT/D substrates are useful in the substrate compositions of the invention including, yet not limited to, BoNT/D substrates containing at least six consecutive residues of VAMP, the six consecutive residues containing Lys-Leu, or a peptidomimetic thereof. As for the other substrate compositions discussed above, a BoNT/D substrate composition can be a peptide or peptidomimetic having, for example, at most twenty, thirty, forty, fifty or 100 residues and can include any of a variety of donor fluorophore-acceptor combinations such as, for example, fluorescein-tetramethylrhodamine, DABCYL-EDANS, or Alexa Fluor®-488-QSY-7®.

The invention additionally provides a BoNT/E substrate composition containing a delivery agent and a BoNT/E substrate, where the substrate includes a donor fluorophore; an acceptor having an absorbance spectrum overlapping the emission spectrum of the donor fluorophore; and a BoNT/E recognition sequence which contains a cleavage site that intervenes between the donor fluorophore and the acceptor and where, under the appropriate conditions, resonance energy transfer is exhibited between the donor fluorophore and the acceptor. A BoNT/E substrate useful in the invention can have, for example, at least six consecutive residues of SNAP-25, the six consecutive residues containing Arg-Ile, or a peptidomimetic thereof. A BoNT/E substrate composition of the invention can be, for example, a peptide or peptidomimetic having at most twenty, thirty, forty, fifty or 100 residues. Such a substrate composition further can include, for example, a donor fluorophore-acceptor combination such as fluorescein-tetramethylrhodamine, DABCYL-EDANS or Alexa Fluor®-488-QSY-7®.

Also provided herein is a BoNT/F substrate composition containing a delivery agent and a BoNT/F substrate, where the substrate includes a donor fluorophore; an acceptor having an absorbance spectrum overlapping the emission spectrum of the donor fluorophore; and a BoNT/F recognition sequence containing a cleavage site that intervenes between the donor fluorophore and the acceptor and where, under the appropriate conditions, resonance energy transfer is exhibited between the donor fluorophore and the acceptor. BoNT/F substrates useful in the substrate compositions of the invention can have, for example, at least six consecutive residues of VAMP, the six consecutive residues containing Gln-Lys, or a peptidomimetic thereof. Furthermore, a BoNT/F substrate composition of the invention can be, for example, a peptide or peptidomimetic having at most twenty, thirty, forty, fifty or 100 residues. One skilled in the art understands that any of a variety of fluorophore-acceptor combinations are useful in a BoNT/F substrate composition; these include, as non-limiting examples, fluorescein-tetramethylrhodamine, DABCYL-EDANS, and Alexa Fluor®-488-QSY-7®.

The present invention further provides a BoNT/G substrate composition containing a delivery agent and a BoNT/G substrate, where the substrate includes a donor fluorophore; an acceptor having an absorbance spectrum overlapping the emission spectrum of the donor fluorophore; and a BoNT/G recognition sequence containing a cleavage site that intervenes between the donor fluorophore and the acceptor and where, under the appropriate conditions, resonance energy transfer is exhibited between the donor fluorophore and the acceptor. Useful BoNT/G substrates include, yet are not limited to, those having at least six consecutive residues of VAMP, the six consecutive residues containing Ala-Ala, or a peptidomimetic thereof. A BoNT/G substrate composition of the invention can be, for example, a peptide or peptidomimetic having at most twenty, thirty, forty, fifty or 100 residues and can include, for example, a donor fluorophore-acceptor combination such as fluorescein-tetramethylrhodamine, DABCYL-EDANS, or Alexa Fluor®-488-QSY-7®.

The invention also provides a TeNT substrate composition containing a delivery agent and a TeNT substrate, where the substrate includes a donor fluorophore; an acceptor having an absorbance spectrum overlapping the emission spectrum of the donor fluorophore; and a TeNT recognition sequence containing a cleavage site that intervenes between the donor fluorophore and the acceptor and where, under the appropriate conditions, resonance energy transfer is exhibited between the donor fluorophore and the acceptor. A variety of TeNT substrates are useful in the substrate invention including those having at least six consecutive residues of VAMP, the six consecutive residues containing Gln-Phe, or a peptidomimetic thereof. Such a TeNT substrate composition of the invention can be, for example, a peptide or peptidomimetic having at most twenty, thirty, forty, fifty or 100 residues. Furthermore, a variety of fluorophore-acceptor combinations are useful in a TeNT substrate composition of the invention; these combinations include but are not limited to fluorescein-tetramethylrhodamine, DABCYL-EDANS and Alexa Fluor®-488-QSY-7®.

In the substrate compositions of the invention, a delivery agent facilitates uptake of a clostridial toxin substrate into a cell such as neuron or a glandular cell such as a pancreatic acinar cell. The delivery agent can be covalently linked to the clostridial toxin substrate or can be non-covalently associated with the clostridial toxin substrate. As non-limiting examples, delivery agents useful in the substrate compositions of the invention include antennapedia proteins, HIV TAT proteins, herpes simplex virus VP22 proteins, and active fragments thereof, as well as delivery agents such as Chariot™ and other MPG peptides, each of which is discussed further hereinbelow.

As used herein, the term "delivery agent" means any molecule that enables or enhances internalization of an associated or linked clostridial toxin substrate into a cell. Delivery agents are known in the art and include but are not limited to protein transduction peptides and peptidomimetics and cell-permeant peptides and peptidomimetics. The term delivery agent encompasses, without limitation, proteins, peptides, peptidomimetics, small molecules, nucleic acid molecules, liposomes, lipids, viruses, retroviruses and cells. It is understood that a substrate composition containing a delivery agent useful in the invention generally is not retained in intracellular vesicles upon internalization but rather is eventually delivered, for example, to the cytoplasm. Thus, the term delivery agent encompasses, without limitation, molecules that transport associated or linked substrate to the cell cytoplasm or nucleus. It further is understood that the term "delivery agent" encompasses molecules that are internalized by any mechanism, including delivery agents which function via receptor-mediated endocytosis and those which are independent of receptor-mediated endocytosis.

A variety of delivery agents can be covalently linked to a clostridial toxin substrate in a composition of the invention, including, without limitation, protein transduction peptides, cell permeant peptides, phosphopeptides, peptides containing D-amino acids, and other denatured or folded, modified or unmodified, and naturally occurring or synthetic proteins, peptides and peptidomimetics. Such delivery agents include, without limitation, nuclear and secreted proteins and active fragments and analogs thereof. In particular embodiments, a delivery agent useful in the invention is a peptide or peptidomimetic having a length of less than 50 residues, a length of less than 40 residues, a length of less than 30 residues, a length of less than 20 residues, or a length of less than 15 residues. In a further embodiment, a delivery agent useful in the invention is a predominantly hydrophobic peptide or peptidomimetic. In another embodiment, a delivery agent useful in the invention is a predominantly basic peptide or peptidomimetic. In yet another embodiment, a delivery agent useful in the invention is an α-helical peptide or peptidomimetic such as an amphipathic α-helical peptide or peptidomimetic. In a further embodiment, a delivery agent useful in the invention is an amphipathic peptide or peptidomimetic such as a basic amphipathic peptide or peptidomimetic. And, in a further embodiment, a delivery agent useful in the invention is a denatured peptide or peptidomimetic, which is linked to a denatured or folded clostridial toxin substrate; denaturation has been shown to facilitate internalization as described, for example, in WO 99/55899.

As non-limiting examples, delivery agents suitable for use in the invention when covalently linked to a clostridial toxin substrate include ciliary neurotrophic factor (CNTF) or an active fragment thereof; caveolin or an active fragment thereof; interleukin-1β (IL-1β) or an active fragment thereof; thioredoxin or an active fragment thereof; Antennapedia or an active fragment thereof such as penetratin-1 (SEQ ID NO: 1); fibroblast growth factor-1 (FGF-1) or an active fragment thereof; Engrailed or an active fragment thereof; Hoxa-5 or an active fragment thereof; Kaposi fibroblast growth factor (kFGF) or an active fragment thereof, for example, AAVALL-PAVLLALLAP (SEQ ID NO: 22); human β3 integrin or an active fragment thereof such as a hydrophobic signal sequence; a nuclear localization sequence (NLS) such as TPPKKKRKVEDP (SEQ ID NO: 23); FGF-2 or an active fragment thereof; transportan or an active fragment thereof such as GWTLNSAGYLLGKINLKALAALAKKIL (SEQ ID NO: 24); lactoferrin or an active fragment thereof; VP22 or an active fragment thereof; HIV type I transactivator (HIV TAT) or an active fragment thereof such as YGRKKRRQRRR (SEQ ID NO: 2); or a heat shock protein such as HSP70 or an active fragment thereof. These and additional delivery agents are well known in the art as described, for example, in Ho, *Cancer Res.* 61:474-477 (2001); Schwarze and Dowdy, *Trends Pharmacol. Sci.* 21:45-48 (2000); Prochiantz, *Curr. Opin. Cell Biol.* 12:400-406 (2000); Ford et al., *Gene Therapy* 8:1-4 (2001); Dunican and Doherty, *Biopolymers Peptide Sci.* 60:45-60 (2001); and Schwartz and Zhang, *Curr. Opin. Mol. Ther.* 2:162-167 (2000).

In one embodiment, the invention is practiced with a delivery agent which is a homeoprotein or an active fragment thereof, for example, a homeodomain or an active fragment thereof. Homeoproteins are helix-turn-helix proteins that contain a DNA-binding domain of about 60 residues, denoted the homeodomain. A variety of homeoproteins, homeodomains and active fragments thereof can be delivery agents useful in the invention including, without limitation, Antennapedia, Engrailed1 (En1), Engrailed2 (En2), Hoxa-5, Hoxc-8, Hoxb-4 and Knotted-1 (KN1). As an example, En1 and En1 have been expressed in COS7 cells, where they are first secreted and then internalized by other cells. See, for example, Prochiantz, supra, 2000.

In another embodiment, a substrate composition of the invention includes a delivery agent which is the homeodomain protein, Antennapedia, or an active fragment thereof. Antennapedia is a member of a family of developmentally important *Drosophila* homeoproteins which translocate across neuronal membranes. The third helix of the Antennapedia homeodomain, the 16 residue peptide "penetratin-1" (SEQ ID NO: 1), is internalized into live cells. The internalization occurs both at 37° C. and 4° C., indicating that delivery is neither receptor-mediated nor energy-dependent. Additional delivery agents include peptides and peptidomimetics related in sequence to Penetratin-1 such as, without limitation, one of the peptides shown below in Table A or another penetratin-derived peptide or peptidomimetic, including a retroinverse or all D-amino acid peptide or peptidomimetic, or a related but non-α-helical peptide or peptidomimetic (see, for example, Prochiantz, supra, 2000). In one embodiment, such a penetratin-derived peptide retains the tryptophan, phenylalanine and glutamine residues of penetratin-1 (SEQ ID NO: 1).

TABLE A

Penetratin-Derived Peptides Useful as Delivery Agents

| Peptide | Sequence | SEQ ID NO: |
|---------|----------|------------|
| 43-58 | RQIKIWFQNRRMKWKK | 1 |
| 58-43 | KKWKMRRNQFWIKIQR | 25 |
| 43-58 | RQIKIWFQNRRMKWKK | 26 |
| Pro50 | RQIKIWFPNRRMKWKK | 27 |
| 3Pro | RQPKIWFPNRRMPWKK | 28 |
| Met-Arg | RQIKIWFQNMRRKWKK | 29 |
| 7Arg | RQIRIWFQNRRMRWRR | 30 |
| W/R | RRWRRWWRRWWRRWRR | 31 |

In another embodiment, a substrate composition of the invention includes a delivery agent which is a HIV transactivator (TAT) protein or an active fragment thereof. Such a delivery agent can include, for example, a sequence identical or similar to residues 47-57 or 47-59 of HIV TAT (Schwartz et al., *Science* 285:1569-1572 (1999); and Ho et al., supra, 2001). As an example, fusion proteins including residues 47-57 of HIV TAT (YGRKKRRQRRR; SEQ ID NO: 2) cross the plasma membrane of, for example, human and murine cells in vitro and in vivo (Schwartz and Zhang, supra, 2000); a variety of proteins from 15 to 120 KDa have been shown to retain biological activity when fused to a HIV TAT delivery agent. An HIV TAT delivery agent can be positively charged and can function, for example, in an energy-, receptor-, transporter- and endocytosis-independent manner to deliver a covalently linked clostridial toxin substrate to, for example, 90-100% of target cells.

A substrate composition of the invention also can include as a delivery agent a herpes simplex virus VP22 protein or active fragment thereof. In one embodiment, a substrate composition of the invention includes an HSV type 1 (HSV-1) VP22 protein or active fragment thereof. HSV VP22, a nuclear transcription factor, can cross the plasma membrane through non-classical endocytosis and can enter cells independent of GAP junctions and physical contacts. As a fusion with a variety of different proteins, HSV VP22 results in uptake into cells of different types including terminally differentiated cells (Ford et al., supra, 2001; Schwartz and Zhang, supra, 2000) and can function to deliver a linked clostridial toxin substrate to, for example, 90-100% of cultured cells.

In another embodiment, a delivery agent useful in the invention corresponds to or is derived from a hydrophobic signal sequence. Such a delivery agent can be, for example, the Kaposi fibroblast growth factor (kFGF) or an active fragment thereof such as AAVALLPAVLLALLAP (SEQ ID NO: 22); human β3 integrin or an active fragment thereof; or another hydrophobic delivery agent such as one of those described in Dunican and Doherty, supra, 2001.

A delivery agent useful in the invention also can be a synthetic sequence that shares one or more characteristics of a naturally occurring delivery agent such as a protein transduction domain (PTD). Such delivery agents include, but are not limited to, L- and D-arginine oligomers, for example, 9-mers of L- or D-arginine and related peptoids (Wender et al., *Proc. Natl. Acad. Sci., USA* 97:13003-13008 (2000). Such delivery agents further include basic peptides and peptidomimetics; basic α-helical peptides and peptidomimetics; and peptides and peptidomimetics with optimized arginine alignment or optimized α-helical character as compared to a naturally occurring protein transduction domain such as residues 47-57 of HIV TAT. See, for example, Ho et al., supra, 2001, and WO 99/29721. Additional non-limiting examples of delivery agents useful in the invention include $SCWK_{n\ (SEQ\ ID\ NO:\ 32)}$; $(LARL)_{n\ (SEQ\ ID\ NO:\ 33)}$; HA2; RGD; $K_{16}RGD$ (SEQ ID NO: 34); Ioligomer; $AlkCWK_{18}$ (SEQ ID NO: 35); DiCWK18 (SEQ ID NO: 36); DipaLytic; Plae (SEQ ID NO: 37); Kplae (SEQ ID NO: 38) and other delivery agents known in the art or which can be prepared by routine methods (see, for example, Schwartz and Zhang, supra, 2000). The skilled person understands that these and other naturally occurring and synthetic delivery agents can be useful in the substrate compositions of the invention.

A delivery agent useful in the invention also can be an agent that enables or enhances cellular uptake of a non-covalently associated clostridial toxin substrate. In one embodiment, such a delivery agent is peptide containing two independent domains: a hydrophobic domain and a hydrophilic domain. In another embodiment, such a delivery agent is an MPG peptide, which is a peptide derived from both the nuclear localization sequence (NLS) of SV40 large T antigen and the fusion peptide domain of HIV-1 gp41. In a further embodiment, such a delivery agent is an MPG peptide having the amino acid sequence GALFLGFLGAAGSTMGAWSQPKSKRKV (SEQ ID NO: 39). In yet a further embodiment, such a delivery agent is an amphipathic peptide such as Pep-1. These and related delivery agents that function in the absence of covalent linkage, sometimes known as "protein transfection products," are well known in the art as described, for example, in Morris et al., *Nucl. Acids Res.* 27:3510-3517 (1999); Morris et al., *J. Biol. Chem.* 274:24941-24946 (1999); and Morris et al., *Nature Biotech.* 19:1173-1176 (2001). Such peptide delivery agents can be prepared by routine methods and are commercially available; as an example, the Chariot™ product is available from Active Motif (Carlsbad, Calif.).

A clostridial toxin substrate useful in the invention includes, in part, a donor fluorophore. As used herein, the term "donor fluorophore" means a molecule that, when irradiated with light of a certain wavelength, emits light, also denoted fluorescence, of a different wavelength. The term fluorophore is synonymous in the art with the term "fluorochrome."

A clostridial toxin substrate useful in the invention also includes, in part, an acceptor. As used herein, the term "acceptor" means a molecule that can absorb energy from, and upon excitation of, a donor fluorophore and is a term that encompasses fluorophores as well as non-fluorescent molecules. An acceptor useful in a clostridial toxin substrate has an absorbance spectrum which overlaps the emission spectrum of a donor fluorophore included in the substrate. An acceptor useful in the invention generally has rather low absorption at a wavelength suitable for excitation of the donor fluorophore.

As set forth above, an acceptor has an absorbance spectrum that overlaps the emission spectrum of the donor fluorophore. The term "overlapping," as used herein in reference to the absorbance spectrum of an acceptor and the emission spectrum of a donor fluorophore, means an absorbance spectrum and emission spectrum that are partly or entirely shared. Thus, in such overlapping spectra, the high end of the range of the donor fluorophore's emission spectrum is higher than the low end of the range of the acceptor's absorbance spectrum.

A clostridial toxin substrate useful in the invention contains a cleavage site that "intervenes" between a donor fluorophore and an acceptor having an absorbance spectrum which overlaps the emission spectrum of the donor fluorophore. Thus, the cleavage site is positioned in between the fluorophore and acceptor such that cleavage at the site results in a first molecule containing the fluorophore and a second molecule containing the acceptor. It is understood that all or only a portion of the clostridial toxin recognition sequence can intervene between the donor fluorophore and acceptor.

A clostridial toxin substrate useful in the invention contains, in part, a clostridial toxin recognition sequence which includes a cleavage site. Such a clostridial toxin substrate is susceptible to cleavage by at least one clostridial toxin under conditions suitable for clostridial toxin protease activity.

As used herein, the term "clostridial toxin recognition sequence" means a scissile bond together with adjacent or non-adjacent recognition elements sufficient for detectable proteolysis at the scissile bond by a clostridial toxin under conditions suitable for clostridial toxin protease activity. A variety of useful clostridial toxin recognition sequences are discussed hereinbelow.

In particular embodiments, a substrate composition of the invention is a chimeric protein, peptide or peptidomimetic. A substrate composition of the invention can be, for example, a chimeric peptide or peptidomimetic having at most 20 residues, at most 40 residues, at most 50 residues, at most 100 residues, at most 150 residues, at most 200 residues, at most 250 residues, at most 300 residues, at most 350 residues or at most 400 residues.

As used herein, the term "peptidomimetic" is used broadly to mean a peptide-like molecule that is cleaved by the same clostridial toxin as the peptide substrate upon which it is structurally based. Such peptidomimetics include chemically modified peptides, peptide-like molecules containing non-naturally occurring amino acids, and peptoids, which are peptide-like molecules resulting from oligomeric assembly of N-substituted glycines, and are cleaved by the same clostridial toxin as the peptide substrate upon which the peptidomimetic is derived (see, for example, Goodman and Ro, *Peptidomimetics for Drug Design*, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; an α,α-dialkyl-glycine or α-aminocycloalkane carboxylic acid; an $N^\alpha$-$C^\alpha$ cyclized amino acid; an $N^\alpha$-methylated amino acid; a β- or γ-amino cycloalkane carboxylic acid; an α,β-unsaturated amino acid; a β,β-dimethyl or β-methyl amino acid; β-substituted-2,3-methano amino acid; an $NC^\delta$ or $C^\alpha$-$C^\delta$ cyclized amino acid; or a substituted proline or another amino acid mimetic. In addition, a peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Further provided herein is a cell containing a clostridial toxin substrate that includes a donor fluorophore; an acceptor having an absorbance spectrum overlapping the emission spectrum of the donor fluorophore; and a clostridial toxin recognition sequence containing a cleavage site that intervenes between the donor fluorophore and the acceptor, where resonance energy transfer is exhibited between the donor fluorophore and the acceptor under the appropriate conditions. In one embodiment, the cell is a transfected cell. In another embodiment, the cell is a stably transfected cell. A variety of cells are useful in the invention including, without limitation, primary cells; established cells; human cells; neuronal cells such as primary neurons, established neurons and human neurons; and non-neuronal cells, which can be, for example, glandular cells such as pancreatic acinar cells. Neurons useful in the invention include CNS neurons and peripheral neurons; as non-limiting examples, such neurons include neuroblastoma cells, spinal cord neurons, dorsal root ganglion neurons, cerebral cortex neurons, cerebellar neurons, hippocampal neurons and motor neurons.

In a cell of the invention, the clostridial toxin substrate optionally can be covalently linked to a delivery agent. Such a delivery agent can be, for example, a protein, peptide or peptidomimetic. A variety of delivery agents can be useful in a cell of the invention including, without limitation, an antennapedia protein or active fragment thereof, such as an active fragment having the amino acid sequence RQIKIWFQNR-RMKWKK (SEQ ID NO: 1); an HIV TAT protein or active fragment thereof, such as an active fragment having the amino acid sequence YGRKKRRQRRR (SEQ ID NO: 2); or a herpes simplex virus VP22 protein or active fragment thereof, such as a herpes simplex virus VP22 protein having the amino acid sequence SEQ ID NO: 3, or active fragment thereof. In one embodiment, the invention provides a cell containing a chimeric protein, peptide or peptidomimetic that includes a clostridial toxin substrate and a delivery agent operatively fused to the substrate. Such a chimeric protein, peptide or peptidomimetic can have, for example, a length of at most 50 or 100 residues.

A variety of clostridial toxin substrates can be included in a cell of the invention. Such clostridial toxin substrates include botulinum toxin substrates of all serotypes as well as tetanus toxin substrates. In one embodiment, the invention provides a cell containing a BoNT/A substrate that includes, in part, a BoNT/A recognition sequence. Such a BoNT/A substrate can include, for example, at least six consecutive residues of SNAP-25, the six consecutive residues containing Gln-Arg, or a peptidomimetic thereof. In another embodiment, the invention provides a cell containing a BoNT/B substrate which includes, in part, a BoNT/B recognition sequence. BoNT/B substrates useful in the cells of the invention include, without limitation, those having at least six consecutive residues of VAMP, the six consecutive residues containing Gln-Phe, or a peptidomimetic thereof. In a further embodiment, the invention provides a cell containing a BoNT/C1 substrate that includes, in part, a BoNT/C1 recognition sequence; BoNT/C1 substrates useful in the cells of the invention encompass those having at least six consecutive residues of syntaxin, the six consecutive residues containing Lys-Ala, or a peptidomimetic thereof, and those including at least six consecutive residues of SNAP-25, the six consecutive residues containing Arg-Ala, or a peptidomimetic thereof. In another embodiment, the invention provides a cell containing a BoNT/D substrate that includes, in part, a BoNT/D recognition sequence. A variety of BoNT/D substrates are useful in the cells of the invention including, yet not limited to, BoNT/D substrates having at least six consecutive residues of VAMP, the six consecutive residues containing Lys-Leu, or a peptidomimetic thereof.

In a further embodiment, the invention provides a cell containing a BoNT/E substrate that includes, in part, a BoNT/E recognition sequence. Such a BoNT/E substrate can have, for example, at least six consecutive residues of SNAP-25, the six consecutive residues containing Arg-Ile, or a peptidomimetic thereof. In an additional embodiment, there is provided herein a cell containing a BoNT/F substrate that includes, in part, a BoNT/F recognition sequence. BoNT/F substrates useful in the cells of the invention can have, for example, at least six consecutive residues of VAMP, the six consecutive residues containing Gln-Lys, or a peptidomimetic thereof. In still a further embodiment, the invention provides a cell containing a BoNT/G substrate that includes, in part, a BoNT/G recognition sequence. Useful BoNT/G substrates include, yet are not limited to, those having at least six consecutive residues of VAMP, the six consecutive residues containing Ala-Ala, or a peptidomimetic thereof. In a further embodiment, the present invention provides a cell containing a TeNT substrate which includes, in part, a TeNT recognition sequence. A variety of TeNT substrates are useful in the invention including those having at least six consecutive residues of VAMP, the six consecutive residues containing Gln-Phe, or a peptidomimetic thereof.

As described further herein, a variety of donor fluorophores and acceptors are useful in the cells of the invention. Donor fluorophores useful in the invention include, without limitation, Alexa Fluor®-488, DABCYL and BODIPY®. Acceptors useful in the invention include non-fluorescent acceptors as well as acceptor fluorophores, including acceptor fluorophores having a fluorescence lifetime of at least 1 microsecond. Acceptors useful in the cells of the invention further include tetramethylrhodamine, EDANS and QSY-7®.

The term "cell," as used herein, means any eukaryotic cell that expresses, or can be engineered to express, at least one receptor that binds a clostridial toxin. The term cell encompasses, without limitation, primary cells; cultured cells; established cells; normal cells; transformed cells; tumor cells; infected cells; stably or transiently transfected cells, including stably and transiently transfected cells; and proliferating and terminally differentiated cells, as well as cells of a variety of species and cell types. Thus, the term cell encompasses, without limitation, mammalian cells such as murine, rat, porcine, bovine, equine, primate and human cells. It is understood that cells useful in the invention can be in any state such as proliferating or quiescent; intact or permeabilized such as through electroporation or treatment with digitonin; and further can be in isolated form or part of a heterogeneous cell population, tissue or organism. It further is understood that cells useful in the invention include those which express a clostridial toxin substrate under control of a constitutive or inducible promoter and that these and other cells useful in the invention can express one or more endogenous clostridial toxin target proteins or can express low or undetectable levels of one or all target proteins such as SNAP-25, VAMP and syntaxin.

Cells useful in the invention include those that express one or more endogenous low or high affinity clostridial toxin receptors; cells that express low or undetectable levels of endogenous receptor and that have been transfected with, or otherwise engineered to express, one or more exogenous nucleic acid molecules encoding one or more clostridial toxin receptors; and cells that express a combination of endogenous and exogenous toxin receptors for one or more clostridial toxin serotypes. It is understood that the selection of a cell depends, in part, on which clostridial toxin is to be assayed. As an example, to assay for BoNT/A activity, one selects a cell that expresses or can be engineered to express a low or high affinity receptor for BoNT/A.

In one embodiment, the invention provides a neuron containing a clostridial toxin substrate that includes a donor fluorophore, an acceptor having an absorbance spectrum overlapping the emission spectrum of the donor fluorophore, and a clostridial toxin recognition sequence including a cleavage site, where the cleavage site intervenes between the donor fluorophore and the acceptor and where resonance energy transfer is exhibited between the donor fluorophore and the acceptor under the appropriate conditions.

A variety of neurons can be useful in the invention. As non-limiting examples, a neuron useful in the invention can be a primary neuron; established neuron; transformed neuron; stably transfected neuron; or motor or sensory neuron, and further can be, for example, a mammalian, murine, rat, primate or human neuron. A neuron useful in the invention can be a peripheral neuron or CNS neuron; as non-limiting examples, spinal cord neurons such as an embryonic spinal cord neurons, dorsal root ganglia (DRG) neurons, cerebral cortex neurons, cerebellar neurons, hippocampal neurons and motor neurons can be useful in the invention as described further below.

Exemplary neurons useful in the invention include, but are not limited to, primary cultures of embryonic DRG neurons, for example, primary cultures of embryonic rat DRG neurons as described in Welch et al., *Toxicon* 38:245-258 (2000); and primary cultures of fetal spinal cord neurons, for example, primary cultures of murine fetal spinal cord neurons as described in Neale et al., *J. Cell Biol.* 147:1249-1260 (1999), or Chaddock et al., *Infect. Immun.* 68:2587-2593 (2000)).

Exemplary neuronal cell lines useful in the invention include, without limitation, neuroblastoma cell lines such as LA-N-2, SH-SY5Y, N2a, NS-20Y and NIE-115; hybrid cell lines, including neuroblastoma/glioma hybrids such as NG108-C15; motor neuron cell lines such as NSC-34 and NSC-19; spinal cord cell lines such as M4b; CNS cell lines; cerebral cortex cell lines such as CNh; dorsal root ganglion cell lines such as G4b; hippocampal cell lines such as HT-22; and pheochromocytoma cell lines such as PC12.

A neuronal cell line useful in the invention can be, for example, a neuroblastoma cell line such as a murine, primate or human neuroblastoma cell line. Exemplary neuroblastoma cell lines useful in the invention include, without limitation, LA-N-2, SH-SY5Y, N2a, NS-20Y and NIE-115. As an example, the invention can be practiced with the LA-N-2 human neuroblastoma cell line, which has properties of cholinergic neurons and expresses well characterized cholinergic markers (Rylett et al., *J. Neurochem.* 61:1388-1397 (1993); Singh et al., *J. Neurosci. Res.* 25:476-485 (1990); and Yeh et al., *Neuroscience* 27:309-315 (1988)). As a further example, the invention can be practiced with the SH-SY5Y human neuroblastoma cell line, which exhibits inhibition of [$^3$H]-noradrenaline release induced by $K^+/Ca^{2+}$ upon exposure to botulinum toxin (Purkiss et al., *Neurotoxicology* 22:447-453 (2001)).

Hybrid neuronal cell lines such as murine, primate and human hybrid neuronal cell lines also can be useful in the invention. Such hybrid cell lines include neuroblastoma hybrids such as neuroblastoma/glioma hybrids. As an example, the NG108-C15 cell line is a hybrid of mouse neuroblastoma and rat glioma cells that can be useful in the invention (Yokosawa et al., *Infect. Immun.* 57:272-277 (1989); Yokosawa et al., *Toxicon* 29:261-264 (1991)). The NG108-C15 cell line can be engineered to include, for example, a BoNT/C1 substrate to assay for BoNT/C1 activity. Additional hybrid cell lines include NSC cell lines, which are hybrids of neuroblastomas and spinal cord neurons that resemble developing motor neurons (Cashman et al., *Dev. Dyn.* 194:209-221 (1992)).

A neuronal cell line useful in the invention also can be a motor neuron cell line such as a murine, primate or human motor neuron cell line. NSC-34 and NSC-19 are exemplary motor neuron cell lines useful in the invention; these cell lines, which are clonal hybrids of mouse neuroblastoma (N18TG2) and isolated embryonic (day 12-14) mouse spinal cord motor neurons, express motor neuron characteristics and display a multipolar neuron-like phenotype (Eggett et al., *J. Neurochem.* 74:1895-1902 (2000)). NSC-34 and NSC-19 cells express high levels of choline acetyltransferase (CHAT), a marker of motor neurons. These cells also generate action potentials; express neurofilament triplet proteins; and synthesize, store and release acetylcholine.

A neuronal cell line useful in the invention also can be a spinal cord cell line such as a murine, primate or human spinal cord cell line. As an example, a human spinal cord cell line can be generated from precursors of human embryonic spinal cord cells (first trimester embryos) that are immortalized with a tetracycline repressible v-myc oncogene as described in Li et al., *J. Neurosci. Res.* 59:342-352 (2000). Such cells can be expanded indefinitely in proliferative growth conditions before rapid differentiation (4-7 days) into functional neurons that express neuronal phenotypic markers such as choline acetyltransferase. As another example, a murine spinal cord cell line can be prepared by immortalizing an embryonic spinal cord culture using transforming media. Such a spinal cord cell line can be, for example, the murine M4b line and can express neuronal markers such as NSE, synaptophysin, MAP-2, and choline acetyltransferase and release acetylcholine upon appropriate stimulation (Cardenas et al., *J. Neurosci. Res.* 68:46-58 (2002)).

Human central nervous system (CNS) cell lines, including murine, primate and human CNS cell lines, also can be useful in the invention. A useful CNS cell line can be, for example, a human CNS cell line immortalized with a tetracycline repressible v-myc oncogene as described in Sah et al., *Nature Biotechnol.* 15:574-580 (1997). Upon repression of the oncogene, the cells differentiate into neurons.

Cerebral cortex (CNh) cell lines also are neurons useful in the invention. Useful cerebral cortex cell lines include, but are not limited to, murine, primate and human cell lines. As an example, murine cortex primary cultures from 12-16 days embryos can be immortalized, for example, by culturing the cells in conditioned media from a rat thyroid cell line that induces transformation in vitro. The immortalized cells can be differentiated into neurons expressing neuronal markers using the appropriate media; these differentiated cells express choline acetyltransferase and secrete acetylcholine and glutamate in response to depolarization and nicotine stimulation (Allen et al., *Eur. J. Neurosci.* 12:3259-3264 (2000)).

Dorsal root ganglia cell lines including murine, primate and human dorsal root ganglia cell lines also can be useful in the invention. Embryonic dorsal root ganglia primary cultures can be immortalized with transforming conditioned media as described above. Upon differentiation, the cell line exhibits neuronal traits and lacks glial markers by immunohistochemistry. Release of neurotransmitters such as acetylcholine can be induced in response to potassium and nicotine (Allen et al., *Neuroreport* 13:491-496 (2002)). An exemplary DRG cell line useful in the invention is the murine DRG cell line G4b.

The invention also can be practiced with hippocampal cell lines, including murine, primate and human hippocampal lines. As a non-limiting example, the murine hippocampal cell line HT-22 can be useful in the invention. The skilled person understands that these and additional primary and established neurons can be useful in the compositions and methods of the invention.

It is understood that the invention can be practiced with both intact and permeabilized cells. In one embodiment, a cell of the invention is permeabilized, for example, through electroporation or exposure to digitonin or low ionic strength buffer. In one further embodiment, a cell of the invention is a permeabilized PC12 cell.

As discussed above, it is understood that a neuron useful in the invention expresses endogenous or exogenous low or high affinity receptors for one or more clostridial toxins. Such a neuron also generally exhibits inhibition of exocytosis upon exposure to clostridial toxin with, for example, an $IC_{50}$ of less than 50 nM, less than 5 nM, less than 0.5 nM, less than 0.05 nM, less than 0.005 nM, less than 0.0005 nM, less than 0.00005 nM or less than 0.000005 nM. In particular embodiments, the invention provides a neuron containing a BoNT/A substrate which exhibits inhibition of exocytosis with an $IC_{50}$ of less than 50 nM, less than 5 nM, less than 0.5 nM, less than 0.05 nM, less than 0.005 nM, less than 0.0005 nM, less than 0.00005 nM or less than 0.000005 nM upon exposure to BoNT/A. In further embodiments, the invention provides a neuron containing a BoNT/B substrate which exhibits inhibition of exocytosis with an $IC_{50}$ of less than 50 nM, less than 5 nM, less than 0.5 nM, less than 0.05 nM, less than 0.005 nM, less than 0.0005 nM, less than 0.00005 nM or less than 0.000005 nM upon exposure to BoNT/B. In other embodiments, the invention provides a neuron containing a BoNT/C1 substrate which exhibits inhibition of exocytosis with an $IC_{50}$ of less than 50 nM, less than 5 nM, less than 0.5 nM, less than 0.05 nM, less than 0.005 nM, less than 0.0005 nM, less than 0.00005 nM or less than 0.000005 nM upon exposure to BoNT/C1. In still further embodiments, the invention provides a neuron containing a BoNT/D substrate which exhibits inhibition of exocytosis with an $IC_{50}$ of less than 50 nM, less than 5 nM, less than 0.5 nM, less than 0.05 nM, less than 0.005 nM, less than 0.0005 nM, less than 0.00005 nM or less than 0.000005 nM upon exposure to BoNT/D. In additional embodiments, the invention provides a neuron containing a BoNT/E substrate which exhibits inhibition of exocytosis with an $IC_{50}$ of less than 50 nM, less than 5 nM, less than 0.5 nM, less than 0.05 nM, less than 0.005 nM, less than 0.0005 nM, less than 0.00005 nM or less than 0.000005 nM upon exposure to BoNT/E. In yet further embodiments, the invention provides a neuron containing a BoNT/F substrate which exhibits inhibition of exocytosis with an $IC_{50}$ of less than 50 nM, less than 5 nM, less than 0.5 nM, less than 0.05 nM, less than 0.005 nM, less than 0.0005 nM, less than 0.00005 nM or less than 0.000005 nM upon exposure to BoNT/F. In further embodiments, the invention provides a neuron containing a BoNT/G substrate which exhibits inhibition of exocytosis with an $IC_{50}$ of less than 50 nM, less than 5 nM, less than 0.5 nM, less than 0.05 nM, less than 0.005 nM, less than 0.0005 nM, less than 0.00005 nM or less than 0.000005 nM upon exposure to BoNT/G. In still further embodiments, the invention provides a neuron containing a TeNT substrate which exhibits inhibition of exocytosis with an $IC_{50}$ of less than 50 nM, less than 5 nM, less than 0.5 nM, less than 0.05 nM, less than 0.005 nM, less than 0.0005 nM, less than 0.00005 nM or less than 0.000005 nM upon exposure to TeNT. It is understood that the same neuron can express two or more receptors for different clostridial toxin serotypes, with the same or a different $IC_{50}$ for each individual toxin serotype.

A variety of non-neuronal cells including primary and established cells also are useful in the invention. Such non-neuronal cells encompass primary cells; established cells; stably and transiently transfected cells; and tumor cells as well as cells of all species of origin including mammalian, murine, rat, primate and human cells. As non-limiting examples, non-neuronal cells useful in the invention include glandular cells such as pancreatic acinar cells, pancreatic β-islet cells, and insulinoma HIT or INS-1 cells; fibroblasts; muscle cells; and hepatocytes.

Non-neuronal cells useful in the invention further include, without limitation, any of the following primary or established cells: anterior pituitary cells; adrenal cells such as chromaffin cells of the adrenal medulla; stomach cells such as enterochromaffin-like cells; pancreatic cells such as pancreatic islet β-cells; ovarian cells such as steroid-producing ovarian cells; kidney cells such as inner medullary collecting duct (IMCD) cells; pancreatic acinar cells; platelets; neutrophils; eosinophils; mast cells; epithelial cells such as those of the apical plasma membrane; and cells involved in glucose transporter (GLUT4) translocation. As non-limiting examples, a non-neuronal cell useful in the invention can include a clostridial toxin substrate which has a SNAP-25 recognition sequence; such a non-neuronal cell can be, for example, a primary or established anterior pituitary cell; adrenal cell such as a chromaffin cell of the adrenal medulla; stomach cell such as an enterochromaffin-like cell; pancreatic cell such as a pancreatic islet β-cell; or ovarian cell such as a steroid-producing ovarian cell. As further non-limiting examples, a non-neuronal cell useful in the invention can include a clostridial toxin substrate which has a SNAP-23 recognition sequence; such a non-neuronal cell can be, for example, a kidney cell such as an inner medullary collecting duct (IMCD) cell; a pancreatic acinar cell; a platelet; a neutrophil; an eosinophil; a mast cell; an epithelial cell such as one of the apical plasma membrane; or a cell involved in glucose transporter (GLUT4) translocation. It is understood that these and a variety of other primary and established non-neuronal cells can be useful in the invention.

In one embodiment, the invention provides an established non-neuronal cell that includes a nucleic acid molecule encoding a clostridial toxin substrate that contains a donor fluorophore, an acceptor having an absorbance spectrum overlapping the emission spectrum of the donor fluorophore and a clostridial toxin recognition sequence containing a cleavage site, where the cleavage site intervenes between the donor fluorophore and the acceptor and where, under the appropriate conditions, resonance energy transfer is exhibited between the donor fluorophore and the acceptor. Such an established non-neuronal cell can be, for example, stably transfected with a nucleic acid molecule encoding a clostridial toxin substrate.

It is understood that cells that express endogenous or transfected clostridial toxin receptor can be identified by routine methods including direct and indirect assays for toxin uptake. Such methods can rely, for example, on labelled toxin such as fluorescently labeled or radiolabeled toxin. Such methods also can be performed, for example, with anti-toxin antibodies, which can be used to detect intracellular toxin, for example, by immunocytochemistry or western blotting. In addition, cells that express clostridial toxin receptor and, therefore, take up one or more clostridial toxins also can be identified by assaying for cleaved target protein. As an example, a western blot using an antibody that specifically recognizes SNAP-25$_{197}$, the cleaved product of BoNT/A, can be used to assay for uptake of BoNT/A. Further well known assays include detection of $^3$H-noradrenaline or other neurotransmitter secretion as a measure of inhibition of exocytosis in neurons, or the release of hormones from endocrine cells such as anterior pituitary cells or ovarian cells. It is understood that these and similar assays for intracellular toxin, toxin cleavage product, or toxin function can be useful in selecting a neuron or other cell useful in the compositions and methods of the invention.

The invention further provides a cell that incorporates a "composite" clostridial toxin substrate. Such a composite clostridial toxin substrate contains (a) a first member of a donor fluorophore-acceptor pair linked to a first partner of an affinity couple; and (b) a clostridial toxin recognition sequence containing a cleavage site, where the recognition sequence is linked to a second member of the donor fluorophore-acceptor pair and a second partner of the affinity couple, where the cleavage site intervenes between the second member of the donor fluorophore-acceptor pair and the second partner of the affinity couple, and where (a) and (b) are stably associated such that, under the appropriate conditions, resonance energy transfer is exhibited between the first and second members of the donor fluorophore-acceptor pair. Thus, a composite clostridial toxin substrate is, in effect, a bipartite clostridial toxin substrate in which the two parts are stably associated through the affinity couple. As for other clostridial toxin substrates, resonance energy transfer is altered upon cleavage of the composite substrate. It is understood that the clostridial toxin recognition sequences and cleavage sites described herein and well known in the art can be useful in composite clostridial toxin substrates.

The term "donor fluorophore-acceptor pair," as used herein, means a donor fluorophore and an acceptor that has an absorbance spectrum overlapping the emission spectrum of the donor fluorophore. Where the first member of the pair is a donor fluorophore, the second member of the pair will be an acceptor. Where the first member of the pair is an acceptor, the second member of the pair will be a donor fluorophore.

In one embodiment, the first member of the donor fluorophore-acceptor pair is a donor fluorophore, and the second member is an acceptor. In another embodiment, the first member of the donor fluorophore-acceptor pair is an acceptor, and the second member is a donor fluorophore. A variety of donor fluorophores and acceptors can be incorporated into a composite clostridial toxin substrate useful in a cell or method of the invention, including the donor fluorophores and acceptors described hereinbelow. In one embodiment, the donor fluorophore is a fluorescent protein. In another embodiment, the donor fluorophore and acceptor each is a fluorescent protein. Useful fluorescent proteins include but are not limited to green fluorescence protein (GFP), blue fluorescence protein (BFP), cyan fluorescence protein (CFP), yellow fluorescence protein (YFP) and red fluorescence protein (RFP).

The term "affinity couple," as used herein, means two molecules that are capable of forming a stable, non-covalent association. Affinity couples useful in a composite substrate include, without limitation, SNAP-25-syntaxin; VAMP-synaptotagmin; streptavidin-biotin; S peptide-S protein; receptor-ligand; dimeric receptors or other interacting proteins. In one embodiment, the affinity couple is SNAP-25-syntaxin. In another embodiment, the affinity couple is VAMP-synaptotagmin.

The present invention also provides a nucleic acid molecule that encodes a clostridial toxin substrate including a donor fluorophore; an acceptor having an absorbance spectrum overlapping the emission spectrum of the donor fluorophore; and a clostridial toxin recognition sequence containing a cleavage site that intervenes between the donor fluorophore and the acceptor, where resonance energy transfer is exhibited between the donor fluorophore and the acceptor under the appropriate conditions. The nucleic acid molecule encoding a clostridial toxin substrate can be linked, for example, to a regulatory element such as a constitutive regulatory element or inducible regulatory element such as, without limitation, a tetracycline regulated regulatory element or ecdysone inducible regulatory element. Genetically encoded donor fluorophores and acceptors useful in a genetically encoded clostridial toxin substrate of the invention include green fluorescence protein (GFP) and other fluorescent proteins disclosed herein below and known in the art.

In one embodiment, the encoded clostridial toxin recognition sequence is residues 34 to 206 of human SNAP-25 (SEQ ID NO: 4). In another embodiment, the encoded clostridial toxin recognition sequence is residues 34 to 206 of human SNAP-25 (SEQ ID NO: 4) and the donor fluorophore or acceptor is a green fluorescence protein. In other embodiments, the encoded clostridial toxin recognition sequence is residues 34 to 206 of human SNAP-25 (SEQ ID NO: 4), and the donor fluorophore and acceptor each are a green fluorescence protein, blue fluorescence protein, cyan fluorescence protein, yellow fluorescence protein, or red fluorescence protein.

A nucleic acid molecule of the invention can further optionally include any of a variety of constitutive or inducible regulatory elements such as promoters or enhancers. Inducible expression systems have the advantage that they can produce controlled intracellular levels of substrate. Constitutive regulatory elements useful in the invention include, without limitation, the cytomegalovirus (CMV), herpes simplex virus thymidine kinase (HSV TK), simian virus 40 (SV40) early, 5' long terminal repeat (LTR), elongation factor-1α (EF-1α) and polybiquitin (UbC) regulatory elements. Inducible regulatory elements useful in the invention include tetracycline inducible and tetracycline repressible elements such as Tet-On™ and Tet-Off™ (BD Biosciences); ecdysone-inducible elements and GAL4 regulated elements such as the GeneSwitch™ system (Invitrogen). The skilled person understands that these and other constitutive and inducible regulatory elements can be included a nucleic acid molecule of the invention.

Any of a variety of genetically encoded donor fluorophores and acceptors are useful in the nucleic acid molecules and cells of the invention. Such donor fluorophores and acceptors include genetically encoded dyes such as a green fluorescence protein (GFP), blue fluorescence protein (BFP), cyan fluorescence protein (CFP), yellow fluorescence protein (YFP) or red fluorescence protein such as dsRed (BD Biosciences Clontech; Palo Alto, Calif.). Such genetically encoded donor fluorophores and acceptors are well known in the art as described, for example, in Selvin, supra, 2000, and Mahajan et al., *Chemistry and Biology* 6:401-409 (1999). As an example, CFP has an excitation maxima at 433 nm and an emission maxima at 476 nm and can be used as a donor fluorophore in combination with YFP as an acceptor (emission maxima at 527 nm). If desired, BFP can be used as a donor fluorophore in combination with GFP as the acceptor, or CFP can be used as the donor fluorophore in combination with YFP as the acceptor. Additional genetically encoded donor fluorophores and acceptors including Aequorea related fluorescent proteins are well known in the art, as described, for example, in U.S. Pat. No. 5,981,200.

The invention further provides a cell that includes a genetically encoded clostridial toxin substrate. Thus, the invention provides a cell which includes a nucleic acid molecule encoding a clostridial toxin substrate that includes a donor fluorophore; an acceptor having an absorbance spectrum overlapping the emission spectrum of the donor fluorophore; and a clostridial toxin recognition sequence containing a cleavage site that intervenes between the donor fluorophore and the acceptor, where resonance energy transfer is exhibited between the donor fluorophore and the acceptor under the appropriate conditions. The nucleic acid molecule can encode, for example, residues 34 to 206 of human SNAP-25 (SEQ ID NO: 4), and can further include, for example, a donor fluorophore such as a green fluorescence protein, blue fluorescence protein, cyan fluorescence protein, yellow fluorescence protein, or red fluorescence protein, as well as an acceptor such as a green fluorescence protein, blue fluorescence protein, cyan fluorescence protein, yellow fluorescence protein, or red fluorescence protein.

Any of a variety of cells can be engineered to include a nucleic acid molecule encoding a clostridial toxin substrate, including, but not limited to, human cells, neuronal cells and non-neuronal cells. In one embodiment, the nucleic acid molecule encoding the clostridial toxin substrate is stably transfected into the cell. In another embodiment, the nucleic acid molecule encoding a clostridial toxin substrate is linked to a regulatory element such as a constitutive regulatory element or inducible regulatory element. A variety of inducible regulatory elements are useful in the invention, including, without limitation, tetracycline regulated regulatory elements and ecdysone inducible regulatory elements. A genetically encoded clostridial toxin substrate of the invention can include any of a variety of genetically encoded donor fluorophores or acceptors such as GFP. A cell containing a nucleic acid molecule encoding a clostridial toxin substrate can be prepared by any of a variety of routine methods including well-known transient and stable transfection methods. As non-limiting examples, routine techniques for introducing a nucleic acid molecule into a cell, including a neuronal or non-neuronal cell, include microinjection, electroporation, lipofection, calcium-phosphate mediated transfection, DEAE-Dextran-mediated transfection, polybrene- or polylysine-mediated transfection, and conjugation to an antibody, gramacidin S, artificial viral envelope or other intracellular carrier such as TAT. See Cibelli et al., *Nat. Biotech.* 16:642-646 (1998); Lamb and Gearhart, *Cur. Opin. Gen. Dev.* 5:342-348 (1995); Choi (U.S. Pat. No. 6,069,010); and *Current Protocols in Molecular Biology*, John Wiley and Sons, pp 9.16.4-9.16.11 (2000).

The present invention also provides kits for determining clostridial toxin activity in a sample. Such kits contain a substrate composition or cell of the invention in a vial or other container and generally also include instructions for use. In one embodiment, a kit of the invention further includes as a positive control a known amount of the botulinum or tetanus toxin capable of cleaving the clostridial toxin substrate which incorporated into the substrate composition or cell included in the kit. In another embodiment, the kit contains a substrate composition of the invention and further includes one or both cleavage products as a positive control. Such a kit can include, for example, a substrate composition of the invention and the corresponding cleavage product containing the donor fluorophore as a positive control. Where the invention provides a kit containing a cell of the invention and a positive control, the positive control is understood to be a cell of the same cell type, having one or both corresponding cleavage products in place of the uncleaved clostridial toxin substrate. Such a positive control cell can contain, for example, the cleavage product which includes the donor fluorophore.

As described further below, a combination of cells of the same or different types containing different clostridial toxin substrates can be useful for detecting the activity of two or more clostridial toxins. Thus, in one embodiment, the invention provides a kit for determining clostridial toxin activity that includes at least two substrate compositions of the invention having recognition sequences for two different clostridial toxins. In another embodiment, the invention provides a kit for determining clostridial toxin activity that includes at least two cells of the invention containing two different clostridial toxin substrates having recognition sequences for two different clostridial toxins.

The present invention also provides a method of determining clostridial toxin activity by (a) contacting with a sample a cell containing a clostridial toxin substrate that includes a donor fluorophore; an acceptor having an absorbance spectrum overlapping the emission spectrum of the donor fluorophore; and a clostridial toxin recognition sequence containing a cleavage site that intervenes between the donor fluorophore and the acceptor, where resonance energy transfer is exhibited between the donor fluorophore and the acceptor under the appropriate conditions; (b) exciting the donor fluorophore; and (c) determining resonance energy transfer of the contacted cell relative to a control cell, where a difference in resonance energy transfer of the contacted cell as compared to the control cell is indicative of clostridial toxin activity.

The methods of the invention can be advantageously practiced to assay a clostridial toxin for several different steps required for toxin activity. Thus, a method of the invention can be used to determine if a clostridial toxin has a functional binding domain for cellular uptake; a functional translocation domain for delivery of light chain to the cell cytosol; and a functional proteolytic domain. In the absence of any of these three functions, method of the invention generally yields a negative result.

In the methods of the invention, a clostridial toxin substrate optionally can be covalently linked to a delivery agent, which can be, for example, a protein, peptide or peptidomimetic. Useful delivery agents include, for example, antennapedia proteins or active fragments thereof, such as active fragments having the amino acid sequence RQIKIWFQNRRMKWKK (SEQ ID NO: 1); HIV TAT proteins or active fragments thereof, such as active fragments having the amino acid sequence YGRKKRRQRRR (SEQ ID NO: 2); and herpes simplex virus VP22 proteins or active fragments thereof, such as herpes simplex virus VP22 proteins having the amino acid sequence SEQ ID NO: 3, or active fragments thereof. In one embodiment, a method of the invention is practiced with a cell containing a chimeric protein, peptide or peptidomimetic that includes a clostridial toxin substrate and a delivery agent operatively fused to the substrate. Such a chimeric protein, peptide or peptidomimetic can have, for example, a length of at most 50 or 100 residues.

A clostridial toxin substrate useful in a method of the invention can be a botulinum toxin substrate of any serotype or a tetanus toxin substrate. Thus, a method of the invention can be practiced with a cell containing a BoNT/A substrate which includes a BoNT/A recognition sequence; a cell containing a BoNT/B substrate that includes a BoNT/B recognition sequence; a cell containing a BoNT/C1 substrate that includes a BoNT/C1 recognition sequence; a cell containing a BoNT/D substrate which includes a BoNT/D recognition sequence; a cell containing a BoNT/E substrate that includes a BoNT/E recognition sequence; a cell containing a BoNT/F substrate which includes a BoNT/F recognition sequence; a cell containing a BoNT/G substrate which includes a BoNT/G recognition sequence; or a cell containing a TeNT toxin substrate that includes a TeNT recognition sequence. It is understood that a variety of donor fluorophores and acceptors can be incorporated into a clostridial toxin substrate useful in a method of the invention. As non-limiting examples, useful donor fluorophores include Alexa Fluor®-488, DABCYL and BODIPY®, and useful acceptors include EDANS, QSY-7® and tetramethylrhodamine. As described further herein, acceptors useful in the methods of the invention encompass non-fluorescent acceptors as well as acceptor fluorophores, including acceptor fluorophores having a relatively long fluorescence lifetime of at least 1 microsecond.

A variety of cells are useful in the methods of the invention including, without limitation, primary cells; established cells; human cells; neurons such as primary neurons, established neurons and human neurons; and non-neuronal cells such as pancreatic acinar cells. Neurons useful for determining clostridial toxin activity according to a method of the invention include central nervous system neurons and peripheral neurons; as non-limiting examples, such a neuron can be a neuroblastoma cell, spinal cord neuron, dorsal root ganglion neuron, cerebral cortex neuron, cerebellar neuron, hippocampal neuron or motor neuron.

One skilled in the art understands that a variety of samples can be assayed for clostridial toxin activity according to a method of the invention. Such samples include, without limitation, crude cell lysates; isolated clostridial toxins; formulated clostridial toxin products such as BOTOX; and foodstuffs.

A variety of means can be used to determine resonance energy transfer subsequent to excitation of a donor fluorophore in a method of the invention. In one embodiment, a method of the invention includes the step of detecting donor fluorescence intensity of the contacted cell relative to a control cell, where increased donor fluorescence intensity of the contacted cell as compared to the control cell is indicative of clostridial toxin activity. In another embodiment, a method of the invention includes the step of detecting acceptor fluorescence intensity of the contacted cell relative to a control cell, where decreased acceptor fluorescence intensity of the contacted cell as compared to the control cell is indicative of clostridial toxin activity. In a further embodiment, a method of the invention includes the step of detecting an acceptor emission maximum and a donor fluorophore emission maximum of the contacted cell relative to a control cell, where a shift in emission maxima from near the acceptor emission maximum to near the donor fluorophore emission maximum is indicative of clostridial toxin activity. In yet a further embodiment, a method of the invention includes the step of detecting the ratio of fluorescence amplitudes near an acceptor emission maximum to the fluorescence amplitudes near a donor fluorophore emission maximum of the contacted cell relative to a control cell, where a decreased ratio in the contacted cell as compared to the control cell is indicative of clostridial toxin activity. In still another embodiment, a method of the invention includes the step of detecting the excited state lifetime of the donor fluorophore in the contacted cell relative to a control cell, where an increased donor fluorophore excited state lifetime in the contacted cell as compared to the control cell is indicative of clostridial toxin activity. If desired, the step of determining resonance energy transfer can be repeated at one or more later time intervals. In addition, conditions suitable for clostridial toxin activity can be optionally selected such that the assay is linear.

As discussed further below, it is understood that the methods of the invention are applicable to crude samples as well as highly purified dichain toxins. As non-limiting examples, a method of the invention can be useful to assay for clostridial toxin activity in a food or beverage sample; to assay a sample from a human or animal, for example, exposed to a clostridial toxin or having one or more symptoms of a clostridial toxin; to follow activity during production and purification of clostridial toxin, and to assay formulated clostridial toxin products, including pharmaceuticals and cosmetics.

A method of the invention can be used to determine the activity of any clostridial toxin. In one embodiment, a method of the invention relies on a cell containing a BoNT/A substrate to determine BoNT/A activity. Such a BoNT/A substrate can be any of the BoNT/A substrates described herein, for example, a BoNT/A substrate containing at least six consecutive residues of SNAP-25, where the six consecutive residues include Gln-Arg. In another embodiment, a method of the invention relies on a cell containing a BoNT/B substrate to determine BoNT/B activity. Such a BoNT/B substrate can be any of the BoNT/B substrates described herein, for example, a BoNT/B substrate containing at least six consecutive residues of VAMP, where the six consecutive residues include Gln-Phe. A method of the invention also can utilize a cell containing a BoNT/C1 substrate to determine BoNT/C1 activity. A BoNT/C1 substrate useful in a method of the invention can be any of the BoNT/C1 substrates described herein, for example, a BoNT/C1 substrate containing at least six consecutive residues of syntaxin, where the six consecutive residues include Lys-Ala, or containing at least six consecutive residues of SNAP-25, where the six consecutive residues include Arg-Ala.

In another embodiment, a method of the invention relies on a cell containing a BoNT/D substrate to determine BoNT/D activity. Such a BoNT/D substrate can be any of the BoNT/D substrates described herein, for example, a BoNT/D substrate containing at least six consecutive residues of VAMP, where the six consecutive residues include Lys-Leu. In a further embodiment, a method of the invention is practiced with a cell containing a BoNT/E substrate to determine BoNT/E activity. A BoNT/E substrate useful in a method of the invention can be any of the BoNT/E substrates described herein, for example, a BoNT/E substrate containing at least six consecutive residues of SNAP-25, where the six consecutive residues include Arg-Ile. In yet a further embodiment, a method of the invention relies on a cell containing a BoNT/F substrate to determine BoNT/F activity. A BoNT/F substrate useful in a method of the invention can be any of the BoNT/F substrates described herein, for example, a BoNT/F substrate containing at least six consecutive residues of VAMP, where the six consecutive residues include Gln-Lys.

A method of the invention also can utilize a cell containing a BoNT/G substrate to determine BoNT/G activity. A BoNT/G substrate useful in a method of the invention can be any of the BoNT/G substrates described herein, for example, a BoNT/G substrate containing at least six consecutive residues of VAMP, where the six consecutive residues include Ala-Ala. A method of the invention also can be useful to determine TeNT protease activity and, in this case, relies on a cell containing a TeNT substrate. Any of the TeNT substrates described herein can be useful in a method of the invention, for example, a TeNT substrate containing at least six consecutive residues of VAMP, where the six consecutive residues include Gln-Phe.

A variety of samples are useful in the methods of the invention. As used herein, the term "sample" means any biological matter that contains or potentially contains an active clostridial toxin. Thus, the term sample encompasses but is not limited to purified or partially purified clostridial toxin; recombinant single chain or dichain toxin with a naturally or non-naturally occurring sequence; recombinant clostridial toxin with a modified protease specificity; recombinant clostridial toxin with an altered cell specificity; chimeric toxin containing structural elements from multiple clostridial toxin species or subtypes; bulk toxin; formulated product; cells or crude, fractionated or partially purified cell lysates, for example, engineered to include a recombinant nucleic acid encoding a clostridial toxin; bacterial, baculoviral and yeast lysates; raw, cooked, partially cooked or processed foods; beverages; animal feed; soil samples; water samples; pond sediments; lotions; cosmetics; and clinical formulations. It further is understood that the term sample encompasses tissue samples, including, without limitation, mammalian tissue samples, livestock tissue samples such as sheep, cow and pig tissue samples; primate tissue samples; and human tissue samples. Such samples encompass, without limitation, intestinal samples such as infant intestinal samples, and tissue samples obtained from a wound.

The concentration of purified or partially purified clostridial toxin assayed in a method of the invention generally is in the range of about 0.0001 to 5000 ng/ml toxin, for example, about 0.001 to 5000 ng/ml, 0.01 to 5000 ng/ml, 0.1 to 5000 ng/ml, 1 to 5000 ng/ml, or 10 to 5000 ng/ml toxin, which can be, for example, purified recombinant dichain toxin or formulated clostridial toxin product containing human serum albumin and excipients. Generally, the amount of purified toxin assayed in a method of the invention is in the range of 0.1 pg to 10 μg. It is understood that purified, partially purified or crude samples can be diluted such that the sample is within a convenient range for assaying for clostridial toxin activity against a standard curve. Similarly, one skilled in the art understands that a sample can be diluted or the amount of sample otherwise limited, such that the assay is linear since, at increasingly high concentrations of toxin, linearity of the assay can be sacrificed.

One skilled in the art understands that, in a method of the invention, a cell can be contacted with clostridial toxin for any of a variety of lengths of time depending, in part, on the type of cell used, the affinity of the toxin receptor expressed and the amount and type of toxin assayed. As non-limiting examples, the cell can be contacted with toxin for up to one hour, two hours, four hours, eight hours, sixteen hours, 24 hours, 48 hours or 72 hours.

In a method of the invention, resonance energy transfer can be determined by a variety of means. In one embodiment, the step of determining resonance energy transfer includes detecting donor fluorescence intensity of the contacted cell, where increased donor fluorescence intensity of the contacted cell as compared to the control cell is indicative of clostridial toxin activity. In another embodiment, the step of determining resonance energy transfer includes detecting acceptor fluorescence intensity of the contacted cell, where decreased acceptor fluorescence intensity of the contacted cell as compared to the control cell is indicative of clostridial toxin activity. In a further embodiment, the step of determining resonance energy transfer includes detecting the acceptor emission maximum and the donor fluorophore emission maximum, where a shift in emission maxima from near an acceptor emission maximum to near a donor fluorophore emission maximum is indicative of clostridial toxin activity. In an additional embodiment, the step of determining resonance energy transfer includes detecting the ratio of fluorescence amplitudes near an acceptor emission maximum to fluorescence amplitudes near a donor fluorophore emission maximum, where a decreased ratio in the contacted cell as compared to the control cell is indicative of clostridial toxin activity. In yet a further embodiment, the step of determining resonance energy transfer is practiced by detecting the excited state lifetime of the donor fluorophore in the contacted cell, where an increased donor fluorophore excited state lifetime in the contacted cell as compared to the control cell is indicative of clostridial toxin activity.

In a method of the invention for determining clostridial toxin activity, a cell is contacted with a sample, the cell containing a clostridial toxin substrate that includes a first donor fluorophore, a first acceptor having an absorbance spectrum which overlaps the emission spectrum of the donor fluorophore, and a first clostridial toxin recognition sequence containing a cleavage site, where the cleavage site intervenes between the donor fluorophore and the acceptor and where, under the appropriate conditions, resonance energy transfer is exhibited between the donor fluorophore and the acceptor. If desired, a second clostridial toxin substrate can be included in the same cell; this second substrate contains a second donor fluorophore and second acceptor having an absorbance spectrum which overlaps the emission spectrum of the second donor fluorophore, and a second clostridial toxin recognition sequence that is cleaved by a different clostridial toxin than the toxin that cleaves the first clostridial toxin recognition sequence. The donor fluorophore-acceptor pair in the second substrate can be the same or different from the donor fluorophore-acceptor pair in the first substrate. In this way, a single sample conveniently can be assayed for the presence of more than one clostridial toxin.

It is understood that one can assay for any combination of clostridial toxins, for example, two, three, four, five, six, seven, eight, or more clostridial toxins. One can assay, for example, any combination of two, three, four, five, six, seven or eight of BoNT/A, BoNT/B, BoNT/C1, BoNT/D, BoNT/E, BoNT/F, BoNT/G and TeNT. As an example, seven cells of the same of different types, selected as described hereinabove, which contain seven substrates, each of which includes fluorescein and tetramethylrhodamine flanking a BoNT/A, BoNT/B, BoNT/C1, BoNT/D, BoNT/E, BoNT/F or BoNT/G recognition sequence and cleavage site. These cells each are contacted with a sample under conditions suitable for botulinum toxin activity before exciting the donor fluorescein at an absorption wavelength of about 488 nm and determining energy transfer. A shift in the emission maximum of the acceptor, tetramethylrhodamine (585 nm) to that of fluorescein (520 nm) is indicative of activity of at least one botulinum toxin. Such an assay can be useful, for example, for assaying food samples or tissue samples for the presence of any botulinum or other clostridial toxin and can be combined, if desired, with one or more subsequent assays for individual clostridial toxins or specific combinations of clostridial toxins.

In another embodiment, a single sample is assayed for two or more different clostridial toxins using two or more different clostridial toxin substrates contained in the same or different cells such as neurons, with each substrate containing a different donor fluorophore-acceptor pair. The use of multiple substrates can be useful for extending the dynamic range of an assay, as described, for example, in U.S. Pat. No. 6,180,340. As an example of the use of multiple clostridial toxin substrates, a single sample can be assayed for BoNT/A and BoNT/B activity using a cell containing first and second clostridial toxin substrates: the first clostridial toxin substrate contains the donor fluorophore fluorescein and the acceptor tetramethylrhodamine with an intervening BoNT/A recognition sequence and cleavage site, and the second clostridial toxin substrate contains the donor fluorophore EDANS and the acceptor DABCYL with an intervening BoNT/B recognition sequence and cleavage site. The first donor fluorophore, fluorescein, is excited at about 488 nm, and energy transfer is determined, with an increase in the fluorescence intensity of fluorescein (at about 520 nm) indicative of BoNT/A activity. The second donor fluorophore, EDANS, is excited at an absorption wavelength of about 340 nm, with an increase in the fluorescence intensity of EDANS (at about 490 nm) indicative of BoNT/B activity. Similarly, where two or more different donor fluorophores are to be used together to assay a single sample, one can combine, for example, any combination or all of the following lanthanides: terbium, dysprosium, europium and samarium (EG&G Wallac). These lanthanides have spectra that are clearly distinguishable on the basis of decay time and wavelength. Those skilled in the art understand that the first donor fluorophore can be excited before, at the same time, or after excitation of the second donor fluorophore, and that energy transfer of the first substrate can be determined before, at the same time, or after determining energy transfer of the second substrate.

The methods of the invention involve exciting a donor fluorophore which is incorporated into a clostridial toxin substrate within a cell. One skilled in the art understands that a donor fluorophore generally is excited at or near the optimal absorption wavelength (excitation wavelength) of the donor fluorophore. As an example, where the donor fluorophore is fluorescein, the donor can be excited, for example, at or near the optimal absorption wavelength of 488 nm.

Proteolysis of the clostridial toxin substrate, and hence clostridial toxin activity, can be detected by a variety of means, for example, by detecting increased donor fluorescence intensity; decreased acceptor fluorescence intensity; a shift in emission maxima from near the acceptor emission maximum to near the donor fluorophore emission maximum; a decreased ratio of fluorescence amplitudes near the acceptor emission maximum to the fluorescence amplitudes near the donor fluorophore emission maximum; or an increased donor fluorophore excited state lifetime. It is understood that the relevant fluorescence intensities or excited state lifetimes are detected at the appropriate wavelength or range of wavelengths. As an example, where donor fluorescence intensity is detected, the appropriate wavelength is at or near the emission maxima of the donor fluorophore, or is a range of wavelengths encompassing or near to the emission maxima of the donor fluorophore.

It is recognized that changes in the absolute amount of clostridial toxin substrate in the cell, excitation intensity, and turbidity or other background absorbance at the excitation wavelength effects the fluorescence intensities of donor and acceptor fluorophores roughly in parallel. Thus, it is understood that a ratio of emission intensities is independent of the absolute amount of substrate, excitation intensity, and turbidity or other background absorbance, and can be a useful indicator of clostridial toxin activity. Similarly, one skilled in the art understands that the excitation state lifetime of a donor fluorophore is independent of the absolute amount of substrate, excitation intensity, and turbidity or other background absorbance and can be useful in a method of the invention.

In one embodiment, a method of the invention is practiced by detecting donor fluorescence intensity, with increased donor fluorescence intensity indicative of clostridial toxin activity. Such increased intensity can be, for example, at least two-fold, three-fold, five-fold, ten-fold, twenty-fold or more relative to fluorescence intensity at the same wavelength of the same or similar cell not contacted with sample.

For detection of donor fluorescence intensity, excitation is set at the wavelength of donor fluorophore absorption, and the emission of the donor fluorophore is monitored. The emission wavelength of the donor fluorophore generally is selected such that little or no contribution from acceptor fluorescence is observed. The presence of acceptor quenches donor fluorescence. Energy transfer efficiency, E, is calculated from $E=1-I_{DA}/I_D$, where $I_{DA}$ and $I_D$ are donor intensities in the presence and absence of acceptor. Both are normalized to the same donor fluorophore concentration. If desired, time resolved measurements, for which donor fluorophore concentration is not required, can be performed using $E=1-\{T_{DA}\}/T_D$, where $\{T_{DA}\}$ and $\{T_D\}$ are amplitude-averaged lifetimes of donor fluorophore in the presence and absence of acceptor.

In one embodiment, the invention is practiced by detecting a shift in emission maxima from near the acceptor emission maximum to near the donor fluorophore emission maximum as a determination of resonance energy transfer. As an example, where a tetramethylrhodamine acceptor is combined with the donor fluorophore fluorescein, one can detect a shift from predominantly red emission to predominantly green emission as an indicator of decreased resonance energy transfer and, therefore, of clostridial toxin activity. It is understood that the observed shift in emission maxima generally will not be a complete shift but that only part of the emission intensity will be shifted to near the donor fluorophore emission maximum.

In several methods of the invention, resonance energy transfer of the contacted cell is determined relative to a control cell. Such a control cell generally is a cell of the same or similar type as the contacted cell and grown under the same conditions but which is not contacted with any sample or is contacted with a defined negative sample or a defined positive sample. One skilled in the art understands that a variety of control cells are useful in the methods of the invention and that a control cell can be a positive control cell or a negative control cell. A control cell can be, for example, a negative control cell such as a similar or identical cell containing the same or similar clostridial toxin substrate that is contacted with a similar, defined negative sample, which is known to lack active clostridial toxin, or that is not contacted with any sample. A control cell also can be, for example, a positive control cell such as a cell containing one or both cleavage products that result from proteolysis of the clostridial toxin substrate at the cleavage site or a cell containing the same or similar substrate contacted with a defined positive sample, which is known to include active clostridial toxin. Positive control cells include cells containing the donor fluorophore-containing cleavage product, cells containing the acceptor-containing cleavage product, and cells containing both cleavage products.

The methods of the invention for determining clostridial toxin activity involve determining resonance energy transfer of a cell containing a clostridial toxin substrate contacted with a sample relative to a control cell and can be practiced as "fixed-time" assays or as continuous time assays. Thus, in one embodiment, the FRET determination is repeated at one or more later time intervals. Fluorescence resonance energy transfer can be determined, for example, at two or more, five or more, ten or more, or twenty or more different times. Fluorescence intensities and other indicators of FRET also can be detected continuously by well known methods (see, for example, Wang et al., supra, 1993; Holskin et al., supra, 1995; and Kakiuchi et al., supra, 1999).

In a method of the invention, fluorescence of a contacted cell typically is determined using a fluorimeter. In general, excitation radiation from an excitation source having a first wavelength passes through excitation optics. The excitation optics cause the excitation radiation to excite the substrate in the cell. In response, fluorophores in the substrate emit radiation which has a wavelength that is different from the excitation wavelength. Collection optics then collect the emission; if desired, the device includes a temperature controller to maintain the cell at a specific temperature while being scanned. If desired, a multi-axis translation stage moves a microtiter plate containing a plurality of samples in order to position different wells to be exposed. It is understood that the multi-axis translation stage, temperature controller, auto-focusing feature, and electronics associated with imaging and data collection can be managed by the appropriate digital computer.

It is further understood that the methods of the invention can be automated and can be configured in a high-throughput or ultra high-throughput format using, without limitation, 96-well, 384-well or 1536-well plates. As one example, fluorescence emission can be detected using the Molecular Devices FLIPR instrumentation system (Molecular Devices; Sunnyvale, Calif.), which is designed for 96-well plate assays (Schroeder et al., *J. Biomol. Screening* 1:75-80 (1996)).

FLIPR utilizes a water-cooled 488 nm argon ion laser (5 watt) or a xenon are lamp and a semiconfocal optimal system with a charge-coupled device (CCD) camera to illuminate and image the entire plate. The FPM-2 96-well plate reader (Folley Consulting and Research; Round Lake, Ill.) also can be useful in detecting fluorescence emission in the methods of the invention. One skilled in the art understands that these and other automated systems with the appropriate spectroscopic compatibility such as the ECLIPSE cuvette reader (Varian-Cary; Walnut Creek, Calif.), the SPECTRA$_{max}$ GEMINI XS (Molecular Devices) and other systems from, for example, Perkin Elmer can be useful in the methods of the invention.

The methods of the invention can be practiced, if desired, in vivo; as non-limiting examples, the methods of the invention can be practiced in a mouse, rat, worm or fish. An in vivo method of the invention for determining clostridial toxin activity can be practiced by (a) administering to an animal a substrate composition containing a delivery agent and a clostridial toxin substrate that includes a donor fluorophore; an acceptor having an absorbance spectrum overlapping the emission spectrum of the donor fluorophore; and a clostridial toxin recognition sequence containing a cleavage site that intervenes between the donor fluorophore and the acceptor, where resonance energy transfer is exhibited between the donor fluorophore and the acceptor under the appropriate conditions; (b) treating the animal with a sample; (c) exciting the donor fluorophore; and (d) determining resonance energy transfer of the treated animal relative to a control animal, where a difference in resonance energy transfer of the treated animal as compared to the control animal is indicative of clostridial toxin activity. As an example, an HIV TAT based delivery agent has been shown to efficiently deliver a target protein in vivo (Schwartz et al., *Science* 285:1569-1572 (1999)). In one embodiment, an in vivo method of the invention is practiced with a substrate composition which includes an HIV TAT derived delivery agent. In a further embodiment, the substrate composition is administered into the spinal cord of the animal. In yet a further embodiment, the persistence of toxin activity over time is assayed by determining resonance energy transfer two or more times.

The present invention relies, in part, on FRET, which is a physical process whereby energy is transferred non-radiatively from an excited donor fluorophore to an acceptor, which may be another fluorophore, through intramolecular long-range dipole-dipole coupling. FRET is dependent on the inverse sixth power of the intramolecular separation of the donor fluorophore and acceptor, and for effective transfer, the donor fluorophore and acceptor are in close proximity, separated, for example, by about 10 A to about 100 A. Effective energy transfer is dependent on the spectral characteristics of the donor fluorophore and acceptor as well as their relative orientation. For effective transfer over 10 to 100 A, the quantum yield of the donor fluorophore generally is at least 0.1, and the absorption coefficient of the acceptor generally is at least 1000 (see Clegg, *Current Opinion in Biotech.* 6:103-110 (1995); and Selvin, *Nature Structural Biol.* 7:730-734 (2000)).

In a clostridial toxin substrate useful in the invention, the donor fluorophore and acceptor are selected so that the donor fluorophore and acceptor exhibit resonance energy transfer when the donor fluorophore is excited. One factor to be considered in choosing the donor fluorophore/acceptor pair is the efficiency of FRET between the donor fluorophore and acceptor. In one embodiment, the invention relies on a clostridial toxin substrate in which, under optimal conditions, the efficiency of FRET between the donor fluorophore and acceptor is at least 10%. In another embodiment, the invention relies on a clostridial toxin substrate in which, under optimal conditions, the efficiency of FRET between the donor fluorophore and acceptor is at least 20%. In still further embodiments, the invention relies on a clostridial toxin substrate in which, under optimal conditions, the efficiency of FRET between the donor fluorophore and acceptor is at least 30%, 40%, 50%, 60%, 70% or 80%.

As is well known in the art, the efficiency of FRET is dependent on the separation distance and the orientation of the donor fluorophore and acceptor as described by the Förster equation, as well as the fluorescent quantum yield of the donor fluorophore and the energetic overlap with the acceptor. In particular, the efficiency (E) of FRET can be determined as follows:

$$E = 1 - F_{DA}/F_D = 1/(1+(R/R_0)^6)$$

where $F_{DA}$ and $F_D$ are the fluorescence intensities of the donor fluorophore in the presence and absence of the acceptor, respectively, and R is the distance between the donor fluorophore and the acceptor.

The Förster radius ($R_o$) is the distance at which resonance energy transfer is 50% efficient, that is, 50% of excited donor fluorophores are deactivated by FRET. The magnitude of the Förster radius depends on the quantum yield of the donor fluorophore; the extinction coefficient of the acceptor; and the overlap between the donor fluorophore's emission spectrum and the acceptor's excitation spectrum.

$$R_O = [8.8 \times 10^{23} \times K^2 \times n^{-4} \times QY_D \times J(\lambda)]^{1/6} \text{Å}$$

where $K^2$=dipole orientation factor (range 0 to 4; $K^2 = 2/3$ for randomly oriented donors and acceptors)

$QY_D$=fluorescence quantum yield of the donor in the absence of the acceptor n=refractive index $$J(\lambda) = \text{spectral overlap integral}$$
$$= \int \varepsilon_A(\lambda) \times F_D(\lambda) \times \lambda^4 d\lambda \quad cm^3 M^{-1}$$

where $\varepsilon_A$=extinction coefficient of acceptor $F_D$=fluorescence emission intensity of donor as a fraction of the total integrated intensity (Förster, *Ann. Physik* 2:55-75 (1948)).

Typical Förster radius values for various donor fluorophore/acceptor pairs are given in Table B below (see, also, Wu and Brand, *Analytical Biochem.* 218:1-13 (1994)). Comprehensive lists of Förster radii also are known in the art (see, for example, Berlman, *Energy Transfer Parameters of Aromatic Compounds* Academic Press, New York 1973). Furthermore, those skilled in the art recognize that component factors of the Förster radius ($R_o$) are dependent upon the environment such that the actual value observed can vary from the listed value.

Any of a number of donor fluorophores and acceptors in various combinations can be included in a clostridial toxin substrate useful in the invention. A donor fluorophore generally is selected such that there is substantial spectral overlap between the emission spectrum of the donor fluorophore and the excitation spectrum of the acceptor. In addition, a donor fluorophore can be selected, for example, to have an excitation maximum near a convenient laser frequency such as Helium-Cadmium 442 nm or argon 488 nm, since laser light serves as a convenient and effective means to excite the donor fluorophore. In one embodiment, the wavelength maximum of the emission spectrum of the acceptor moiety is at least 10 nm greater than the wavelength maximum of the excitation spectrum of the donor fluorophore. In a further embodiment, the acceptor is a fluorophore having an emission spectrum in the red portion of the visible spectrum. In an additional embodiment, the acceptor is a fluorophore having an emission spectrum in the infrared region of the spectrum. A variety of donor fluorophore-acceptor pairs, and their Förster radii, are provided herein in Tables B and C. See, also, Haugland, *Handbook of Fluorescent Probes and Research Chemicals* $6^{th}$ Edition, Molecular Probes, Inc., Eugene, Oreg. 1996.

TABLE B

Exemplary Donor Fluorophores and Acceptors

| Donor fluorophore | Acceptor | Ro (Å) | Reference |
|---|---|---|---|
| Fluorescein | TMR | 49-54 | Johnson et al., Biochemistry 32: 6402-6410 (1993); Odom et al., Biochemistry 23: 5069-5076 (1984) |
| Fluorescein | QSY ® 7 | 61 | — |
| EDANS | DABCYL | 33 | — |
| Napthalene | Dansyl | 22 | Haas et al., Proc. Natl. Acad. Sci. USA 72: 1807-1811 (1975) |
| IANBD | DDPM | 25 | Kasprzyk et al., Biochemistry 22: 1877-1882 (1983) |
| IAEDANS | DDPM | 25-29 | Dalbey et al., Biochemistry 22: 4696-4706 (1983); Cheung et al., Biophys. Chem. 40: 1-17 (1991) |
| DNSM | LY | 26-32 | Nalin et al., Biochemistry 28: 2318-2324 (1985) |
| IAEDANS | IANBD | 27-51 | Franzen et al., Biochemistry 19: 6080-6089 (1980); First et al., Biochemistry 28: 3606-3613(1989) |
| ε-A | $F_2$DNB | 29 | Perkins et al., J. Biol. Chem. 259: 8786-8793 (1984) |
| Pyrene | Bimane | 30 | Borochov-Neori and Montal, Biochemistry 28: 1711-1718 (1989) |
| ANAI | IPM | 30 | Peerce and Wright, Proc. Natl. Acad. Sci. USA 83: 8092-8096 (1986) |
| IAANS | IAF | 31 | Grossman, Biochim. Biophys. Acta 1040: 276-280 (1990) |
| ε-A | $F_2$DPS | 31 | Perkins et al., supra, 1984 |
| ε-A | DDPM | 31 | Miki and Mihashi, Biochim. Biophys. Acta 533: 163-172 (1978) |
| IAEDANS | TNP | 31-40 | Takashi et al., Biochemistry 21: 5661-5668 (1982); dos Remedios and Cooke, Biochim. Biophys. Acta 788: 193-205 (1984) |
| MNA | DACM | 32 | Amir and Haas, Biochemistry 26: 2162-2175 (1987) |
| PM | NBD | 32 | Snyder and Hammes, Biochemistry 24: 2324-2331 (1985) |
| FITC | TNP-ATP | 32 | Amler et al., Biophys. J. 61: 553-568 (1992) |
| DANZ | DABM | 34 | Albaugh and Steiner, J. Phys. Chem. 93: 8013-8016 (1989) |
| NCP | CPM | 34 | Mitra and Hammes, Biochemistry 28: 3063-3069 (1989) |
| NAA | DNP | 33-37 | McWherter et al., Biochemistry 25: 1951-1963 (1986) |
| LY | TNP-ATP | 35 | Nalin, supra, 1985 |
| IAF | diI-$C_{18}$ | 35 | Shahrokh et al., J. Biol. Chem. 266: 12082-12089 (1991) |
| IAF | TMR | 37 | Taylor et al., J. Cell Biol. 89: 362-367 (1981) |
| FMA | FMA | 37 | Dissing et al., Biochim. Biophys. Acta 553: 66-83 (1979) |
| PM | DMAMS | 38 | Lin and Dowben, J. Biol. Chem. 258: 5142-5150 (1983) |
| mBBR | FITC | 38 | Tompa and Batke, Biochem. Int. 20: 487-494 (1990) |
| mBBR | DABM | 38 | Kasprzak et al., Biochemistry 27: 4512-4523 (1988) |
| ε-A | NBD | 38 | Miki and Iio, Biochim. Biophys. Acta 790: 201-207 (1984) |
| Pyrene | Coumarin | 39 | Borochov-Neori and Montal, supra, 1989 |
| IPM | FNAI | 39 | Peerce and Wright, supra, 1986 |
| IAEDANS | DABM | 40 | Tao et al. Biochemistry 22: 3059-3066 (1983) |
| IAEDANS | TNP-ATP | 40 | Tao et al., supra, 1983 |
| ε-A | IANBD | 40 | Miki and Wahl, Biochim. Biophys. Acta 786: 188-196 (1984) |
| NBD | SRH | 40-74 | Wolf et al., Biochemistry 31: 2865-2873 (1992) |
| ISA | TNP | 42 | Jacobson and Colman, Biochemistry 23: 3789-3799 (1984) |
| Dansyl | ODR | 43 | Lu et al., J. Biol. Chem. 264: 12956-12962 (1989) |
| DANZ | IAF | 44-49 | Cheung et al., Biochemistry 21: 5135-5142 (1983) |
| FNAI | EITC | 45 | Peerce and Wright, supra, 1986 |
| NBD | LRH | 45-70 | Wolf et al., supra, 1992 |
| IAF | EIA | 46 | Taylor et al., supra, 1981 |
| FITC | ENAI | 46 | Peerce and Wright, supra, 1986 |

TABLE B-continued

Exemplary Donor Fluorophores and Acceptors

| Donor fluorophore | Acceptor | Ro (Å) | Reference |
|---|---|---|---|
| Proflavin | ETSC | 46 | Robbins et al., Biochemistry 20: 5301-5309 (1981) |
| CPM | TNP-ATP | 46 | Snyder and Hammes, supra, 1985 |
| IAEDANS | IAF | 46-56 | Franzen, supra, 1985; Grossman, supra, 1990 |
| CPM | Fluorescein | 47 | Thielen et al., Biochemistry 23: 6668-6674 (1984) |
| IAEDANS | FITC | 49 | Jona et al., Biochim. Biophys. Acta 1028: 183-199 (1990); Birmachu et al., Biochemistry 28: 3940-3947 (1989) |
| IAF | TMR | 50 | Shahrokh et al., J. Biol. Chem. 266: 12082-12089 (1991) |
| CF | TR | 51 | Johnson et al., supra, 1993 |
| CPM | TRS | 51 | Odom et al., supra, 1984 |
| ε-A | TNP-ATP | 51 | dos Remedios and Cooke, supra, 1984 |
| CPM | FM | 52 | Odom et al., supra, 1984 |
| LY | EM | 53 | Shapiro et al., J. Biol. Chem. 266: 17276-17285 (1991) |
| FITC | EITC | 54 | Carraway et al., J. Biol. Chem. 264: 8699-8707 (1989) |
| IAEDANS | DiO-$C_{14}$ | 57 | Shahrokh et al., supra, 1991 |
| IAF | ErITC | 58 | Amler et al., supra, 1992 |
| FITC | EM | 60 | Kosk-Kosicka et al., J. Biol. Chem. 264: 19495-19499 (1989) |
| FITC | ETSC | 61-64 | Robbins et al., supra, 1981 |
| FITC | ErITC | 62 | Amler et al., supra, 1992 |
| BPE | CY5 | 72 | Ozinskas et al., Anal. Biochem. 213: 264-270 (1993) |
| Fluorescein | Fluorescein | 44 | — |
| BODIBY FL ® | BODIPY FL ® | 57 | — |

ANAI, 2-anthracence N-acetylimidazole;
BPE, B-phycoerythrin;
CF, carboxyfluorescein succinimidyl ester;
CPM, 7-diethylamino-3-(4'-maleimidylphenyl)-4-methylcoumarin;
CY5, carboxymethylindocyanine-N-hydroxysuccinimidyl ester;
diI-$C_{18}$, 1,1'-dioctadecyl-3-3,3,3',3'-tetramethyl-indocarbocyanine;
diO-$C_{14}$, 3,3'-ditetradecyloxacarbocyanine;
DABM, 4-dimethylaminophenylazo-phenyl-4'-maleimide;
DACM, (7-(dimethylamino)coumarin-4-yl)-acetyl;
DANZ, dansylaziridine;
DDPM, N-(4-dimethylamino-3,5-dinitrophenyl)maleimide;
DMAMS, dimethylamino-4-maleimidostilbene;
DSMN, N-(2,5'-dimethoxystiben-4-yl)-maleimide;
DNP, 2,4-dinitrophneyl;
ε-A, 1,$N^6$-ethenoadenosine;
EIA, 5-(iodoacetetamido)eosin;
EITC, eosin-5-isothiocyanate;
ENAI, eosin N-acETYLIMIDAZOLE;
EM, eosin maleimide;
ErITC, erythrosin-5'-isothiocyanate;
ETSC, eosin thiosemicarazide;
$F_2$DNB, 1,5-difluro-2,4'-dinitrobenzene;
$F_2$DPS, 4,4'-difluoro-3,3'-dinitrophenylsulfone;
FITC, fluorescein thiosemicarbazide;
IAANS, 2-(4'-iodoacetamido)anilino)napthalene-6-sulfonic acid;
IAEDANS, 5-(2-((iodoacetyl)amino)ethyl)amino)-napthlene-1-sulfonic acid;
IAF, 5-iodoacetamidofluorescein;
IANBD, N-((2-(iodoacetoxy)ethyl)-N-methyl)amino-7-nitrobenz-2-oxa-1,3-diazole;
IPM, 3(4-isothiocyanatophenyl)7-diethyl-4-amino-4-methylcoumarin;
ISA, 4-(iodoacetamido)salicylic acid;
LRH, lissaminerhodamine;
LY, Lucifer yellow;
mBBR, monobromobiamane;
MNA, (2-methoxy-1-naphthyl)-methyl;
NAA, 2-napthoxyacetic acid;
NBD, 7-nirto-2,1,3-benzoxadiazol-4-yl;
NCP, N-cyclohexyl-N'-(1-pyrenyl)carbodiimide;
ODR, octadecylrhodamine;
PM, N-(1-pyrene)-maleimide;
SRH, sulforhodamine;
TMR, tetramethylrhodamine;
TNP, trinitrophenyl; and
TR, Texas Red An aromatic amino acid such as tryptophan or tyrosine also can be a donor fluorophore useful in a clostridial toxin substrate and the compositions and methods disclosed herein. Exemplary donor fluorophore-acceptor pairs in which tryptophan or tyrosine is the donor fluorophore and relevant Förster distances are shown in Table C below. Modified amino acids also can be useful as donor fluorophores or acceptors in a clostridial toxin substrate useful in the invention. Such fluorescent or quenching modified amino acids are known in the art and include, for example, the fluorescent amino acid L-pyrenylalanine (Pya) and the non-fluorescent acceptor p-nitrophenylalanine (Nop), as described, for example, in Anne et al., *Analytical Biochem.* 291:253-261 (2001).

erally results in fluorescein becoming the dominant emitting fluorophore. Methods for preparing proteins and peptides containing fluorescein and tetramethylrhodamine are well known in the art (see, for example, Matsumoto et al., *Bioorg. Med. Chem. Letters* 10:1857-1861 (2000)).

A donor fluorophore useful in a clostridial toxin substrate also can be, for example, EDANS ($\lambda_{Ab}$ 340 nM, $\lambda_{Em}$ 490 nm), which can be combined with an acceptor such as DABCYL. Where DABCYL and EDANS are combined in a clostridial toxin substrate, energy is transferred from the EDANS donor fluorophore to the DABCYL acceptor in the intact substrate, resulting in quenching of EDANS emission fluorescence. Upon cleavage at the toxin cleavage site, fluorescence of the

TABLE C

Förster Distances Using Trp as a Donor

| Donor | Acceptor | $R_o$ (Å) | Reference |
|---|---|---|---|
| Trp | Ru(III)(NH3)5 | 12-16 | Recchia et al., Biochim. Biophys. Acta 702: 105-111 (1982) |
| Trp | Nitrobenzoyl | 16 | Wiczk et al., J. Fluo 1: 273-286 (1991) |
| Trp | Dansyl | 21 | Steinberg, Annu. Rev. Biochem. 40: 83-114 (1971) |
| Trp | IAEDANS | 22 | Matsumoto and Hammes, Biochemistry 14: 214-224 (1975) |
| Trp | ANS | 23 | Conrad and Brand, Biochemistry 7: 777-787 (1968) |
| Trp | Anthroyloxy | 24 | Wiczk et al., supra, 1991 |
| Trp | TNB | 24 | Wu and Brand, Biochemistry 31: 7939-7947 (1992) |
| Trp | Anthroyl | 25 | Burgun et al., Arch. Biochem. Biophys. 286: 394-401 (1991) |
| Trp | Tyr-NO$_2$ | 26 | Steiner et al., J. Fluo. 1: 15-22 (1991) |
| Trp | Pyrene | 28 | Vekshin, Mol. Biol. 17: 827-832 (1983) |
| Trp | Heme | 29 | Ladokhin et al., Proc. SPIE 1640: 562-569 (1992) |
| Trp | NBS | 30 | Wiczk et al., supra, 1991 |
| Trp | DNBS | 33 | Wiczk et al., supra, 1991 |
| Trp | DPH | 40 | Le Doan et al., Biochim. Biophys. Acta 735: 259-270 (1983) |

In view of the above, it is understood that a variety of donor fluorophore/acceptor pairs can be included in a clostridial toxin substrate useful in the invention. A donor fluorophore-acceptor pair useful in a clostridial toxin substrate can be, for example, the donor fluorophore fluorescein in combination with rhodamine; texas red; eosin; ROX (6-carboxy-X-rhodamine; Applied Biosystems Division of Perkin-Elmer Corporation; Foster City, Calif.); or TAMRA (N,N,N',N'-tetramethyl-6-carboxy-rhodamine; Applied Biosystems). A donor fluorophore-acceptor pair useful in the invention also can be, for example, the donor fluorophore cascade blue with fluorescein as an acceptor; the donor fluorophore BODIPY®-530/550 (4,4-difluoro-5,7-diphenyl-4-bora-3a,4a-diaza-S-indacene) in combination with BODIPY®-542/563 (4,4-difluoro-5-p-methoxyphenyl-4-bora-3a,4a-diaza-S-indacene) as an acceptor; or BODIPY®-542/563 in combination with BODIPY®-564/570 (4,4-difluoro-5-styryl-4-bora-3a,4a-diaza-5-indacene) as an acceptor. It is understood that the numbers following the name BODIPY®reflect the excitation and emission maxima of the molecule; BODIPY® compounds are commercially available from Molecular Probes (Eugene, Oreg.).

Clostridial toxin substrates useful in the invention include those in which the donor fluorophore is fluorescein. In one embodiment, the clostridial toxin substrate includes fluorescein as the donor fluorophore and tetramethylrhodamine as the acceptor. Such a substrate can be excited in the range of 480 to 505 nm, for example, at 488 nm or 492 nm, and emission detected at 520 nm ($\lambda_{em}$ fluorescein), 585 nm ($\lambda_{em}$ tetramethylrhodamine), or both. Prior to cleavage of the substrate at the clostridial toxin cleavage site, the tetramethylrhodamine emission intensity is greater than that of fluorescein; substrate cleavage results in a change in the ratio of fluorescein to tetramethylrhodamine intensity. Cleavage gen-cleaved EDANS product is increased and can be restored, for example, to the free donor fluorophore level. Efficient fluorescence quenching in the intact substrate occurs as a result of favorable energetic overlap of the EDANS emission spectrum and the DABCYL absorbance spectrum, and the relatively long excited state lifetime of the EDANS donor fluorophore (Wang et al., *Tetrahedron Lett.* 31:6493-6496 (1991); Holskin et al., *Anal. Biochem.* 226:148-155 (1995); and Wang et al., *Anal. Biochem.* 210:351-359 (1993)).

Dansyl (DNS or 5-dimethylaminonaphthalene-1-sulfonyl) also can be a useful as a donor fluorophore or acceptor in a clostridial toxin substrate. In one embodiment, the clostridial toxin substrate includes dansyl as the donor fluorophore; a dansyl donor can be combined, for example, with a nitrophenyl residue acceptor such as Phe(pNO2), which acts as a quencher when in proximity to the dansyl donor fluorophore. Substrates containing a dansyl donor fluorophore, for example, in combination with a nitrophenyl residue can be prepared as described, for example, in Florentin et al., *Anal. Biochem.* 141:62-69 (1984), or Goudreau et al., *Anal. Biochem.* 219:87-95 (1994). In another embodiment, the clostridial toxin substrate contains dansyl as the acceptor. A dansyl acceptor can act as a quencher when combined, for example, with a donor fluorophore such as Trp ($\lambda_{ex}$ 290 nm, $\lambda_{em}$ 360 nm). In a clostridial toxin substrate containing Trp and dansyl, Trp fluorescence can be quenched 60% by energy transfer to the dansyl group, and this quenching can be significantly reduced or abolished in the presence of toxin protease activity at the toxin cleavage site (see, for example, Geoghegan et al., *FEBS Letters* 262:119-122 (1990)).

It is understood that donor-acceptor pairs having well-separated emission maxima can be useful in clostridial toxin substrates and, therefore, in the substrate compositions, cells and methods of the invention. Well-separated emission maxima allow altered acceptor emission to be detected without donor emission contamination. A donor fluorophore, or acceptor, or both, can emit, for example, in the far-red, for example, greater than 650 nm. Such far-red emitting donor fluorophores and acceptors include cyanine dyes such as Cy5, Cy5.5 and Cy7 (Selvin, supra, 2000). In one embodiment, a clostridial toxin substrate includes Cy3 and Cy5 as the donor fluorophore-acceptor pair; Cy3 emits maximally at 570 nm, and Cy5 emits maximally at 670 nm. Such cyanine dyes can be prepared by straight forward synthesis, as described, for example, in Gruber et al., *Bioconj. Chem.* 11:161-166 (2000).

A donor fluorophore useful in a clostridial toxin substrate also can be, for example, a lanthanide atom, also known as a rare-earth element. Lanthanides such as terbium (Tb), europium (Eu), dysprosium (Dy) and samarium (Sm) have sharply spiked wavelengths, millisecond lifetimes following an excitation pulse, are unpolarized, and have high quantum yields. A lanthanide donor fluorophore such as a terbium or europium chelate can be combined with a variety of acceptors including organic dye acceptors. A Eu-chelate donor fluorophore can be combined, for example, with allophycocyanin (APC), and a Tb-chelate donor fluorophore can be combined, for example, with tetramethylrhodamine. Background fluorescence due to direct excitation is eliminated temporally; the lifetimes of organic acceptors generally are in the nanosecond range, while the sensitized emission follows the lifetime of the donor fluorophore and is on the order of microseconds to milliseconds (see Selvin, supra, 2000). Thus, determination of resonance energy transfer can be initiated relatively late following excitation, after non-specific interfering fluorescence has faded away. Lanthanide chelates are well known in the art and are commercially available, for example, from EG&G Wallac (Turku, Finland).

A donor fluorophore useful in the invention also can be the well known fluorophore (7-methoxycoumarin-4-yl) acetyl (Mca), which can be combined with an acceptor such as the quencher 2,4-dinitrophenyl (Dnp). See, for example, Kakiuchi et al., *J. Virol. Methods* 80:77-84 (1999). When Mca is combined with the appropriate quencher such as Dnp in a clostridial toxin substrate, increased donor emission fluorescence from Mca ($\lambda_{Em}$ 393 nm) is detected upon cleavage at the clostridial toxin cleavage site and is indicative of toxin activity.

A donor fluorophore useful in the invention also can be, for example, a 2-aminobenzoyl (Abz) group, which can be combined, if desired, with a quencher such as 2,4-dinitrophenyl (Dnp). In an intact clostridial toxin substrate, the Dnp group quenches, by resonance energy transfer, the fluorescence of the Abz group; proteolytic cleavage of the substrate relieves quenching and results in an increase in fluorescence proportional to the concentration of the released Abz fragment. A clostridial toxin substrate containing, for example, Abz at the amino-terminus and a Dnp-derivatized residue such as lysine can be prepared by routine methods as described, for example, in Le Bonniec et al., *Biochemistry* 35:7114-7122 (1996)).

A donor fluorophore or acceptor useful in the invention also can be an Alexa Fluor®-dye, commercially available from Molecular Probes (Eugene, Oreg.). Alexa Fluor®-dyes useful in the substrate compositions, cells and methods of the invention include, for example, Alexa Fluor-350, Alexa Fluor®-430, Alexa Fluor®-488, Alexa Fluor®-532, Alexa Fluor®-546, Alexa Fluor®-568, Alexa Fluor®-594, Alexa Fluor®-633, Alexa Fluor®-647, Alexa Fluor®-660 and Alexa Fluor®-680.

A donor fluorophore or acceptor useful in the invention also can be a genetically encoded dye (see above). It is understood that genetically encoded dyes such as GFP, BFP, CFP or YFP can form FRET pairs with each other, or can be combined with other appropriate donor fluorophores or acceptors. In one embodiment, the clostridial toxin substrate includes a genetically encoded donor fluorophore and a genetically encoded acceptor.

In another embodiment, a clostridial toxin substrate includes a fluorophore with a relatively long fluorescence lifetime of at least a microsecond. Such an acceptor allows time-resolved measurement of the fluorescence emission due to the shorter fluorescence lifetimes of impurities and can enhance the signal to noise ratio. A useful donor fluorophore/acceptor pair for time-resolved fluorescence can be, for example, a europium cryptate donor fluorophore such as Eu-trisbipyridine cryptate (TBP-EU$^{3+}$, $\lambda_{Ex}$ 337 nm) combined with the 105 kDa phycobiliprotein acceptor fluorophore, allophycocyanin (Sittampalam et al., *Curr. Opin. Chem. Biol.* 1:384-391 (1997)). The Eu-trisbipyridine cryptate has two bipyridyl groups that harvest light and channel it to the caged EU$^{3+}$; this donor fluorophore has a long fluorescence lifetime and nonradiatively transfers energy to allophycocyanin when in close proximity to the acceptor, exhibiting greater than 50% transfer efficiency at a donor fluorophore-acceptor distance of 9.5 nm. Both TBP-EU$^{3+}$ and allophycocyanin and their spectroscopic characteristics are very stable in biological media, and allophycocyanin emits ($\lambda_{Em}$=665 nm) with the long lifetime of the donor, allowing time-resolved detection (Kolb et al., *J. Biomol. Screening* 1:203-210 (1996)). Methods of preparing substrates containing such donor fluorophore-acceptor pairs are well known in the art as described, for example, in Kolb et al., supra, 1996, and Sittampalam et al., supra, 1997.

In a further embodiment, the invention relies on a clostridial toxin substrate which contains a non-fluorescent acceptor, sometimes designated a "true quencher." A non-fluorescent acceptor can be useful, for example, in eliminating background fluorescence resulting from direct (nonsensitized) acceptor excitation. A variety of non-fluorescent acceptors are known in the art including, for example, DAB-CYL and QSY-7® dyes (see Molecular Probes, supra, 1996).

A clostridial toxin substrate useful in the invention contains a clostridial toxin cleavage site which is positioned between a donor fluorophore and an acceptor. In one embodiment, the donor fluorophore is positioned amino-terminal of the cleavage site while the acceptor is positioned carboxy-terminal of the cleavage site. In another embodiment, the donor fluorophore is positioned carboxy-terminal of the cleavage site while the acceptor is positioned amino-terminal of the cleavage site.

One skilled in the art understands that there are several considerations in selecting and positioning a donor fluorophore and acceptor in a clostridial toxin substrate useful in the invention. The donor fluorophore and acceptor generally are positioned to minimize interference with substrate binding to, or proteolysis by, the clostridial toxin. Thus, a donor fluorophore and acceptor can be selected and positioned, for example, so as to minimize the disruption of bonded and non-bonded interactions that are important for binding, and to minimize steric hindrance. In addition, the spatial distance between the acceptor and donor fluorophore generally is limited to achieve efficient energy transfer from the donor fluorophore to the acceptor.

In standard nomenclature, the sequence surrounding a clostridial toxin cleavage site is denoted $P_5$-$P_4$-$P_3$-$P_2$-$P_1$-$P_1'$-$P_2'$-$P_3'$-$P_4'$-$P_5'$, with $P_1$-$P_1'$ representing the scissile bond. In particular embodiments, the invention provides a substrate composition, cell or method that includes a clostridial toxin substrate in which the residue at position $P_1$, $P_2$, $P_3$, $P_4$, $P_5$, or $P_{>5}$ is substituted with an amino acid conjugated to a donor fluorophore or acceptor, and in which the residue at position $P_1'$, $P_2'$, $P_3'$, $P_4'$, $P_5'$ or $P_{>5'}$ is substituted with an amino acid conjugated to a donor fluorophore or acceptor. In other embodiments, the invention provides a substrate composition, cell or method that incorporates a clostridial toxin substrate in which the residue at position $P_1$, $P_3$, $P_4$ or $P_{>5}$ is substituted with an amino acid conjugated to a donor fluorophore or acceptor, and in which the residue at position $P_2'$, $P_3'$, $P_5'$ or $P_{>5'}$ is substituted with an amino acid conjugated to a donor fluorophore or acceptor. It is further understood that the amino acid side chain of the residue conjugated to a donor fluorophore or acceptor can be otherwise identical to the residue present in the corresponding position of the naturally occurring target protein, or can contain, for example, a different side chain. Further provided by the invention is a substrate composition, cell or method that incorporates a clostridial toxin substrate in which the residue at $P_3$, $P_4$ or $P_{>5}$ is substituted with an amino acid conjugated to a donor fluorophore or acceptor, and in which the residue at position $P_2'$, $P_3'$, $P_5'$ or $P_{>5'}$ is substituted with an amino acid conjugated to a donor fluorophore or acceptor. Again, the amino acid side chain of the residue conjugated to the donor fluorophore or acceptor can be otherwise identical to the residue present in the corresponding position of the naturally occurring target protein, or can contain, for example, a different side chain.

As discussed above, efficiency of energy transfer from donor fluorophore to acceptor is dependent, in part, on the spatial separation of the donor fluorophore and acceptor molecules. As the distance between the donor fluorophore and acceptor increases, there is less energy transfer to the acceptor, and the donor fluorescence signal therefore increases, even prior to cleavage. The overall increase in fluorescence yield of the donor fluorophore, upon cleavage of the substrate, is dependent upon many factors, including the separation distance between the donor fluorophore and acceptor in the substrate, the spectral overlap between donor fluorophore and acceptor, and the substrate concentration. One skilled in the art understands that, as the concentration of substrate increases, intermolecular quenching of the donor, even after proteolytic cleavage, can become a factor. This phenomenon is denoted the "inner filter effect." One skilled in the art further understands that the intracellular concentration of substrate can be controlled, for example, through use of an inducible promoter or the external concentration of substrate to which a cell is exposed.

The Förster distance, which is the separation between a donor fluorophore and an acceptor for 50% energy transfer, represents a spatial separation between donor fluorophore and acceptor that provides a good sensitivity. For peptide substrates, adjacent residues are separated by a distance of approximately 3.6 A in the most extended conformation. For example, the calculated Förster distance for a fluorescein/tetramethylrhodamine pair is 55A, which would represent a spatial separation between fluorescein and tetramethylrhodamine of about 15 residues in the most extended conformation. Because peptides and peptidomimetics in solution rarely have a fully extended conformation, donor fluorophores and acceptors can be more widely separated than expected based on a calculation performed using 3.6 A per residue and still remain within the Förster distance as shown, for example, by the occurrence of FRET between donor-acceptor pairs separated by about 50 amino acids (Graham et al., *Analyt. Biochem.* 296: 208-217 (2001)).

Förster theory is based on very weak interactions between a donor fluorophore and an acceptor; spectroscopic properties such as absorption of one fluorophore should not be altered in the presence of the other, defining the shortest distance range over which the theory is valid. It is understood that, for many donor fluorophore-acceptor pairs, Förster theory is valid when donor fluorophores and acceptors are separated by about 10 A to 100 A. However, for particular donor fluorophore-acceptor pairs, Förster theory is valid below 10 A as determined by subpicosecond techniques (Kaschke and Ernsting, *Ultrafast Phenomenon in Spectroscopy* (Klose and Wilhelmi (Eds.)) Springer-Verlag, Berlin 1990.

Thus, in particular embodiments, the invention provides a substrate composition, cell or method that incorporates a clostridial toxin substrate in which the donor fluorophore is separated from the acceptor by a distance of at most 100 A. In other embodiments, the invention provides a substrate composition, cell or method that incorporates a clostridial toxin substrate in which the donor fluorophore is separated from the acceptor by a distance of at most 90 A, 80 A, 70 A, 60 A, 50 A, 40 A, 30 A or 20 A. In further embodiments, the invention provides a substrate composition, cell or method that incorporates a clostridial toxin substrate in which the donor fluorophore is separated from the acceptor by a distance of 10 A to 100 A, 10 A to 80 A, 10 A to 60 A, 10 A to 40 A, 10 A to 20 A, 20 A to 100 A, 20 A to 80 A, 20 A to 60 A, 20 A to 40 A, 40 A to 100 A, 40 A to 80 A or 40 A to 60 A. In still further embodiments, the invention provides a substrate composition, cell or method that incorporates a clostridial toxin substrate in which the donor fluorophore and the acceptor are separated by at most six residues, at most eight residues, at most ten residues, at most twelve residues, at most fifteen residues, at most twenty residues, at most twenty-five residues, at most thirty residues, at most thirty-five residues, at most forty residues, at most forty-five residues, at most fifty residues, at most sixty residues, at most seventy residues, at most eighty residues, at most ninety residues, at most 100 residues, at most 150 residues, at most 200 residues or up to the full-length of a naturally occurring clostridial toxin target protein.

One skilled in the art understands that a clostridial toxin substrate useful in the invention can be designed to optimize the efficiency of FRET as well as the ability to detect protease activity. One skilled in the art understands that a donor fluorophore can be selected, if desired, with a high quantum yield, and acceptor can be selected, if desired, with a high extinction coefficient to maximize the Förster distance. One skilled in the art further understands that fluorescence arising from direct excitation of an acceptor can be difficult to distinguish from fluorescence resulting from resonance energy transfer. Thus, it is recognized that a donor fluorophore and acceptor can be selected which have relatively little overlap of their excitation spectra such that the donor can be excited at a wavelength that does not result in direct excitation of the acceptor. It further is recognized that a clostridial toxin substrate useful in the invention can be designed so that the emission spectra of the donor fluorophore and acceptor overlap relatively little such that the two emissions can be readily distinguished. If desired, an acceptor having a high fluorescence quantum yield can be selected; such an acceptor can be used advantageously where acceptor fluorescence emission is to be detected as the sole indicator of clostridial toxin activity, or as part of an emission ratio as discussed above.

It is understood that the donor fluorophore, acceptor, or both, can be located within the active site cavity of botulinum or tetanus toxin holoenzyme. One skilled in the art understands that, if desired, a clostridial toxin substrate useful in the invention can be designed such that, when bound by toxin, the donor fluorophore, acceptor, or both, is excluded from the active site cavity of toxin holoenzyme. As an example, a clostridial toxin substrate can include a botulinum toxin substrate or tetanus toxin substrate in which, when bound by toxin, the donor fluorophore, acceptor, or both, is excluded from the active site cavity of the toxin holoenzyme. The invention provides, for example, a substrate composition, cell or method that incorporates a BoNT/A, BoNT/B, BoNT/C1, BoNT/D, BoNT/E, BoNT/F, BoNT/G or TeNT substrate in which, when bound by toxin, the donor fluorophore, acceptor, or both, is excluded from the active site cavity of toxin holoenzyme. In one embodiment, the BoNT/A substrate contains at least six residues of human SNAP-25, where the six residues include $Gln_{197}$-$Arg_{198}$, and further contains a donor fluorophore, acceptor, or both, which is positioned outside of residues $Arg_{191}$ to $Met_{202}$, which can be within the active site cavity of BoNT/A holoenzyme. In another embodiment, a BoNT/B substrate contains at least six residues of VAMP-2, where the six residues include $Gln_{76}$-$Phe_{77}$, and further contains a donor fluorophore, acceptor, or both, which is positioned outside of residues $Leu_{70}$ to $Ala_{81}$ of VAMP-2, which can be within the active site cavity of BoNT/B holoenzyme.

In a complex of a VAMP substrate and the light chain of BoNT/B (LC/B), nearly all VAMP residues with side chains containing hydrogen bond acceptors or donors were hydrogen bonded with the LC/B. Thus, it is understood that a clostridial toxin substrate useful in the invention can be prepared, if desired, in which the potential for hydrogen bonding, for example, by Ser, Thr, Tyr, Asp, Glu, Asn or Gln residues is not diminished in the clostridial toxin substrate as compared to a native protein sensitive to cleavage by the toxin. In particular embodiments, the present invention provides a substrate composition, cell or method incorporating a clostridial toxin substrate in which the potential for hydrogen-bonding is not diminished in the substrate as compared to a native protein sensitive to cleavage by the corresponding clostridial toxin.

It is understood that, in addition to a donor fluorophore, acceptor and a clostridial toxin recognition sequence, a clostridial toxin substrate useful in the invention optionally can include one or more additional components. As an example, a flexible spacer sequence such as GGGGS (SEQ ID NO: 40) can be included in a clostridial toxin substrate useful in the invention. A useful clostridial toxin substrate further can include, without limitation, one or more of the following: an affinity tag such as HIS6, biotin, or an epitope such as FLAG, hemagluttinin (HA), c-myc, or AU1; an immunoglobulin hinge region; an N-hydroxysuccinimide linker; a peptide or peptidomimetic hairpin turn; or a hydrophilic sequence, or another component or sequence that promotes the solubility or stability of the clostridial toxin substrate.

Methods for modifying proteins, peptides and peptidomimetics to contain a donor fluorophore or acceptor are well known in the art (Fairclough and Cantor, *Methods Enzymol.* 48:347-379 (1978); Glaser et al., *Chemical Modification of Proteins* Elsevier Biochemical Press, Amsterdam (1975); Haugland, *Excited States of Biopolymers* (Steiner Ed.) pp. 29-58, Plenum Press, New York (1983); Means and Feeney, *Bioconjugate Chem.* 1:2-12 (1990); Matthews et al., *Methods Enzymol.* 208:468-496 (1991); Lundblad, *Chemical Reagents for Protein Modification* 2nd Ed., CRC Press, Boca Ratan, Florida (1991); Haugland, supra, 1996). A variety of groups can be used to couple a donor fluorophore or acceptor, for example, to a peptide or peptidomimetic containing a clostridial toxin recognition sequence. A thiol group, for example, can be used to couple a donor fluorophore or acceptor to the desired position in a peptide or peptidomimetic to produce a clostridial toxin substrate useful in the substrate compositions, cells and methods of the invention. Haloacetyl and maleimide labeling reagents also can be used to couple donor fluorophores or acceptors in preparing a clostridial toxin substrate useful in the invention (see, for example, Wu and Brand, supra, 1994).

Donor fluorophores and acceptors including proteins such as GFP and allophycocyanin (APC) can be attached to a clostridial toxin recognition sequence by a variety of means. A donor fluorophore or acceptor can be attached by chemical means, for example, using a cross-linker moiety. Cross-linkers are well known in the art, including homo- and hetero-bifunctional cross-linkers such as BMH and SPDP. One skilled in the art understands that contaminating substrates containing only the donor fluorophore can result in high fluorescence background. Such background can be reduced or prevented, for example, by using a relative excess of acceptor to donor fluorophore in preparation of the clostridial toxin substrate. Where the donor fluorophore or acceptor is a protein, well known chemical methods for specifically linking molecules to the amino- or carboxy-terminus of a protein can be employed. See, for example, "Chemical Approaches to Protein Engineering" in *Protein Engineering: A Practical Approach* Rees et al. (Eds) Oxford University Press, 1992.

It is well known in the art that clostridial toxins have specific and distinct cleavage sites. BoNT/A cleaves a Gln-Arg bond; BoNT/B and TeNT cleave a Gln-Phe bond; BoNT/C1 cleaves a Lys-Ala or Arg-Ala bond; BoNT/D cleaves a Lys-Leu bond; BoNT/E cleaves an Arg-Ile bond; BoNT/F cleaves a Gln-Lys bond; and BoNT/G cleaves an Ala-Ala bond (see Table D). In standard nomenclature, the sequence surrounding a clostridial toxin cleavage site is denoted $P_5$-$P_4$-$P_3$-$P_2$-$P_1$-$P_1'$-$P_2'$-$P_3'$-$P_4'$-$P_5'$, with $P_1$-$P_1'$ representing the scissile bond. It is understood that a $P_1$ or $P_1'$ site, or both, can be substituted with another amino acid or amino acid mimetic in place of the naturally occurring residue. As an example, BoNT/A substrates have been prepared in which the $P_1$ position (Gln) is modified to be an alanine, 2-aminobutyric acid or asparagine residue; these substrates were hydrolyzed by BoNT/A at the $P_1$-Arg bond (Schmidt and Bostian, *J. Protein Chem.* 16:19-26 (1997)). While it is recognized that substitutions can be introduced at the $P_1$ position of the scissile bond, for example, a BoNT/A scissile bond, it is further recognized that conservation of the $P_1'$ residue can be advantageous (Vaidyanathan et al., *J. Neurochem.* 72:327-337 (1999)). Thus, in particular embodiments, the invention provides a substrate composition, cell or method which relies on a clostridial toxin substrate having a clostridial toxin recognition sequence in which the $P_1'$ residue is not modified or substituted relative to the naturally occurring residue in a target protein cleaved by the clostridial toxin. In other embodiments, the invention provides a substrate composition, cell or method which relies on a clostridial toxin substrate having a recognition sequence in which the $P_1$ residue is modified or substituted relative to the naturally occurring residue in a target protein cleaved by the clostridial toxin; such a clostridial toxin substrate retains susceptibility to peptide bond cleavage between the $P_1$ and $P_1'$ residues.

TABLE D

Bond cleaved in human VAMP-2, SNAP-25 or Syntaxin

| Toxin | Target | $P_4$-$P_3$-$P_2$-$P_1$ --- $P_1'$-$P_2'$-$P_3'$-$P_4'$ | SEQ ID NO |
|---|---|---|---|
| BoNT/A | SNAP-25 | Glu-Ala-Asn-Gln—Arg*-Ala-Thr-Lys | SEQ ID NO: 41 |
| BoNT/B | VAMP-2 | Gly-Ala-Ser-Gln—Phe*-Glu-Thr-Ser | SEQ ID NO: 42 |
| BoNT/C1 | syntaxin | Asp-Thr-Lys-Lys—Ala*-Val-Lys-Tyr | SEQ ID NO: 43 |
| BoNT/D | VAMP-2 | Arg-Asp-Gln-Lys—Leu*-Ser-Glu-Leu | SEQ ID NO: 44 |
| BoNT/E | SNAP-25 | Gln-Ile-Asp-Arg—Ile*-Met-Glu-Lys | SEQ ID NO: 45 |
| BoNT/F | VAMP-2 | Glu-Arg-Asp-Gln—Lys*-Leu-Ser-Glu | SEQ ID NO: 46 |
| BoNT/G | VAMP-2 | Glu-Thr-Ser-Ala—Ala*-Lys-Leu-Lys | SEQ ID NO: 47 |
| TeNT | VAMP-2 | Gly-Ala-Ser-Gln—Phe*-Glu-Thr-Ser | SEQ ID NO: 48 |

*Scissile bond shown in bold

Figure 4A:
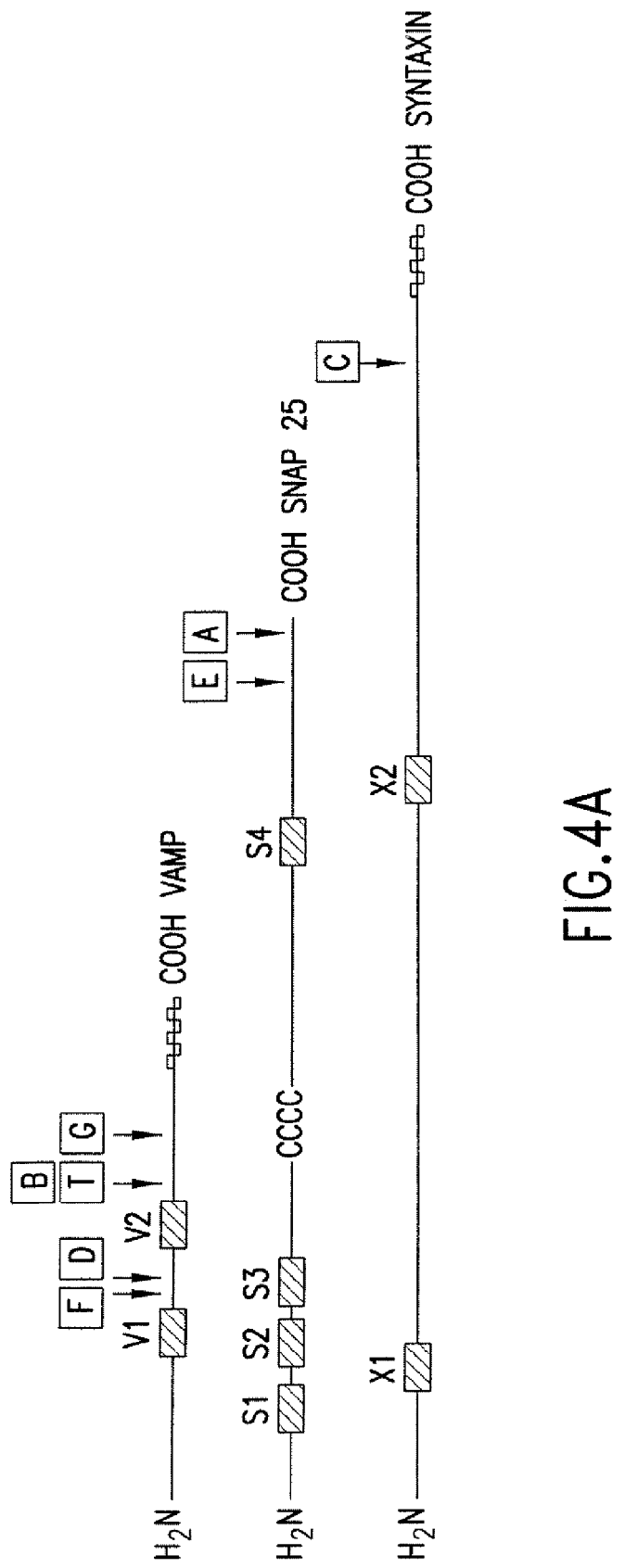
FIG. 4 shows the neurotoxin recognition motif of VAMP, SNAP-25 and syntaxin. (A) Hatched boxes indicate the presence and positions of a motif common to the three targets of clostridial neurotoxins. (B) The recognition motif is composed of hydrophobic residues ("h"); negatively charged Asp or Glu residues ("-") and polar residues ("p"); "x" represents any amino acid. The motif is included in regions of VAMP, SNAP-25 and syntaxin predicted to adopt an α-helical conformation. (C) A top view of the motif in an α-helical conformation is shown. Negatively charged residues align on one face, while hydrophobic residues align on a second face.
Figures 4B, 4C:
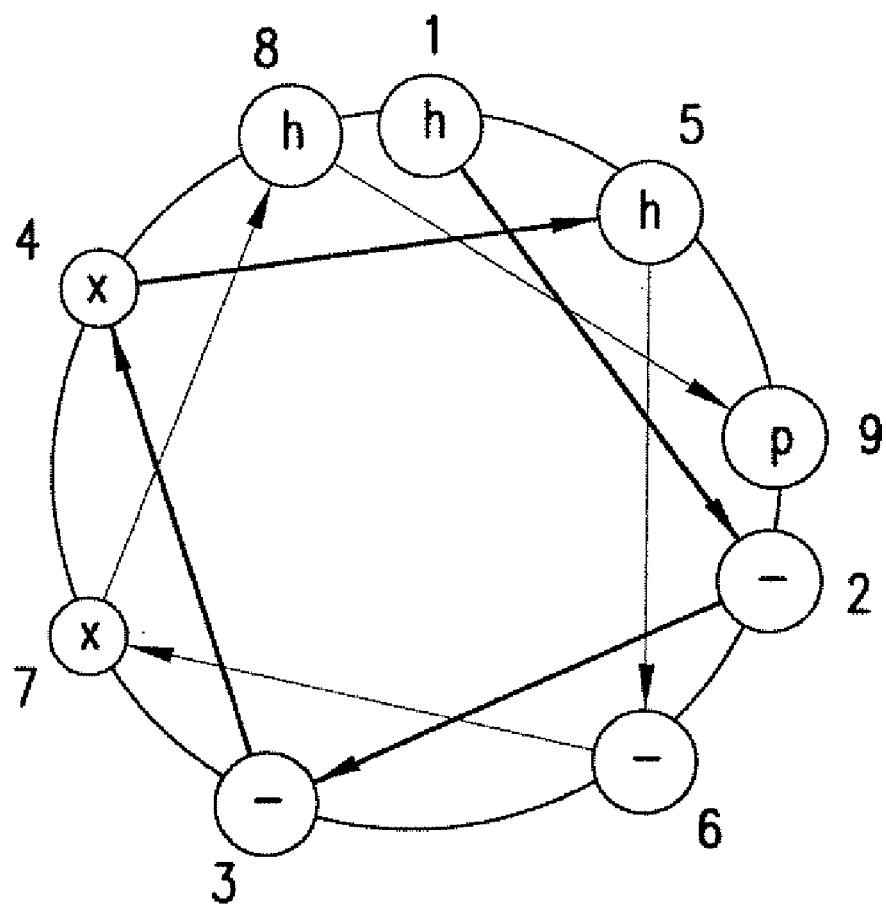

SNAP-25, VAMP and syntaxin share a short motif located within regions predicted to adopt an α-helical conformation (see FIG. 4). This motif is present in SNAP-25, VAMP and syntaxin isoforms expressed in animals sensitive to the neurotoxins. In contrast, *Drosophila* and yeast homologs that are resistant to these neurotoxins and syntaxin isoforms not involved in exocytosis contain sequence variations in the α-helical motif regions of these VAMP and syntaxin proteins.

Multiple repetitions of the α-helical motif are present in proteins sensitive to cleavage by clostridial toxins: Four copies are naturally present in SNAP-25; two copies are naturally present in VAMP; and two copies are naturally present in syntaxin (see FIG. 4A). Furthermore, peptides corresponding to the specific sequence of the α-helical motifs can inhibit neurotoxin activity in vitro and in vivo, and such peptides can cross-inhibit different neurotoxins. In addition, antibodies raised against such peptides can cross-react among the three target proteins, indicating that this α-helical motif is exposed on the cell surface and adopts a similar configuration in each of the three target proteins. Consistent with these findings, SNAP-25-specific, VAMP-specific and syntaxin-specific neurotoxins cross-inhibit each other by competing for the same binding site, although they do not cleave targets non-specifically. These results indicate that a clostridial toxin recognition sequence can include, if desired, at least one α-helical motif. It is recognized that an α-helical motif is not required for cleavage by a clostridial toxin, as evidenced by 16-mer and 17-mer substrates for BoNT/A, discussed further below.

Although multiple α-helical motifs are found in the naturally occurring SNAP-25, VAMP and syntaxin target proteins, a clostridial toxin recognition sequence useful in the substrate compositions, cells and methods of the invention can have a single α-helical motif. In particular embodiments, the invention relies on a clostridial toxin recognition sequence including two or more α-helical motifs. A BoNT/A or BoNT/E recognition sequence can include, for example, the S4 α-helical motif, alone or combined with one or more additional α-helical motifs; a BoNT/B, BoNT/G or TeNT recognition sequence can include, for example, the V2 α-helical motif, alone or combined with one or more additional α-helical motifs; a BoNT/C1 recognition sequence can include, for example, the S4 α-helical motif, alone or combined with one or more additional α-helical motifs, or X2 α-helical motif, alone or combined with one or more additional α-helical motifs; and a BoNT/D or BoNT/F recognition sequence can include, for example, the V1 α-helical motif, alone or combined with one or more additional α-helical motifs (see FIG. 4A).

A variety of BoNT/A substrates are useful in the invention. A BoNT/A substrate useful in the substrate compositions, cells and methods of the invention can include, for example, at least six consecutive residues of SNAP-25, where the six consecutive residues include Gln-Arg, or a peptidomimetic thereof. Such a BoNT/A substrate can have, for example, at least six consecutive residues of human SNAP-25, where the six consecutive residues include $Gln_{197}$-$Arg_{198}$, or a peptidomimetic thereof. Such a BoNT/A substrate can include, for example, the amino acid sequence Glu-Ala-Asn-Gln-Arg-Ala-Thr-Lys (SEQ ID NO: 41) or, for example, residues 187 to 203 of human SNAP-25 (SEQ ID NO: 4). A BoNT/A substrate further can include, if desired, a carboxy-terminal amide.

As used herein, the term "botulinum toxin serotype A recognition sequence" is synonymous with "BoNT/A recognition sequence" and means a scissile bond together with adjacent or non-adjacent recognition elements sufficient for detectable proteolysis at the scissile bond by a BoNT/A under conditions suitable for clostridial toxin protease activity. A scissile bond cleaved by BoNT/A can be, for example, Gln-Ala.

A variety of BoNT/A recognition sequences are well known in the art and are useful in the invention. A BoNT/A recognition sequence can have, for example, residues 134 to 206 or residues 137 to 206 of human SNAP-25 (Ekong et al., supra, 1997; U.S. Pat. No. 5,962,637). A BoNT/A recognition sequence also can include, without limitation, the sequence Thr-Arg-Ile-Asp-Glu-Ala-Asn-Gln-Arg-Ala-Thr-Lys-Met (SEQ ID NO: 49) or a peptidomimetic thereof, which corresponds to residues 190 to 202 of human SNAP-25; Ser-Asn-Lys-Thr-Arg-Ile-Asp-Glu-Ala-Asn-Gln-Arg-Ala-Thr-Lys (SEQ ID NO: 50) or a peptidomimetic thereof, which corresponds to residues 187 to 201 of human SNAP-25; Ser-Asn-Lys-Thr-Arg-Ile-Asp-Glu-Ala-Asn-Gln-Arg-Ala-Thr-Lys-Met (SEQ ID NO: 51) or a peptidomimetic thereof, which corresponds to residues 187 to 202 of human SNAP-25; Ser-Asn-Lys-Thr-Arg-Ile-Asp-Glu-Ala-Asn-Gln-Arg-Ala-Thr-Lys-Met-Leu (SEQ ID NO: 52) or a peptidomimetic thereof, which corresponds to residues 187 to 203 of human SNAP-25; Asp-Ser-Asn-Lys-Thr-Arg-Ile-Asp-Glu-Ala-Asn-Gln-Arg-Ala-Thr-Lys-Met (SEQ ID NO: 53) or a peptidomimetic thereof, which corresponds to residues 186 to 202 of human SNAP-25; or Asp-Ser-Asn-Lys-Thr-Arg-Ile-Asp-Glu-Ala-Asn-Gln-Arg-Ala-Thr-Lys-Met-Leu (SEQ ID NO: 54) or a peptidomimetic thereof, which corresponds to residues 186 to 203 of human SNAP-25. See, for example, Schmidt and Bostian, *J. Protein Chem.* 14:703-708 (1995); Schmidt and Bostian, supra, 1997; Schmidt et al., *FEBS Letters* 435:61-64 (1998); and Schmidt and Bostian, U.S. Pat. No. 5,965,699). If desired, a similar BoNT/A recognition sequence can be prepared from a corresponding (homologous) segment of another BoNT/A-sensitive SNAP-25 isoform or homolog such as, for example, murine, rat, goldfish or zebrafish SNAP-25 or can be any of the peptides described herein or known in the art, for example, in U.S. Pat. No. 5,965,699.

sponding clostridial toxin. As an example, as compared to a 17-mer corresponding to residues 187 to 203 of human SNAP-25, substitution of Asp193 with Asn in the BoNT/A

TABLE E

Cleavage of SNAP-25 and related proteins[a,b,c,d]

| Species | Isoform | Cleavage Sites | SEQ ID NO: | Resistance to Cleavage by |
|---|---|---|---|---|
| | | BoNT/E ⇓        BoNT/A BoNT/C ⇓⇓ | | |
| human mouse rat | SNAP-25 | [174] qnrqid ri mekadsnktridean qra tkmlgsg [206] | | none[a] |
| human | SNAP-23 | [180] qnpqik ri tdkadtnrdridian ara kklids *end* | | all[b] |
| mouse | SNAP-23 | [179] qnqqiq ki tekadtnknridian tra kklids *end* | | BoNT/A & C |
| chicken | SNAP-25 | [174] qnrqid ri meklipikpglmkpt svq qrcsavvk *end* | | BoNT/A & C |
| goldfish | SNAP-25A | [171] qnrqid ri mdmadsnktridean qra tkmlgsg *end* | | none |
| goldfish | SNAP-25B | [172] qnrqid ri mekadsnktridean qra tkmlgsg *end* | | none |
| Torpedo | SNAP-25 | [180] qnaqvd ri vvkgdmnkaridean kha tkml *end* | | BoNT/E[c] & A |
| sea urchin | SNAP-25 | [180] qnsqvg ri tskaesnegrinsad kra knilrnk *end* | | (?)[e] |
| C-elegans | SNAP-25 | [203] qnrqld ri hdkqsnevrvesank rak nlitk *end* | | BoNT/A & C |
| Drosophila | SNAP-25 | [182] qnrqid ri nrkgesneariavan qra hqllk *end* | | BoNT/E & A[e] |
| leech | SNAP-25 | [181] qnrqvd ri nnkmtsnqlrisdan kra skllke *end* | | BoNT/A[e] |

[a] = In vitro cleavage of SNAP-25 requires 1000-fold higher BoNT/C concentration than BoNT/A or /E.
[b] = Substitution of p182r, or k185dd (boxes) induces susceptibility toward BoNT/E.
[c] = Resistance to BoNT/A possibly due to d189 or e189 substitution by v189, see box.
[d] = Note that Torpedo is susceptible to BoNT/A.
[e] = Note the presence of several non-conservative mutations around putative cleavage sites.

Figure 5:
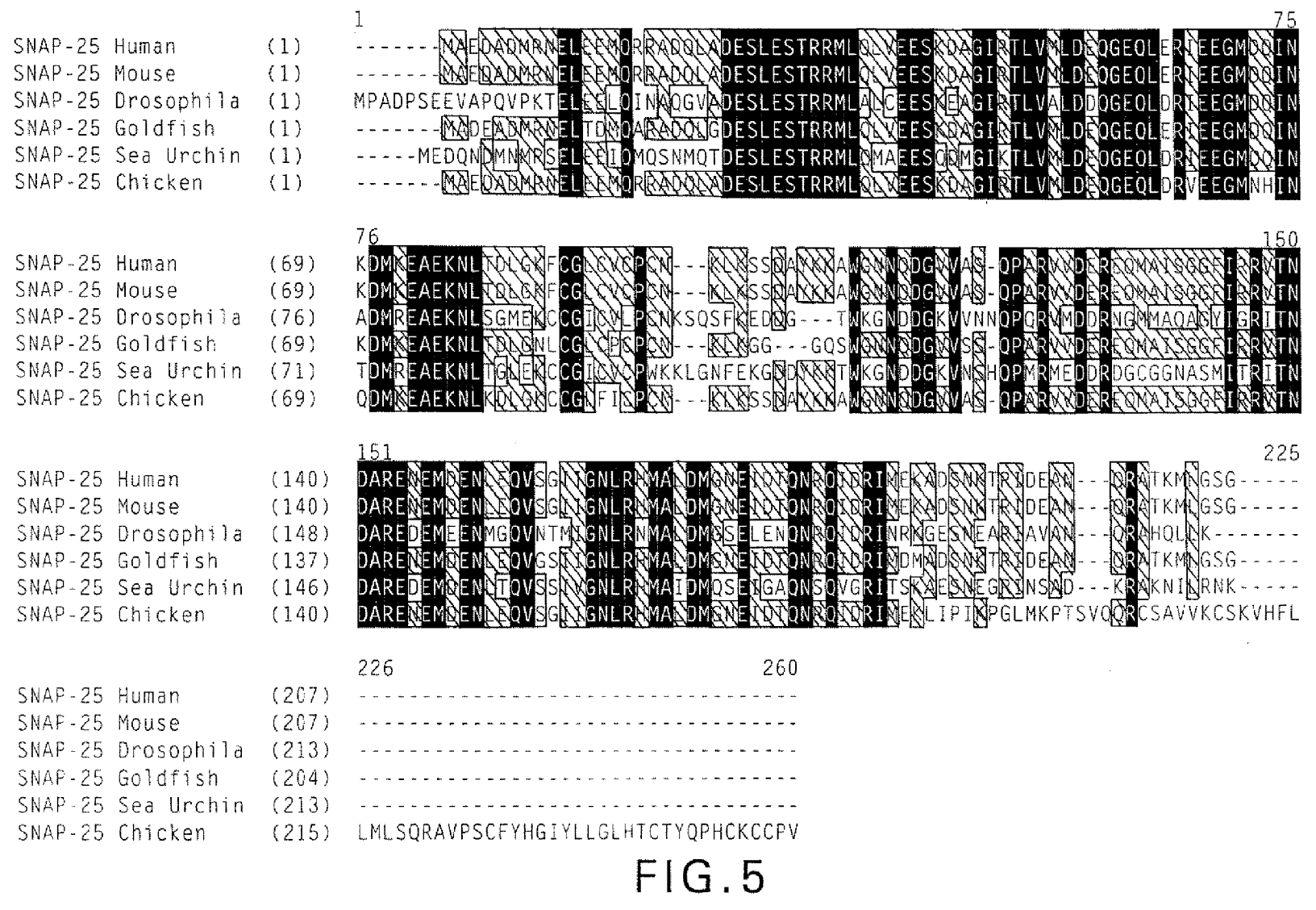

A BoNT/A recognition sequence useful in the invention can correspond to a segment of a protein that is sensitive to cleavage by botulinum toxin serotype A, or can be substantially similar to a segment of a BoNT/A-sensitive protein. As illustrated in Table E, a variety of naturally occurring proteins sensitive to cleavage by BoNT/A are known in the art and include, for example, human, mouse and rat SNAP-25; and goldfish SNAP-25A and SNAP-25B. Thus, a BoNT/A recognition sequence useful in the invention can correspond, for example, to a segment of human SNAP-25, mouse SNAP-25, rat SNAP-25, goldfish SNAP-25A or 25B, or another naturally occurring protein sensitive to cleavage by BoNT/A. Furthermore, comparison of native SNAP-25 amino acid sequences cleaved by BoNT/A reveals that such sequences are not absolutely conserved (see Table E and FIG. 5), indicating that a variety of amino acid substitutions and modifications relative to a naturally occurring BoNT/A-sensitive SNAP-25 sequence can be tolerated in a BoNT/A recognition sequence useful in the invention.

A clostridial toxin substrate, such as a BoNT/A substrate, can have one or multiple modifications as compared to a naturally occurring sequence that is cleaved by the corresponding clostridial toxin. As an example, as compared to a 17-mer corresponding to residues 187 to 203 of human SNAP-25, substitution of Asp193 with Asn in the BoNT/A substrate resulted in a relative rate of proteolysis of 0.23; substitution of Glu 194 with Gln resulted in a relative rate of 2.08; substitution of Ala195 with 2-aminobutyric acid resulted in a relative rate of 0.38; and substitution of Gln197 with Asn, 2-aminobutyric acid or Ala resulted in a relative rate of 0.66, 0.25, or 0.19, respectively (see Table F). Furthermore, substitution of Ala199 with 2-aminobutyric acid resulted in a relative rate of 0.79; substitution of Thr200 with Ser or 2-aminobutyric acid resulted in a relative rate of 0.26 or 1.20, respectively; substitution of Lys201 with Ala resulted in a relative rate of 0.12; and substitution of Met202 with Ala or norleucine resulted in a relative rate of 0.38 or 1.20, respectively. See Schmidt and Bostian, supra, 1997. These results indicate that a variety of residues can be substituted in a clostridial toxin substrate as compared to a naturally occurring toxin-sensitive sequence. In the case of BoNT/A, these results indicate that residues including but not limited to Glu194, Ala195, Gln197, Ala199, Thr200 and Met202, Leu203, Gly204, Ser205, and Gly206, as well as residues more distal from the Gln-Arg scissile bond, can be substituted or conjugated to a donor fluorophore or acceptor in a BoNT/A substrate useful in the invention. Such a BoNT/A substrate is detectably proteolyzed at the scissile bond by BoNT/A under conditions suitable for clostridial toxin protease activity. Thus, a BoNT/A substrate can include, if desired, one or several amino acid substitutions, additions or deletions relative to a naturally occurring SNAP-25 sequence.

TABLE F

Kinetic parameters of BoNT/A synthetic peptide substrates

| Peptide | Sequence[a] | SEQ ID NO: | Relative Rate[b] |
|---|---|---|---|
| [1-15] | SNKTRIDEANQRATK | 28 | 0.03 |
| [1-16] | SNKTRIDEANQRATKM | 29 | 1.17 |
| [1-17] | SNKTRIDEANQRATKML | 30 | 1.00 |
| M16A | SNKTRIDEANQRATKAL | 44 | 0.38 |
| M16X | SNKTRIDEANQRATKXL | 45 | 1.20 |
| K15A | SNKTRIDEANQRATAML | 46 | 0.12 |
| T14S | SNKTRIDEANQRASKML | 47 | 0.26 |
| T14B | SNKTRIDEANQRABKML | 48 | 1.20 |
| A13B | SNKTRIDEANQRBTKML | 49 | 0.79 |
| Q11A | SNKTRIDEANARATKML | 50 | 0.19 |
| Q11B | SNKTRIDEANBRATKML | 51 | 0.25 |
| Q11N | SNKTRIDEANNRATKML | 52 | 0.66 |
| N10A | SNKTRIDEAAQRATKML | 53 | 0.06 |
| A9B | SNKTRIDEBNQRATKML | 54 | 0.38 |
| E8Q | SNKTRIDQANQRATKML | 55 | 2.08 |
| D7N | SNKTRINEANQRATKML | 56 | 0.23 |

[a]Nonstandard amino acid abbreviations are: B, 2-aminobutyric acid; X, 2-aminohexanoic acid (norleucine)
[b]Initial hydrolysis rates relative to peptide [1-17]. Peptide concentrations were 1.0 mM.

A variety of BoNT/B substrates are useful in the invention. A BoNT/B substrate useful in the invention can have, for example, at least six consecutive residues of VAMP, where the six consecutive residues include Gln-Phe, or a peptidomimetic thereof. As an example, a BoNT/B substrate can contain at least six consecutive residues of human VAMP-2, the six consecutive residues including $Gln_{76}$-$Phe_{77}$, or a peptidomimetic thereof. In one embodiment, a BoNT/B substrate includes the amino acid sequence Gly-Ala-Ser-Gln-Phe-Glu-Thr-Ser (SEQ ID NO: 42), or a peptidomimetic thereof. In other embodiments, a BoNT/B substrate includes residues 55 to 94 of human VAMP-2 (SEQ ID NO: 11); residues 60 to 94 of human VAMP-2 (SEQ ID NO: 11); or residues 60 to 88 of human VAMP-2 (SEQ ID NO: 11), or a peptidomimetic of one of these sequences.

As used herein, the term "botulinum toxin serotype B recognition sequence" is synonymous with "BoNT/B recognition sequence" and means a scissile bond together with adjacent or non-adjacent recognition elements sufficient for detectable proteolysis at the scissile bond by a BoNT/B under appropriate conditions. A scissile bond cleaved by BoNT/B can be, for example, Gln-Phe.

A variety of BoNT/B recognition sequences are well known in the art or can be defined by routine methods. Such a BoNT/B recognition sequence can include, for example, a sequence corresponding to some or all of the hydrophilic core of a VAMP protein such as human VAMP-1 or human VAMP-2. A BoNT/B recognition sequence can include, without limitation, residues 33 to 94, residues 45 to 94, residues 55 to 94, residues 60 to 94, residues 65 to 94, residues 60 to 88 or residues 65 to 88 of human VAMP-2 (SEQ ID NO: 11), or residues 60 to 94 of human VAMP-1 (SEQ ID NO: 10). See, for example, Shone et al., *Eur. J. Biochem.* 217: 965-971 (1993). and U.S. Pat. No. 5,962,637. If desired, a similar BoNT/B recognition sequence can be prepared from a corresponding (homologous) segment of another BoNT/B-sensitive VAMP isoform or homolog such as human VAMP-1 or rat or chicken VAMP-2.

Thus, it is understood that a BoNT/B recognition sequence can correspond to a segment of a protein that is sensitive to cleavage by botulinum toxin serotype B, or can be substantially similar to such a segment of a BoNT/B-sensitive protein. As shown in Table G, a variety of naturally occurring proteins sensitive to cleavage by BoNT/B are known in the art and include, for example, human, mouse and bovine VAMP-1 and VAMP-2; rat VAMP-2; rat cellubrevin; chicken VAMP-2; Torpedo VAMP-1; sea urchin VAMP; Aplysia VAMP; squid VAMP; *C. elegans* VAMP; *Drosophila* n-syb; and leech VAMP. Thus, a BoNT/B recognition sequence included in a BoNT/B substrate can correspond, for example, to a segment of human VAMP-1 or VAMP-2, mouse VAMP-1 or VAMP-2, bovine VAMP-1 or VAMP-2, rat VAMP-2, rat cellubrevin, chicken VAMP-2, Torpedo VAMP-1, sea urchin VAMP, Aplysia VAMP, squid VAMP, *C. elegans* VAMP, *Drosophila* n-syb, leech VAMP, or another naturally occurring protein sensitive to cleavage by BoNT/B. Furthermore, as shown in Table G, comparison of native VAMP amino acid sequences cleaved by BoNT/B reveals that such sequences are not absolutely conserved (see, also, FIG. 6), indicating that a variety of amino acid substitutions and modifications relative to a naturally occurring VAMP sequence can be tolerated in a BoNT/B substrate useful, for example, in a BoNT/B substrate composition of the invention.

TABLE G

Cleavage of VAMP[a,b]

| Species | Isoform | Cleavage Sites | | | | SEQ ID NO: | Resistance Cleavage by |
|---|---|---|---|---|---|---|---|
| | | BoNT/F | BoNT/D | BoNT/B TeNT | BoNT/G | | |
| | | ⇓⇓ | | ⇓ | ⇓ | | |
| human mouse bovine | VAMP-1 | 53 dkvlerd qkl selddradalqagas qf ess aa klkrkyww | | 92 | | | none |
| human mouse bovine | VAMP-2 | 51 dkvlerd qkl selddradalqagas qf ets aa klkrkyww | | 90 | | | none |
| rat | VAMP-2 | 53 dkvlerd qkl selddradalqagas vf ess aa klkrkyww | | 92 | | | TeNT & BoNT/B |
| rat | VAMP-2 | 51 dkvlerd qkl selddradalqagas qf ets aa klkrkyww | | 90 | | | none |

TABLE G-continued

Cleavage of VAMP[a,b]

| Species | Isoform | Cleavage Sites | SEQ ID NO: | Resistance Cleavage by |
|---|---|---|---|---|
| rat | Cellubrevin | [38] dkvlerd qkl selddradalqagas qf ets aa klkrkyww [77] | | none |
| rat | TI-VAMP | [146] dlvaqrg qkl ellidktenlvdssv tf ktt sr nlaramcm [175] | | all |
| chicken | VAMP-1 | ----erd qkl selddradalqagas vf ess aa klkr----- | | TeNT & BoNT/B |
| chicken | VAMP-2 | ----erd qkl selddradalqagas qf ets aa klkr----- | | none |
| Torpedo | VAMP-1 | [55] dkvlerd qkl selddradalqagas qf ess aa klkrkyww [94] | | none |
| sea urchin | VAMP | [35] dkvldrd qal svlddradalqqgas qf etn ag klkrkyww [74] | | BoNT/F, D & G |
| Aplysia | VAMP | [41] ekvldrd qki sqlddraealqagas qf eas ag klkrkyww [80] | | BoNT/G |
| squid | VAMP | [60] dkvlerd ski selddradalqagas qf eas ag klkrkfww [99] | | BoNT/F & G |
| C. elegans | VAMP | [86] nkvmerd vql nsldhraevlqngas qf qqs sr elkrqyww [115] | | BoNT/F, D & G |
| Drosphila | syb[a] | [67] ekvlerd qkl selgeradqleqgas qs eqq ag klkrkqww [106] | TeNT & BoNT/B & G | |
| Drosphila | n-syb[b] | [61] ekvlerd skl selddradalqqgas qf eqq ag klkrkfwl [100] | | BoNT/F & G |
| leech | VAMP | [49] dkvlekd qkl aeldgradalqagas qf eas ag klkrkfww [88] | | BoNT/G |

[a] = Sequence corrected in position 93 (f > s).
[b] = Sequence corrected in position 68 (t > s).

Various BoNT/C1 substrates are useful in the invention. A BoNT/C1 substrate useful in the invention can have, for example, at least six consecutive residues of syntaxin, the six consecutive residues including Lys-Ala, or a peptidomimetic thereof. As an example, a BoNT/C1 substrate can have at least six consecutive residues of human syntaxin, the six consecutive residues including $Lys_{253}$-$Ala_{254}$, or a peptidomimetic thereof. In one embodiment, a BoNT/C1 substrate contains the amino acid sequence Asp-Thr-Lys-Lys-Ala-Val-Lys-Tyr (SEQ ID NO: 43), or a peptidomimetic thereof.

A BoNT/C1 substrate also can contain, for example, at least six consecutive residues of SNAP-25, where the six consecutive residues include Arg-Ala, or a peptidomimetic thereof. Such a BoNT/C1 substrate can have, for example, at least six consecutive residues of human SNAP-25, the six consecutive residues including $Arg_{198}$-$Ala_{199}$, or a peptidomimetic thereof. In one embodiment, a BoNT/C1 substrate contains residues 93 to 202 of human SNAP-25 (SEQ ID NO: 4), or a peptidomimetic thereof.

As used herein, the term "botulinum toxin serotype C1 recognition sequence" is synonymous with "BoNT/C1 recognition sequence" and means a scissile bond together with adjacent or non-adjacent recognition elements sufficient for detectable proteolysis at the scissile bond by a BoNT/C1 under appropriate conditions. A scissile bond cleaved by BoNT/C1 can be, for example, Lys-Ala or Arg-Ala.

Figure 7:
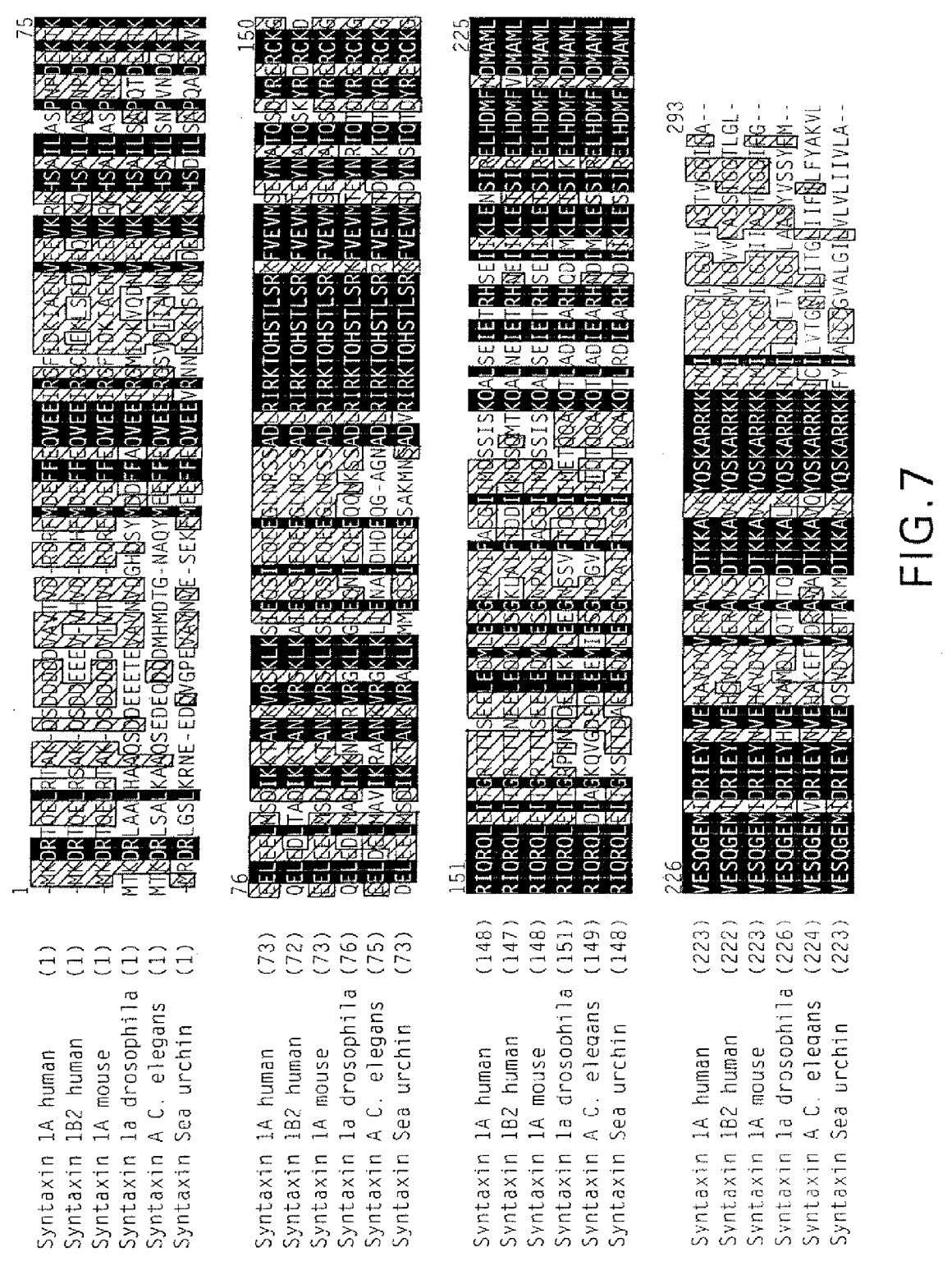

It is understood that a BoNT/C1 recognition sequence can correspond to a segment of a protein that is sensitive to cleavage by botulinum toxin serotype C1, or can be substantially similar to a segment of a BoNT/C1-sensitive protein. As shown in Table H, a variety of naturally occurring proteins sensitive to cleavage by BoNT/C1 are known in the art and include, for example, human, rat, mouse and bovine syntaxin 1A and 1B; rat syntaxins 2 and 3; sea urchin syntaxin; Aplysia syntaxin 1; squid syntaxin; Drosophila Dsynt1; and leech syntaxin 1. Thus, a BoNT/C1 recognition sequence useful in a BoNT/C1 substrate can correspond, for example, to a segment of human, rat, mouse or bovine syntaxin 1A or 1B, rat syntaxin 2, rat syntaxin 3, sea urchin syntaxin, Aplysia syntaxin 1, squid syntaxin, Drosophila Dsynt1, leech syntaxin 1, or another naturally occurring protein sensitive to cleavage by BoNT/C1. Furthermore, comparison of native syntaxin amino acid sequences cleaved by BoNT/C1 reveals that such sequences are not absolutely conserved (see Table H and FIG. 7), indicating that a variety of amino acid substitutions and modifications relative to a naturally occurring BoNT/C1-sensitive syntaxin sequence can be tolerated in a BoNT/C1 substrate useful in the invention.

A variety of naturally occurring SNAP-25 proteins also are sensitive to cleavage by BoNT/C1, including human, mouse and rat SNAP-25; goldfish SNAP-25A and 25B; and Drosophila and leech SNAP-25. Thus, a BoNT/C1 recognition sequence useful in a BoNT/C1 substrate can correspond, for example, to a segment of human, mouse or rat SNAP-25, goldfish SNAP-25A or 25B, Torpedo SNAP-25, zebrafish SNAP-25, *Drosophila* SNAP-25, leech SNAP-25, or another naturally occurring protein sensitive to cleavage by BoNT/C1. As discussed above in regard to variants of naturally occurring syntaxin sequences, comparison of native SNAP-25 amino acid sequences cleaved by BoNT/C1 reveals sig- The term "botulinum toxin serotype D recognition sequence" is synonymous with "BoNT/D recognition sequence" and means a scissile bond together with adjacent or non-adjacent recognition elements sufficient for detectable proteolysis at the scissile bond by a BoNT/D under appropriate conditions. A scissile bond cleaved by BoNT/D can be, for example, Lys-Leu.

TABLE H

Cleavage of syntaxin

| Species | Isoform | Cleavage Sites | SEQ ID NO: | Resistance to Cleavage by |
|---|---|---|---|---|
| | | BoNT/C ⇓ | | |
| human rat mouse bovine | syntaxin 1A | 245          262<br>eravsdtk ka vkyqskar | | no |
| human rat mouse bovine | syntaxin 1B | 244          261<br>eravsdtk ka vkyqskar | | no |
| rat | syntaxin 2 | 245          262<br>ehakeetk ka ikyqskar | | no |
| rat | syntaxin 3 | 244          261<br>ekardetr ka mkyqgqar | | no |
| rat | syntaxin 4 | 244          261<br>ergqehvk ia lenqkkar | | yes |
| chicken | syntaxin 1B | 239          259<br>vpevfvtk sa vmyqcksr | | expected |
| sea urchin | syntaxin | 243          260<br>vrrqndtk ka vkyqskar | | no |
| *Aplysia* | syntaxin 1 | 247          264<br>etakmdtk ka vkyqskar | | no |
| squid | syntaxin | 248          265<br>etakvdtk ka vkyqskar | | no |
| *Drosophila* | Dsynt 1 | 248          265<br>qtatqdtk ka lkyqskar265 | | no |
| leech | syntaxin 1 | 251          268<br>etaaadtk ka mkyqsaar | | no | nificant sequence variability (see Table E and FIG. 5 above), indicating that a variety of amino acid substitutions and modifications relative to a naturally occurring BoNT/C1-sensitive SNAP-25 sequence can be tolerated in a BoNT/C1 substrate useful in the invention.

One skilled in the art appreciates that a variety of BoNT/D substrates are useful in the invention. A BoNT/D substrate useful in the invention can have, for example, at least six consecutive residues of VAMP, the six consecutive residues including Lys-Leu, or a peptidomimetic thereof. In one embodiment, a BoNT/D substrate contains at least six consecutive residues of human VAMP, the six consecutive residues including $Lys_{59}$-$Leu_{60}$, or a peptidomimetic thereof. In another embodiment, a BoNT/D substrate contains the amino acid sequence Arg-Asp-Gln-Lys-Leu-Ser-Glu-Leu (SEQ ID NO: 44), or a peptidomimetic thereof. In a further embodiment, a BoNT/D substrate includes residues 27 to 116 of rat VAMP-2 (SEQ ID NO: 109), or a peptidomimetic thereof.

A variety of BoNT/D recognition sequences are well known in the art or can be defined by routine methods. A BoNT/D recognition sequence can include, for example, residues 27 to 116; residues 37 to 116; residues 1 to 86; residues 1 to 76; or residues 1 to 69 of rat VAMP-2 (SEQ ID NO: 109; Yamasaki et al., *J. Biol. Chem.* 269:12764-12772 (1994)). Thus, a BoNT/D recognition sequence can include, for example, residues 27 to 69 or residues 37 to 69 of rat VAMP-2 (SEQ ID NO: 109). If desired, a similar BoNT/D recognition sequence can be prepared from a corresponding (homologous) segment of another BoNT/D-sensitive VAMP isoform or homolog such as human VAMP-1 or human VAMP-2.

A BoNT/D recognition sequence can correspond to a segment of a protein that is sensitive to cleavage by botulinum toxin serotype D, or can be substantially similar to a segment of a BoNT/D-sensitive protein. As shown in Table H, a variety of naturally occurring proteins sensitive to cleavage by BoNT/D are known in the art and include, for example, human, mouse and bovine VAMP-1 and VAMP-2; rat VAMP-1 and VAMP-2; rat cellubrevin; chicken VAMP-1 and VAMP-2; Torpedo VAMP-1; Aplysia VAMP; squid VAMP; *Drosophila* syb and n-syb; and leech VAMP. Thus, a BoNT/D recognition sequence can correspond, for example, to a segment of human VAMP-1 or VAMP-2, mouse VAMP-1 or VAMP-2, bovine VAMP-1 or VAMP-2, rat VAMP-1 or VAMP-2, rat cellubrevin, chicken VAMP-1 or VAMP-2, Torpedo VAMP-1, Aplysia VAMP, squid VAMP, *Drosophila* syb or n-syb, leech VAMP, or another naturally occurring protein sensitive to cleavage by BoNT/D. Furthermore, as shown in Table H above, comparison of native VAMP amino acid sequences cleaved by BoNT/D reveals significant sequence variability (see, also, FIG. 6), indicating that a variety of amino acid substitutions and modifications relative to a naturally occurring BoNT/D-sensitive VAMP sequence can be tolerated in a BoNT/D substrate useful in the invention.

A variety of BoNT/E substrates are useful in the invention. A BoNT/E substrate can contain, for example, at least six consecutive residues of SNAP-25, the six consecutive residues including Arg-Ile, or a peptidomimetic thereof. Such a BoNT/E substrate can have, for example, at least six consecutive residues of human SNAP-25, the six consecutive residues including $Arg_{180}$-$Ile_{181}$, or a peptidomimetic thereof. In particular embodiments, a BoNT/E substrate includes the amino acid sequence Gln-Ile-Asp-Arg-Ile-Met-Glu-Lys (SEQ ID NO: 45), or a peptidomimetic thereof. In other embodiments, a BoNT/E substrate includes residues 156 to 186 of human SNAP-25 (SEQ ID NO: 4), or a peptidomimetic thereof.

As used herein, the term "botulinum toxin serotype E recognition sequence" is synonymous with "BoNT/E recognition sequence" and means a scissile bond together with adjacent or non-adjacent recognition elements sufficient for detectable proteolysis at the scissile bond by a BoNT/E under appropriate conditions. A scissile bond cleaved by BoNT/E can be, for example, Arg-Ile.

One skilled in the art appreciates that a BoNT/E recognition sequence can correspond to a segment of a protein that is sensitive to cleavage by botulinum toxin serotype E, or can be substantially similar to a segment of a BoNT/E-sensitive protein. A variety of naturally occurring proteins sensitive to cleavage by BoNT/E are known in the art and include, for example, human, mouse and rat SNAP-25; mouse SNAP-23; chicken SNAP-25; goldfish SNAP-25A and SNAP-25B; zebrafish SNAP-25; *C. elegans* SNAP-25; and leech SNAP-25 (see Table E). Thus, a BoNT/E recognition sequence can correspond, for example, to a segment of human SNAP-25, mouse SNAP-25, rat SNAP-25, mouse SNAP-23, chicken SNAP-25, goldfish SNAP-25A or 25B, *C. elegans* SNAP-25, leech SNAP-25, or another naturally occurring protein sensitive to cleavage by BoNT/E. Furthermore, as shown in Table E and FIG. 5 above, comparison of native SNAP-23 and SNAP-25 amino acid sequences cleaved by BoNT/E reveals that such sequences are not absolutely conserved, indicating that a variety of amino acid substitutions and modifications relative to a naturally occurring BoNT/E-sensitive SNAP-23 or SNAP-25 sequence can be tolerated in a BoNT/E substrate useful in the invention.

A variety of useful BoNT/F substrates can be useful in the invention. Such BoNT/F substrates can include, for example, at least six consecutive residues of VAMP, the six consecutive residues including Gln-Lys, or a peptidomimetic thereof. In one embodiment, a BoNT/F substrate has at least six consecutive residues of human VAMP, the six consecutive residues including $Gln_{58}$-$Lys_{59}$, or a peptidomimetic thereof. In another embodiment, a BoNT/F substrate includes residues 27 to 116 of rat VAMP-2 (SEQ ID NO: 109), or a peptidomimetic thereof. In a further embodiment, a BoNT/F substrate includes the amino acid sequence Glu-Arg-Asp-Gln-Lys-Leu-Ser-Glu (SEQ ID NO: 46), or a peptidomimetic thereof.

The term "botulinum toxin serotype F recognition sequence," as used herein, is synonymous with "BoNT/F recognition sequence" and means a scissile bond together with adjacent or non-adjacent recognition elements sufficient for detectable proteolysis at the scissile bond by a BoNT/F under appropriate conditions. A scissile bond cleaved by BoNT/F can be, for example, Gln-Lys.

A variety of BoNT/F recognition sequences are well known in the art or can be defined by routine methods. A BoNT/F recognition sequence can include, for example, residues 27 to 116; residues 37 to 116; residues 1 to 86; residues 1 to 76; or residues 1 to 69 of rat VAMP-2 (SEQ ID NO: 109; Yamasaki et al., supra, 1994). A BoNT/F recognition sequence also can include, for example, residues 27 to 69 or residues 37 to 69 of rat VAMP-2 (SEQ ID NO: 109). It is understood that a similar BoNT/F recognition sequence can be prepared, if desired, from a corresponding (homologous) segment of another BoNT/F-sensitive VAMP isoform or homolog such as human VAMP-1 or human VAMP-2.

A BoNT/F recognition sequence can correspond to a segment of a protein that is sensitive to cleavage by botulinum toxin serotype F, or can be substantially similar to a segment of a BoNT/F-sensitive protein. A variety of naturally occurring proteins sensitive to cleavage by BoNT/F are known in the art and include, for example, human, mouse and bovine VAMP-1 and VAMP-2; rat VAMP-1 and VAMP-2; rat cellubrevin; chicken VAMP-1 and VAMP-2; Torpedo VAMP-1; Aplysia VAMP; *Drosophila* syb; and leech VAMP (see Table H). Thus, a BoNT/F recognition sequence can correspond, for example, to a segment of human VAMP-1 or VAMP-2, mouse VAMP-1 or VAMP-2, bovine VAMP-1 or VAMP-2, rat VAMP-1 or VAMP-2, rat cellubrevin, chicken VAMP-1 or VAMP-2, Torpedo VAMP-1, Aplysia VAMP, *Drosophila* syb, leech VAMP, or another naturally occurring protein sensitive to cleavage by BoNT/F. Furthermore, as shown in Table H above, comparison of native VAMP amino acid sequences cleaved by BoNT/F reveals that such sequences are not absolutely conserved (see, also, FIG. 6), indicating that a variety of amino acid substitutions and modifications relative to a naturally occurring BoNT/F-sensitive VAMP sequence can be tolerated in a BoNT/F substrate useful in the invention.

As for other clostridial toxin substrates, a variety of BoNT/G substrates can be useful in the invention. A BoNT/G substrate useful in the invention can have, for example, at least six consecutive residues of VAMP, the six consecutive residues including Ala-Ala, or a peptidomimetic thereof. Such a BoNT/G substrate can have, for example, at least six consecutive residues of human VAMP, the six consecutive residues including $Ala_{83}$-$Ala_{84}$, or a peptidomimetic thereof. In one embodiment, a BoNT/G substrate contains the amino acid sequence Glu-Thr-Ser-Ala-Ala-Lys-Leu-Lys (SEQ ID NO: 47), or a peptidomimetic thereof.

As used herein, the term "botulinum toxin serotype G recognition sequence" is synonymous with "BoNT/G recognition sequence" and means a scissile bond together with adjacent or non-adjacent recognition elements sufficient for detectable proteolysis at the scissile bond by a BoNT/G under appropriate conditions. A scissile bond cleaved by BoNT/G can be, for example, Ala-Ala.

A BoNT/G recognition sequence can correspond to a segment of a protein that is sensitive to cleavage by botulinum toxin serotype G, or can be substantially similar to such a BoNT/G-sensitive segment. As illustration in Table H above, a variety of naturally occurring proteins sensitive to cleavage by BoNT/G are known in the art and include, for example, human, mouse and bovine VAMP-1 and VAMP-2; rat VAMP-1 and VAMP-2; rat cellubrevin; chicken VAMP-1 and VAMP-2; and Torpedo VAMP-1. Thus, a BoNT/G recognition sequence can correspond, for example, to a segment of human VAMP-1 or VAMP-2, mouse VAMP-1 or VAMP-2, bovine VAMP-1 or VAMP-2, rat VAMP-1 or VAMP-2, rat cellubrevin, chicken VAMP-1 or VAMP-2, Torpedo VAMP-1, or another naturally occurring protein sensitive to cleavage by BoNT/G. Furthermore, as shown in Table H above, comparison of native VAMP amino acid sequences cleaved by BoNT/G reveals that such sequences are not absolutely conserved (see, also, FIG. 6), indicating that a variety of amino acid substitutions and modifications relative to a naturally occurring BoNT/G-sensitive VAMP sequence can be tolerated in a BoNT/G substrate useful in the invention.

A variety of TeNT substrates can be useful in the compositions and methods disclosed herein. A TeNT substrate useful in the invention can have, for example, at least six consecutive residues of VAMP, the six consecutive residues including Gln-Phe, or a peptidomimetic thereof. As an example, such a TeNT substrate can have at least six consecutive residues of human VAMP-2, the six consecutive residues including $Gln_{76}$-$Phe_{77}$, or a peptidomimetic thereof. In one embodiment, a TeNT substrate contains the amino acid sequence Gly-Ala-Ser-Gln-Phe-Glu-Thr-Ser (SEQ ID NO: 48), or a peptidomimetic thereof. In another embodiment, the TeNT substrate contains residues 33 to 94 of human VAMP-2 (SEQ ID NO: 11); residues 25 to 93 of human VAMP-2 (SEQ ID NO: 11); or residues 27 to 116 of rat VAMP-2 (SEQ ID NO: 109), or a peptidomimetic of one of these sequences.

As used herein, the term "tetanus toxin recognition sequence" means a scissile bond together with adjacent or non-adjacent recognition elements sufficient for detectable proteolysis at the scissile bond by a tetanus toxin under appropriate conditions. A scissile bond cleaved by TeNT can be, for example, Gln-Phe.

A variety of TeNT recognition sequences are well known in the art or can be defined by routine methods and include sequences corresponding to some or all of the hydrophilic core of a VAMP protein such as human VAMP-1 or human VAMP-2. A TeNT recognition sequence can include, for example, residues 25 to 93 or residues 33 to 94 of human VAMP-2 (SEQ ID NO: 11; Cornille et al., *Eur. J. Biochem.* 222:173-181 (1994); Foran et al., *Biochem.* 33: 15365-15374 (1994)); residues 51 to 93 or residues 1 to 86 of rat VAMP-2 (SEQ ID NO: 109; Yamasaki et al., supra, 1994); or residues 33 to 94 of human VAMP-1 (SEQ ID NO: 10). A TeNT recognition sequence also can include, for example, residues 25 to 86, residues 33 to 86 or residues 51 to 86 of human VAMP-2 (SEQ ID NO: 11) or rat VAMP-2 (SEQ ID NO: 109). It is understood that a similar TeNT recognition sequence can be prepared, if desired, from a corresponding (homologous) segment of another TeNT-sensitive VAMP isoform or species homolog such as human VAMP-1 or sea urchin or Aplysia VAMP.

Thus, a TeNT recognition sequence can correspond to a segment of a protein that is sensitive to cleavage by tetanus toxin, or can be substantially similar to a segment of a TeNT-sensitive protein. As shown in Table H above, a variety of naturally occurring proteins sensitive to cleavage by TeNT are known in the art and include, for example, human, mouse and bovine VAMP-1 and VAMP-2; rat VAMP-2; rat cellubrevin; chicken VAMP-2; Torpedo VAMP-1; sea urchin VAMP; Aplysia VAMP; squid VAMP; *C. elegans* VAMP; *Drosophila* n-syb; and leech VAMP. Thus, a TeNT recognition sequence can correspond, for example, to a segment of human VAMP-1 or VAMP-2, mouse VAMP-1 or VAMP-2, bovine VAMP-1 or VAMP-2, rat VAMP-2, rat cellubrevin, chicken VAMP-2, Torpedo VAMP-1, sea urchin VAMP, Aplysia VAMP, squid VAMP, *C. elegans* VAMP, *Drosophila* n-syb, leech VAMP, or another naturally occurring protein sensitive to cleavage by TeNT. Furthermore, comparison of native VAMP amino acid sequences cleaved by TeNT reveals that such sequences are not absolutely conserved (Table H and FIG. 6), indicating that a variety of amino acid substitutions and modifications relative to a naturally occurring TeNT-sensitive VAMP sequence can be tolerated in a TeNT substrate useful in the invention.

A clostridial toxin substrate useful in a substrate composition, cell or method of the invention can include one or multiple clostridial toxin cleavage sites for the same or different clostridial toxins. In particular embodiments, the invention provides a substrate composition, cell or method in which the clostridial toxin substrate contains a single clostridial toxin cleavage site. In other embodiments, the invention provides a substrate composition, cell or method in which the clostridial toxin substrate contains multiple cleavage sites for the same clostridial toxin. These cleavage sites can be accompanied by the same or different clostridial toxin recognition sequences. As an example, a substrate composition of the invention can include a clostridial toxin substrate having multiple cleavage sites for the same clostridial toxin intervening between the same donor fluorophore and acceptor. A clostridial toxin substrate useful in a substrate composition, cell or method of the invention can contain, for example, two or more, three or more, five or more, or ten or more cleavage sites for the same clostridial toxin. A clostridial toxin substrate useful in the invention also can have, for example, two, three, four, five, six, seven, eight, nine or ten cleavage sites for the same clostridial toxin; the multiple cleavage sites can intervene between the same or different donor fluorophore-acceptor pairs.

A clostridial toxin substrate useful in a substrate composition, cell or method of the invention also can include cleavage sites and recognition sequences for different clostridial toxins. In particular embodiments, the invention provides a substrate composition, cell or method in which the clostridial toxin substrate includes multiple cleavage sites for different clostridial toxins all intervening between the same donor fluorophore-acceptor pair. A substrate composition, cell or method of the invention can include a clostridial toxin substrate having, for example, cleavage sites for two or more, three or more, or five or more different clostridial toxins all intervening between the same donor fluorophore-acceptor pair. A substrate composition, cell or method of the invention also can incorporate a clostridial toxin substrate in which, for example, cleavage sites for two or more, three or more, or five or more different clostridial toxins intervene between at least two donor fluorophore-acceptor pairs. In particular embodiments, the invention provides a substrate composition, cell or method including a clostridial toxin substrate having cleavage sites for two, three, four, five, six, seven or eight different clostridial toxins, where the cleavage sites intervene between the same or different donor fluorophore-acceptor pairs. In further embodiments, the invention provides a substrate composition, cell or method in which the clostridial toxin substrate has, for example, any combination of two, three, four, five, six, seven or eight cleavage sites for any combination of the following clostridial toxins: BoNT/A, BoNT/B, BoNT/C1, BoNT/D, BoNT/E, BoNT/F, BoNT/G and TeNT.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the following claims.

We claim:

1. A cell comprising
   (a) at least one receptor that binds a clostridial toxin, and
   (b) a clostridial toxin substrate, said clostridial toxin substrate comprising:
      (i) a donor fluorophore;
      (ii) an acceptor having an absorbance spectrum overlapping the emission spectrum of said donor fluorophore; and
      (iii) a clostridial toxin recognition sequence comprising a clostridial toxin recognition sequence comprising a clostridial toxin $P_5$-$P_4$-$P_3$-$P_2$-$P_1$-$P_1'$-$P_2'$-$P_3'$-$P_4'$-$P_5'$ cleavage site sequence, said clostridial toxin $P_5$-$P_4$-$P_3$-$P_2$-$P_1$-$P_1'$-$P_2'$-$P_3'$-$P_4'$-$P_5'$ cleavage site sequence intervening between said donor fluorophore and said acceptor,
   wherein, under the appropriate conditions, resonance energy transfer is exhibited between said donor fluorophore and said acceptor.

2. The cell of claim 1, wherein said cell is a neuron.

3. The cell of claim 2, wherein said neuron is a peripheral neuron or a central nervous system neuron.

4. The cell of claim 2, wherein said neuron is a selected from the group consisting of a primary cell, a cultured cell, an established cell, a normal cell, a transformed cell, a tumor cell, an infected cell and a transfected cell.

5. The cell of claim 4, wherein said established line is a neuronal cell line selected from the group consisting of a neuroblastoma cell line, a hybrid neuronal cell line, a motor neuron cell line, a spinal cord cell line, a cerebral cortex cell line, a dorsal root ganglia cell line and a hippocampal cell line.

6. The cell of claim 1, wherein said cell is a non-neuronal cell.

7. The cell of claim 6, wherein said non-neuronal cell is selected from the group consisting of a glandular cell, an anterior pituitary cell, an adrenal cell, a pancreatic cell, an epithelial cell, a muscle cell, a fibroblast, a neutrophil, an eosinophil, a mast cell, a stomach cell, a hepatocyte, a kidney cell and an ovarian cell.

8. The cell of claim 6, wherein said non-neuronal cell is a selected from the group consisting of a primary cell, a cultured cell, an established cell, a normal cell, a transformed cell, a tumor cell, an infected cell and a transfected cell.

9. The cell of claim 8, wherein said established line is a non-neuronal cell line selected from the group consisting of a chromaffin cell line, an enterochromaffin cell line, a pancreatic cell line, a pancreatic islet β cell line, a pancreatic acinar cell line, an insulinoma HIT cell line, an INS-1 cell line, a steroid-producing ovarian cell line, an inner medullary collecting duct (IMCD) cell line, a platelet cell line, a neutrophil cell line, an eosinophil cell line, a mast cell line and a glucose transporter translocation cell line.

10. The cell of claim 1, wherein said receptor is selected from the group consisting of a high affinity receptor, a low affinity receptor, an endogenous receptor and an exogenous receptor.

11. The cell of claim 1, wherein said donor fluorophore is selected from the group consisting of blue fluorescent protein, cyan fluorescent protein, green fluorescent protein, yellow fluorescent protein and red fluorescent protein.

12. The cell of claim 1, wherein said acceptor is a fluorophore selected from the group consisting of blue fluorescent protein, cyan fluorescent protein, green fluorescent protein, yellow fluorescent protein and red fluorescent protein.

13. The cell of claim 1, wherein said acceptor is a non-fluorescent molecule.

14. The cell of claim 1, wherein said clostridial toxin substrate is a botulinum toxin substrate, wherein said clostridial toxin $P_5$-$P_4$-$P_3$-$P_2$-$P_1$-$P_1'$-$P_2'$-$P_3'$-$P_4'$-$P_5'$ recognition sequence is a botulinum toxin recognition sequence comprising a botulinum toxin $P_5$-$P_4$-$P_3$-$P_2$-$P_1$-$P_1'$-$P_2'$-$P_3'$-$P_4'$-$P_5'$ cleavage site sequence.

15. The cell of claim 14, wherein said botulinum toxin substrate is a BoNT/A substrate, wherein said botulinum toxin $P_5$-$P_4$-$P_3$-$P_2$-$P_1$-$P_1'$-$P_2'$-$P_3'$-$P_4'$-$P_5'$ recognition sequence is a BoNT/A recognition sequence comprising a BoNT/A $P_5$-$P_4$-$P_3$-$P_2$-$P_1$-$P_1'$-$P_2'$-$P_3'$-$P_4'$-$P_5'$ cleavage site sequence.

16. The cell of claim 15, wherein said BoNT/A $P_5$-$P_4$-$P_3$-$P_2$-$P_1$-$P_1'$-$P_2'$-$P_3'$-$P_4'$-$P_5'$ cleavage site comprises at least six consecutive residues of SNAP-25, said six consecutive residues comprising Gln-Arg.

17. The cell of claim 16, wherein said BoNT/A $P_5$-$P_4$-$P_3$-$P_2$-$P_1$-$P_1'$-$P_2'$-$P_3'$-$P_4'$-$P_5'$ cleavage site sequence comprises SEQ ID NO:41.

18. The cell of claim 14, wherein said botulinum toxin substrate is a BoNT/B substrate, wherein said botulinum toxin $P_5$-$P_4$-$P_3$-$P_2$-$P_1$-$P_1'$-$P_2'$-$P_3'$-$P_4'$-$P_5'$ recognition sequence is a BoNT/B recognition sequence comprising a BoNT/B $P_5$-$P_4$-$P_3$-$P_2$-$P_1$-$P_1'$-$P_2'$-$P_3'$-$P_4'$-$P_5'$ cleavage site sequence.

19. The cell of claim 18, wherein said BoNT/B $P_5$-$P_4$-$P_3$-$P_2$-$P_1$-$P_1'$-$P_2'$-$P_3'$-$P_4'$-$P_5'$ cleavage site sequence comprises at least six consecutive residues of VAMP, said six consecutive residues comprising Gln-Phe.

20. The cell of claim 19, wherein said BoNT/B $P_5$-$P_4$-$P_3$-$P_2$-$P_1$-$P_1'$-$P_2'$-$P_3'$-$P_4'$-$P_5'$ cleavage site region sequence comprises SEQ ID NO:42.

21. The cell of claim 14, wherein said botulinum toxin substrate is a BoNT/C1 substrate, wherein said botulinum toxin $P_5$-$P_4$-$P_3$-$P_2$-$P_1$-$P_1'$-$P_2'$-$P_3'$-$P_4'$-$P_5'$ recognition sequence is a BoNT/C1 recognition sequence comprising a BoNT/C1 $P_5$-$P_4$-$P_3$-$P_2$-$P_1$-$P_1'$-$P_2'$-$P_3'$-$P_4'$-$P_5'$ cleavage site sequence.

22. The cell of claim 21, wherein said BoNT/C1 $P_5$-$P_4$-$P_3$-$P_2$-$P_1$-$P_1'$-$P_2'$-$P_3'$-$P_4'$-$P_5'$ cleavage site sequence comprises at least six consecutive residues of syntaxin, said six consecutive residues comprising Lys Ala.

23. The cell of claim 21, wherein said BoNT/C1 $P_5$-$P_4$-$P_3$-$P_2$-$P_1$-$P_1'$-$P_2'$-$P_3'$-$P_4'$-$P_5'$ cleavage site sequence comprises at least six consecutive residues of SNAP-25, said six consecutive residues comprising Arg-Ala.

24. The cell of claim 23, wherein said BoNT/C1 $P_5$-$P_4$-$P_3$-$P_2$-$P_1$-$P_1'$-$P_2'$-$P_3'$-$P_4'$-$P_5'$ cleavage site sequence comprises SEQ ID NO:43.

25. The cell of claim 14, wherein said botulinum toxin substrate is a BoNT/D substrate, wherein said botulinum toxin $P_5$-$P_4$-$P_3$-$P_2$-$P_1$-$P_1'$-$P_2'$-$P_3'$-$P_4'$-$P_5'$ recognition sequence is a BoNT/D recognition sequence comprising a BoNT/D $P_5$-$P_4$-$P_3$-$P_2$-$P_1$-$P_1'$-$P_2'$-$P_3'$-$P_4'$-$P_5'$ cleavage site sequence.

26. The cell of claim 25, wherein said BoNT/D $P_5$-$P_4$-$P_3$-$P_2$-$P_1$-$P_1'$-$P_2'$-$P_3'$-$P_4'$-$P_5'$ cleavage site sequence comprises at least six consecutive residues of VAMP, said six consecutive residues comprising Lys-Leu.

27. The cell of claim 26, wherein said BoNT/D $P_5$-$P_4$-$P_3$-$P_2$-$P_1$-$P_1'$-$P_2'$-$P_3'$-$P_4'$-$P_5'$ cleavage site sequence comprises SEQ ID NO:44.

28. The cell of claim 14, wherein said botulinum toxin substrate is a BoNT/E substrate, wherein said botulinum toxin $P_5$-$P_4$-$P_3$-$P_2$-$P_1$-$P_1'$-$P_2'$-$P_3'$-$P_4'$-$P_5'$ recognition sequence is a BoNT/E recognition sequence comprising a BoNT/E $P_5-P_4-P_3-P_2-P_1-P_1'-P_2'-P_3'-P_4'-P_5'$ cleavage site sequence.

29. The cell of claim 28, wherein said BoNT/E $P_5-P_4-P_3-P_2-P_1-P_1'-P_2'-P_3'-P_4'-P_5'$ cleavage site sequence comprises at least six consecutive residues of SNAP 25, said six consecutive residues comprising Arg Ile.

30. The cell of claim 29, wherein said BoNT/E $P_5-P_4-P_3-P_2-P_1-P_1'-P_2'-P_3'-P_4'-P_5'$ cleavage site sequence comprises SEQ ID NO:45.

31. The cell of claim 14, wherein said botulinum toxin substrate is a BoNT/F substrate, wherein said botulinum toxin $P_5-P_4-P_3-P_2-P_1-P_1'-P_2'-P_3'-P_4'-P_5'$ recognition sequence is a BoNT/F recognition sequence comprising a BoNT/F $P_5-P_4-P_3-P_2-P_1-P_1'-P_2'-P_3'-P_4'-P_5'$ cleavage site sequence.

32. The cell of claim 31, wherein said BoNT/F $P_5-P_4-P_3-P_2-P_1-P_1'-P_2'-P_3'-P_4'-P_5'$ cleavage site sequence comprises at least six consecutive residues of VAMP, said six consecutive residues comprising Gln-Lys.

33. The cell of claim 32, wherein said BoNT/F $P_5-P_4-P_3-P_2-P_1-P_1'-P_2'-P_3'-P_4'-P_5'$ cleavage site sequence comprises SEQ ID NO:46.

34. The cell of claim 14, wherein said botulinum toxin substrate is a BoNT/G substrate, wherein said botulinum toxin $P_5-P_4-P_3-P_2-P_1-P_1'-P_2'-P_3'-P_4'-P_5'$ recognition sequence is a BoNT/G recognition sequence comprising a BoNT/G $P_5-P_4-P_3-P_2-P_1-P_1'-P_2'-P_3'-P_4'-P_5'$ cleavage site sequence.

35. The cell of claim 34, wherein said BoNT/G $P_5-P_4-P_3-P_2-P_1-P_1'-P_2'-P_3'-P_4'-P_5'$ cleavage site sequence comprises at least six consecutive residues of VAMP, said six consecutive residues comprising Ala-Ala.

36. The cell of claim 35, wherein said BoNT/G $P_5-P_4-P_3-P_2-P_1-P_1'-P_2'-P_3'-P_4'-P_5'$ cleavage site sequence comprises SEQ ID NO:47.

37. The cell of claim 1, wherein said clostridial toxin substrate is a TeNT toxin substrate, wherein said clostridial toxin $P_5-P_4-P_3-P_2-P_1-P_1'-P_2'-P_3'-P_4'-P_5'$ recognition sequence is a TeNT recognition sequence comprising a TeNT $P_5-P_4-P_3-P_2-P_1-P_1'-P_2'-P_3'-P_4'-P_5'$ cleavage site sequence.

38. The cell of claim 37, wherein said TeNT $P_5-P_4-P_3-P_2-P_1-P_1'-P_2'-P_3'-P_4'-P_5'$ cleavage site sequence comprises at least six consecutive residues of VAMP, said six consecutive residues comprising Gln-Phe.

39. The cell of claim 38, wherein said TeNT $P_5-P_4-P_3-P_2-P_1-P_1'-P_2'-P_3'-P_4'-P_5'$ cleavage site sequence comprises SEQ ID NO:48.

40. The cell of claim 1, wherein said clostridial toxin substrate comprises only one clostridial toxin $P_5-P_4-P_3-P_2-P_1-P_1'-P_2'-P_3'-P_4'-P_5'$ recognition sequence.

41. The cell of claim 1, wherein said clostridial toxin substrate comprises multiple clostridial toxin $P_5-P_4-P_3-P_2-P_1-P_1'-P_2'-P_3'-P_4'-P_5'$ recognition sequences from the same clostridial toxin.

42. The cell of claim 1, wherein said clostridial toxin substrate comprises multiple clostridial toxin $P_5-P_4-P_3-P_2-P_1-P_1'-P_2'-P_3'-P_4'-P_5'$ recognition sequences from different clostridial toxins.

43. The cell of claim 42, wherein said multiple clostridial toxin $P_5-P_4-P_3-P_2-P_1-P_1'-P_2'-P_3'-P_4'-P_5'$ recognition sequences comprise a BoNT/A $P_5-P_4-P_3-P_2-P_1-P_1'-P_2'-P_3'-P_4'-P_5'$ recognition sequence.

44. The cell of claim 42, wherein said multiple clostridial toxin $P_5-P_4-P_3-P_2-P_1-P_1'-P_2'-P_3'-P_4'-P_5'$ recognition sequences comprise a BoNT/A $P_5-P_4-P_3-P_2-P_1-P_1'-P_2'-P_3'-P_4'-P_5'$ recognition sequence and a BoNT/C1 $P_5-P_4-P_3-P_2-P_1-P_1'-P_2'-P_3'-P_4'-P_5'$ recognition sequence.

45. The cell of claim 42, wherein said multiple clostridial toxin $P_5-P_4-P_3-P_2-P_1-P_1'-P_2'-P_3'-P_4'-P_5'$ recognition sequences comprise a BoNT/A $P_5-P_4-P_3-P_2-P_1-P_1'-P_2'-P_3'-P_4'-P_5'$ recognition sequence, a BoNT/C1 $P_5-P_4-P_3-P_2-P_1-P_1'-P_2'-P_3'-P_4'-P_5'$ recognition sequence and a BoNT/E $P_5-P_4-P_3-P_2-P_1-P_1'-P_2'-P_3'-P_4'-P_5'$ recognition sequence.

46. The cell of claim 42, wherein said multiple clostridial toxin $P_5-P_4-P_3-P_2-P_1-P_1'-P_2'-P_3'-P_4'-P_5'$ recognition sequences comprise a BoNT/B $P_5-P_4-P_3-P_2-P_1-P_1'-P_2'-P_3'-P_4'-P_5'$ recognition sequence.

47. The cell of claim 42, wherein said multiple clostridial toxin $P_5-P_4-P_3-P_2-P_1-P_1'-P_2'-P_3'-P_4'-P_5'$ recognition sequences comprise a BoNT/B $P_5-P_4-P_3-P_2-P_1-P_1'-P_2'-P_3'-P_4'-P_5'$ recognition sequence and a BoNT/G $P_5-P_4-P_3-P_2-P_1-P_1'-P_2'-P_3'-P_4'-P_5'$ recognition sequence.

48. The cell of claim 42, wherein said multiple clostridial toxin $P_5-P_4-P_3-P_2-P_1-P_1'-P_2'-P_3'-P_4'-P_5'$ recognition sequences comprise a BoNT/D $P_5-P_4-P_3-P_2-P_1-P_1'-P_2'-P_3'-P_4'-P_5'$ recognition sequence.

49. The cell of claim 42, wherein said multiple clostridial toxin $P_5-P_4-P_3-P_2-P_1-P_1'-P_2'-P_3'-P_4'-P_5'$ recognition sequences comprise a BoNT/D $P_5-P_4-P_3-P_2-P_1-P_1'-P_2'-P_3'-P_4'-P_5'$ recognition sequence and a BoNT/F $P_5-P_4-P_3-P_2-P_1-P_1'-P_2'-P_3'-P_4'-P_5'$ recognition sequence.

50. The cell of claim 42, wherein said multiple clostridial toxin $P_5-P_4-P_3-P_2-P_1-P_1'-P_2'-P_3'-P_4'-P_5'$ recognition sequences comprise a BoNT/B $P_5-P_4-P_3-P_2-P_1-P_1'-P_2'-P_3'-P_4'-P_5'$ recognition sequence, a BoNT/D $P_5-P_4-P_3-P_2-P_1-P_1'-P_2'-P_3'-P_4'-P_5'$ recognition sequence, a BoNT/F $P_5-P_4-P_3-P_2-P_1-P_1'-P_2'-P_3'-P_4'-P_5'$ recognition sequence and a BoNT/G $P_5-P_4-P_3-P_2-P_1-P_1'-P_2'-P_3'-P_4'-P_5'$ recognition sequence.

51. The cell of claim 1, wherein said donor fluorophore and said acceptor are separated by at most 70 residues.

52. The cell of claim 1, wherein said donor fluorophore and said acceptor are separated by at most 100 residues.

53. The cell of claim 1, wherein said donor fluorophore and said acceptor are separated by at most 150 residues.

54. The cell of claim 1, wherein said donor fluorophore and said acceptor are separated by at most 200 residues.

55. The cell of claim 1, wherein said donor fluorophore and said acceptor are separated by the full length of a naturally-occurring clostridial toxin target protein.

56. The cell of claim 1, wherein said clostridial toxin substrate of claim 1 is transiently transfected into said cell.

57. The cell of claim 1, wherein said clostridial toxin substrate of claim 1 is encoded by a nucleic acid molecule linked to a regulatory element comprising a promoter.

58. The cell of claim 57, wherein said regulatory element further comprises an inducible enhancer element or a constitutive enhancer element.

59. The cell of claim 57, wherein said nucleic acid molecule is transiently transfected into said cell.

60. The cell of claim 57, wherein said nucleic acid molecule is stably transfected into said cell.

61. The cell of claim 42 wherein said clostridial toxin $P_5-P_4-P_3-P_2-P_1-P_1'-P_2'-P_3'-P_4'-P_5'$ recognition sequences are selected from the group consisting of: a BoNT/A $P_5-P_4-P_3-P_2-P_1-P_1'-P_2'-P_3'-P_4'-P_5'$ recognition sequence, a BoNT/B $P_5-P_4-P_3-P_2-P_1-P_1'-P_2'-P_3'-P_4'-P_5'$ recognition sequence, a BoNT/C1 $P_5-P_4-P_3-P_2-P_1-P_1'-P_2'-P_3'-P_4'-P_5'$ recognition sequence, a BoNT/D $P_5-P_4-P_3-P_2-P_1-P_1'-P_2'-P_3'-P_4'-P_5'$ recognition sequence, a BoNT/E $P_5-P_4-P_3-P_2-P_1-P_1'-P_2'-P_3'-P_4'-P_5'$ recognition sequence, a BoNT/F $P_5-P_4-P_3-P_2-P_1-P_1'-P_2'-P_3'-P_4'-P_5'$ recognition sequence, a BoNT/G $P_5-P_4-P_3-P_2-P_1-P_1'-P_2'-P_3'-P_4'-P_5'$ recognition sequence and a TeNT $P_5-P_4-P_3-P_2-P_1-P_1'-P_2'-P_3'-P_4'-P_5'$ recognition sequence.

* * * * *

UNITED STATES PATENT AND TRADEMARK OFFICE
CERTIFICATE OF CORRECTION

PATENT NO. : 7,749,759 B2  
APPLICATION NO. : 12/192925  
DATED : July 6, 2010  
INVENTOR(S) : Ester Fernandez-Salas et al.

It is certified that error appears in the above-identified patent and that said Letters Patent is hereby corrected as shown below:

On the Title Pg on page 2, Item (56) under "Other Publications", line 10, delete "337" and insert -- 3337 --, therefor.

On the Title Pg on page 2, Item (56) under "Other Publications", line 12, delete "Release" and insert -- Releases --, therefor.

On the Title Pg on page 2, Item (56) under "Other Publications", line 60, delete "Interaqency" and insert -- Interagency --, therefor.

On the Title Pg on page 2, Item (56) under "Other Publications", line 1, delete "Flourometric" and insert -- Fluorometric --, therefor.

On the Title Pg on page 2, Item (56) under "Other Publications", line 25, delete "using" and insert -- using a --, therefor.

In column 1, line 5, delete "11/621,212" and insert -- 11/621,212, filed --, therefor.

In column 1, line 6, delete "10/261,161" and insert -- 10/261,161, filed --, therefor.

In column 1, line 7, delete "7,183,066." and insert -- 7,183,066, each of which is hereby incorporated by reference in its entirety. --, therefor.

In column 1, line 35, delete "laringeal" and insert -- laryngeal --, therefor.

In column 4, line 47, delete "BOTOX-;" and insert -- BOTOX; --, therefor.

In column 5, line 65, delete "G6755588);" and insert -- g6755588); --, therefor.

In column 6, line 15, delete "g 15079184)," and insert -- g15079184), --, therefor.

In column 7, line 46-47, delete "(Neimann," and insert -- (Niemann, --, therefor.

Signed and Sealed this

Twenty-fourth Day of August, 2010

David J. Kappos  
*Director of the United States Patent and Trademark Office*

CERTIFICATE OF CORRECTION (continued)
U.S. Pat. No. 7,749,759 B2

In column 10, line 25, delete "ABoNT/B" and insert -- A BoNT/B --, therefor.

In column 15, line 21, delete "$_{(SEQ\ ID:}$ 32)" and insert -- (SEQ ID: 32) --, therefor.

In column 15, line 21, delete "$_{(SEQ\ ID:}$ 33)" and insert -- (SEQ ID: 33) --, therefor.

In column 15, line 22, delete "loligomer" and insert -- Oligomer --, therefor.

In column 24, line 43, delete "polybiquitin" and insert -- polyubiquitin --, therefor.

In column 25, line 46, delete "gramacidin" and insert -- gramicidin --, therefor.

In column 33, line 4-5, delete "(Folley" and insert -- (Foley --, therefor.

In column 35-36, under "Table B", line 12, delete "Napthalene" and insert -- Naphthalene --, therefor.

In column 35-36, under "Table B", line 22, delete "$_{F2}$DNB" and insert -- F$_2$DNB --, therefor.

In column 35-36, under "Table B", line 48, delete "diI-C$_{18}$" and insert -- diI-C$_{18}$ --, therefor.

In column 37-38, under "Table B", line 31, delete "BODIBY" and insert -- BODIPY --, therefor.

In column 37-38, under "Table B", line 1, delete "anthracence" and insert -- anthracene --, therefor.

In column 37-38, under "Table B", line 6, delete "diI-C$_{18}$," and insert -- diI-C$_{18}$, --, therefor.

In column 37-38, under "Table B", line 14, delete "dinitrophneyl;" and insert -- dinitrophenyl; --, therefor.

In column 37-38, under "Table B", line 16, delete "iodoacetetamido" and insert -- iodoacetamido --, therefor.

In column 37-38, under "Table B", line 18, delete "acETYLIMIDAZOLE;" and insert -- acetylimidazole; --, therefor.

In column 37-38, under "Table B", line 21, delete "thiosemicarazide;" and insert -- thiosemicarbazide; --, therefor.

In column 37-38, under "Table B", line 22, delete "difluro" and insert -- difluoro --, therefor.

CERTIFICATE OF CORRECTION (continued)
U.S. Pat. No. 7,749,759 B2

In column 37-38, under "Table B", line 25, delete "napthalene" and insert -- naphthalene --, therefor.

In column 37-38, under "Table B", line 26, delete "napthlene" and insert -- naphthalene --, therefor.

In column 37-38, under "Table B", line 33, delete "monobromobiamane;" and insert -- monobromobimane; --, therefor.

In column 37-38, under "Table B", line 35, delete "napthoxyacetic" and insert -- naphthoxyacetic --, therefor.

In column 37-38, under "Table B", line 36, delete "nirto" and insert -- nitro --, therefor.

In column 39, line 51, delete "-5-" and insert -- -S- --, therefor.

In column 40, line 48, delete "(pNO2)" and insert -- (p-NO$_2$) --, therefor.

In column 43, line 65, delete "Analyl." and insert -- Analyt. --, therefor.

In column 44, line 8, delete "(Kaschke" and insert -- Kaschke --, therefor.

In column 45, line 47, delete "hemagluttinin" and insert -- hemagglutinin --, therefor.

In column 45, line 65, delete "Ratan," and insert -- Raton, --, therefor.

In column 48, line 64, delete "5,965,699)." and insert -- 5,965,699. --, therefor.

In column 50, line 47, delete "Glu 194" and insert -- Glu194 --, therefor.

In column 53-54, line 8, delete "qkl" and insert -- erl --, therefor.

In column 53-54, line 23, delete "Drosphila" and insert -- Drosophila --, therefor.

In column 53-54, line 25, delete "Drosphila" and insert -- Drosophila --, therefor.

In column 58, line 8, delete "Ascissile" and insert -- A scissile --, therefor.

In column 59, line 30, delete "Ascissile" and insert -- A scissile --, therefor.

In column 119, line 23, in claim 4, delete "is a" and insert -- is --, therefor.

In column 119, line 41, in claim 8, delete "is a" and insert -- is --, therefor.

In column 120, line 15, in claim 16, delete "SNAP-25 ," and insert -- SNAP-25, --, therefor.

In column 120, line 43, in claim 22, delete "Lys Ala" and insert -- Lys-Ala --, therefor.

In column 120, line 46, in claim 23, delete "SNAP-25 ," and insert -- SNAP-25, --, therefor.

In column 121, line 6, in claim 29, delete "SNAP-25 ," and insert -- SNAP-25, --, therefor.

In column 121, line 7, in claim 29, delete "Arg Ile" and insert -- Arg-Ile --, therefor.